(12) United States Patent
Lauffer et al.

(10) Patent No.: US 8,481,524 B2
(45) Date of Patent: Jul. 9, 2013

(54) C-MET PROTEIN KINASE INHIBITORS

(75) Inventors: David Lauffer, Stow, MA (US); Pan Li, Lexington, MA (US); Nathan Waal, Cambridge, MA (US); Kira Mcginty, Schenectady, NY (US); Qing Tang, Acton, MA (US); Steven Ronkin, Watertown, MA (US); Luc Farmer, Foxboro, MA (US); Dean Shannon, Milford, MA (US); Dylan Jacobs, South Boston, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 509 days.

(21) Appl. No.: 12/751,016

(22) Filed: Mar. 31, 2010
(Under 37 CFR 1.47)

(65) Prior Publication Data

US 2011/0136789 A1 Jun. 9, 2011

Related U.S. Application Data

(63) Continuation of application No. PCT/US2008/078239, filed on Sep. 30, 2008.

(60) Provisional application No. 60/977,305, filed on Oct. 3, 2007.

(51) Int. Cl.
*C07D 417/14* (2006.01)

(52) U.S. Cl.
USPC .......... 514/211.09; 514/217.04; 514/318; 514/333; 514/338; 514/340; 514/341; 514/342; 540/466; 540/479; 540/543; 540/593; 546/125; 546/193; 546/256; 546/268.4; 546/270.4; 546/275.4

(58) Field of Classification Search
USPC .............. 514/211.09, 217.04, 318, 333, 338, 514/340, 341, 342; 540/466, 476, 543, 593; 546/125, 193, 256, 268.4, 270.4, 275.4
See application file for complete search history.

(56) References Cited

U.S. PATENT DOCUMENTS 7,872,031 B2 * 1/2011 Lauffer et al. ............... 514/340
8,232,406 B2 * 7/2012 Lauffer et al. ............. 546/268.4

FOREIGN PATENT DOCUMENTS

| WO | 2005/040154 | 5/2005 |
| WO | 2005/040345 | 5/2005 |
| WO | 2007/111904 | 10/2007 |

* cited by examiner

*Primary Examiner* — Brenda Coleman
(74) *Attorney, Agent, or Firm* — Daniel A. Pearson

(57) ABSTRACT

The present invention relates to compounds of formula I useful in the inhibition of c-Met protein kinase. The invention also provides pharmaceutically acceptable compositions comprising the compounds of the invention and methods of using the compositions in the treatment of proliferative disorders.

(I)

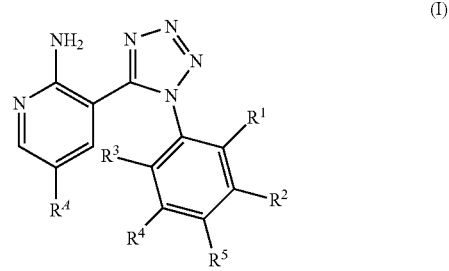

13 Claims, No Drawings

C-MET PROTEIN KINASE INHIBITORS

CROSS-REFERENCE TO RELATED APPLICATIONS

This present application claims the benefit, under 35 U.S.C. §119, to U.S. Provisional Application No. 60/977, 305, filed Oct. 3, 2007, and is a continuation of International Application No. PCT/US2008/078239, filed Dec. 30, 2008, the entire disclosures of each of which are incorporated herein by reference.

TECHNICAL FIELD OF THE INVENTION

The present invention relates to compounds useful as inhibitors of c-MET. The invention also provides pharmaceutically acceptable compositions comprising the compounds of the invention and methods of using the compositions in the treatment of various disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-MET, a receptor tyrosine kinase. c-MET, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-MET overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-MET is also implicated in atherosclerosis and lung fibrosis. Accordingly, there is a great need to develop compounds useful as inhibitors of c-MET protein kinase receptor.

SUMMARY OF THE INVENTION

It has been found that compounds of this invention, and pharmaceutically acceptable compositions thereof, are effective as inhibitors of c-MET. In particular, the compounds of the invention are superior to those compounds previously described as evidenced by their ability to inhibit the activity of c-Met in biological assays, such as, for example, the inhibition of c-Met activity in cells known to over-express this receptor. Accordingly, the invention features compounds having the formula:

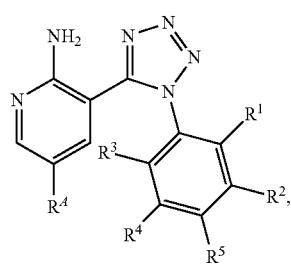

(I)

or a pharmaceutically acceptable salt thereof, wherein $R^1$, $R^2$, $R^3$, $R^4$, $R^5$, and $R^A$ are as defined below.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: tetrahydrofuran-2-yl, tetrahydrofuran-3-yl, tetrahydrothiophen-2-yl, tetrahydrothiophen-3-yl, 2-morpholino, 3-morpholino, 4-morpholino, 2-thiomorpholino, 3-thiomorpholino, 4-thiomorpholino, pyrrolidin-1-yl, pyrrolidin-2-yl, pyrrolidin-3-yl, tetrahydropiperazin-1-yl, tetrahydropiperazin-2-yl, tetrahydropiperazin-3-yl, piperidin-1-yl, piperidin-2-yl, piperidin-3-yl, piperidin-4-yl, pyrazolin-1-yl, pyrazolin-3-yl, pyrazolin-4-yl, pyrazolin-5-yl, thiazolidin-2-yl, thiazolidin-3-yl, thiazolidin-4-yl, thiazolidin-5-yl, imidazolidin-1-yl, imidazolidin-2-yl, imidazolidin-4-yl, imidazolidin-5-yl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic." Further examples of heteroaryl rings include the following monocycles: furanyl (e.g., furan-2-yl or furan-3-yl); imidazolyl (e.g., N-imidazolyl, imidazol-2-yl, imidazol-4-yl, or imidazol-5-yl); isoxazolyl (e.g., isoxazol-3-yl, isoxazol-4-yl, isoxazol-5-yl); oxazolyl (e.g., oxazol-2-yl, oxazol-4-yl, or oxazol-5-yl); pyrrolyl (e.g., N-pyrrolyl, pyrrol-2-yl, or pyrrol-3-yl); pyridinyl (e.g., pyrid-2-yl, pyrid-3-yl, or pyrid-4-yl); pyrimidinyl (e.g., pyrimidin-2-yl, pyrimidin-4-yl, or pyrimidin-5-yl); pyridazinyl (e.g., pyridazin-3-yl, pyridazin-4-yl, pyridazin-5-yl, or pyridazin-6-yl); thiazolyl (e.g., thiazol-2-yl, thiazol-4-yl, or thiazol-5-yl); tetrazolyl (e.g., tetrazol-1-yl or tetrazol-5-yl); triazolyl (e.g., 2-triazolyl or 5-triazolyl), thienyl (e.g., thiophen-2-yl or thiophen-3-yl); pyrazolyl (e.g., pyrazol-2-yl, pyrazol-3-yl, or pyrazol-4-yl); isothiazolyl; 1,2,3-oxadiazolyl; 1,2,5-oxadiazolyl; 1,2,4-oxadiazolyl; 1,2,3-triazolyl; 1,2,3-thiadiazolyl; 1,3,4-thiadiazolyl; 1,2,5-thiadiazolyl; pyrazinyl; 1,3,5-triazinyl; and the following bicycles: benzimidazolyl; benzofuryl; benzothienyl; indolyl (e.g., 2-indolyl); purinyl; quinolinyl (e.g., 2-quinolinyl, 3-quinolinyl, or 4-quinolinyl); and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $R^1$, $R^2$, $R^3$, $R^4$, $J^M$, $J^Q$, or $J^R$ below. Other suitable substituents include: halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with R°; —CH=CH(Ph), optionally substituted with R°; —NO₂; —CN; —N(R°)₂; —NR°C(O)R°; —NR°C(S)R°; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₂OR°; —S(O)₂N(R°)₂; —S(O)R°; —NR°S(O)₂N(R°)₂; —NR°S(O)₂R°; —N(OR°)R°; —C(=NH)—N(R°)₂; —(CH₂)₀₋₂NHC(O)R°; -L-R°;-L-N(R°)₂; -L-SR°; -L-OR°; -L-(C₃₋₁₀ cycloaliphatic), -L-(C₆₋₁₀ aryl), -L-(5-10 membered heteroaryl), -L-(5-10 membered heterocyclyl), oxo, C₁₋₄ haloalkoxy, C₁₋₄ haloalkyl, -L-NO₂, -L-CN, -L-OH, -L-CF₃; or two substituents, together with the intervening atoms to which they are bound, form a 5-7 membered saturated, unsaturated, or partially saturated ring, wherein L is a C₁₋₆ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)₂NH—, —S(O)₂NR°—, —NHS(O)₂—, —NR°S(O)₂—, —NHC(O)NH—, —NR°C(O)NH—, —NHC(O)NR°—, —NR°C(O)NR°, —OC(O)NH—, —OC(O)NR°—, —NHS(O)₂NH—, —NR°S(O)₂NH—, —NHS(O)₂NR°—, —NR°S(O)₂NR°—, —S(O)—, or —S(O)₂—, and wherein each independent occurrence of R° is selected from hydrogen, optionally substituted C₁₋₆ aliphatic, an unsubstituted 5-8 membered heteroaryl or heterocyclic ring, phenyl, —O(Ph), or —CH₂(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(haloC₁₋₄ aliphatic), or haloC₁₋₄ aliphatic, wherein each of the foregoing C₁₋₄ aliphatic groups of R° is unsubstituted.

In some embodiments, an aliphatic, cycloaliphatic, heteroaliphatic group, or a non-aromatic heterocyclic ring may contain one or more substituents. In some instances two substituents, on the same atom or on different atoms, together with the intervening atoms to which they are bound, form a 5-7 membered saturated, unsaturated, or partially saturated ring containing 0-3 heteroatoms selected from N, O, or S. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHS(O)₂(alkyl), or =NR*, where each R* is independently selected from hydrogen or an optionally substituted C₁₋₆ aliphatic, or two R* on the same nitrogen are taken together with the nitrogen to form a 5-8 membered heterocyclyl or heteroaryl ring having 1-3 heteroatoms independently selected from nitrogen, oxygen, and sulfur. Optional substituents on the aliphatic group of R* are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo (C₁₋₄ aliphatic), wherein each of the foregoing C₁₋₄aliphatic groups of R* is unsubstituted.

In some embodiments, optional substituents on the nitrogen of a non-aromatic heterocyclic ring include —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(=S)N(R⁺)₂, —C(=NH)—N(R⁺)₂, or —NR⁺S(O)₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂ (Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R⁺, on the same substituent or different substituents, taken together with the atom(s) to which each R⁺ group is bound, form a phenyl, 5-8-membered heterocyclyl, 5-8-membered heteroaryl, or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —O(halo(C₁₋₄ aliphatic)), or halo(C₁₋₄ aliphatic), wherein each of the foregoing C₁₋₄ aliphatic groups of R⁺ is unsubstituted.

As detailed above, in some embodiments, two independent occurrences of R° (or R⁺, or any other variable similarly defined herein), may be taken together with the atom(s) to which each variable is bound to form a phenyl, 5-8-membered heterocyclyl, 5-8-membered heteroaryl, or a 3-8 membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

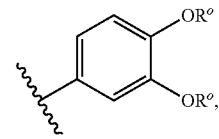

these two occurrences of R° are taken together with the oxygen atoms to which they are bound to form a fused 6-membered oxygen containing ring:

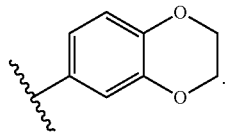

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

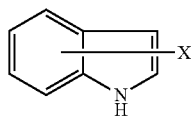

Figure a

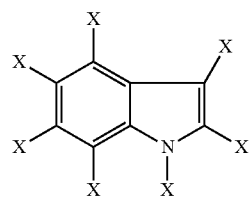

Figure b

This also applies to multiple ring systems fused to optional ring systems (which would be represented by dotted lines). For example, in Figure c, X is an optional substituent both for ring A and ring B.

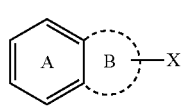

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

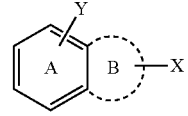

Figure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups in Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphorylation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the (R) and (S) configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays, or as c-MET inhibitors with improved therapeutic profile.

Description of Compounds of the Invention

In a first aspect, the invention features a compound having the formula:

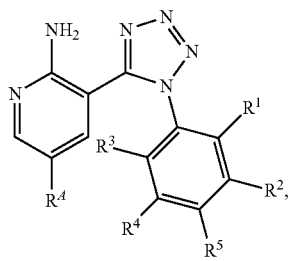

(I)

or a pharmaceutically acceptable salt thereof, wherein $R^A$ is

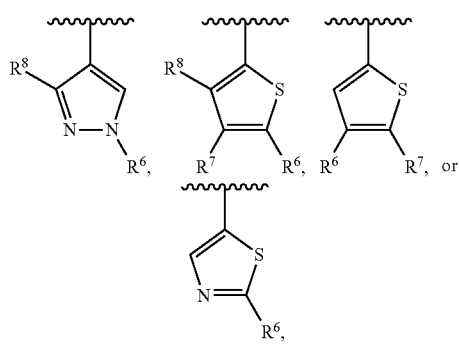

wherein each of $R^1$, $R^2$, $R^3$, and $R^4$ is, individually, hydrogen, Cl, or F, wherein at least one of $R^1$, $R^2$, $R^3$, and $R^4$ is Cl or F;

$R^5$ is $C_{1-4}$ aliphatic, $CH(R^{5a})_2$, $O-C_{1-4}$ aliphatic, $CH_2-O-C_{1-3}$ aliphatic, $O-(CH_2)_2-O-C_{1-3}$ aliphatic, or $O-CH_2C(R^{5a})_3$, wherein each $R^{5a}$ is, independently, hydrogen, or $C_{1-3}$ aliphatic, or two $R^{5a}$ together with the intervening carbon atom forms a 3-6 membered carbocyclic ring or a 5-6 membered heterocyclic ring having 1-2 oxygen atoms;

$R^6$ is

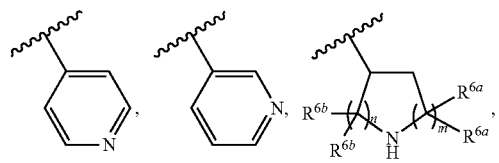

wherein each of m and n is, individually, 1 or 2, and each of $R^{6a}$ and $R^{6b}$ is, individually, hydrogen or a $C_{1-4}$ aliphatic, or two $R^{6a}$ or two $R^{6b}$ groups together with the carbon atom to which they are bonded form a cyclopropyl ring, wherein one $R^{6a}$ together with one $R^{6b}$ optionally form a 5 or 6-membered ring via a bond or an $C_{1-2}$ alkylidene linkage;

$R^7$ is a $C_{1-4}$ aliphatic, $O-C_{1-4}$ aliphatic, $C_{1-4}$ aliphatic-$O-C_{1-4}$ aliphatic, or $R^6$ and $R^7$ together with the thiophene ring to which they are bonded form the following structure:

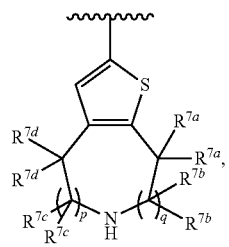

wherein each of $R^{7a}$, $R^{7b}$, $R^{7c}$, and $R^{7d}$ is, individually, hydrogen or a $C_{1-4}$ aliphatic, or two $R^{7a}$, $R^{7b}$, $R^{7c}$, or $R^{7d}$ groups together with the intervening atom form a cyclopropyl ring;

each of p and q is, individually, 0, 1, or 2; and $R^8$ is hydrogen, $CH_3$ or $CF_3$.

In one embodiment of compounds of formula I, $R^A$ is

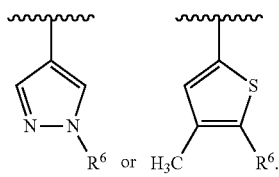

In another embodiment, $R^6$ is

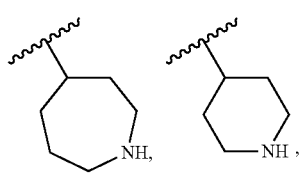

-continued

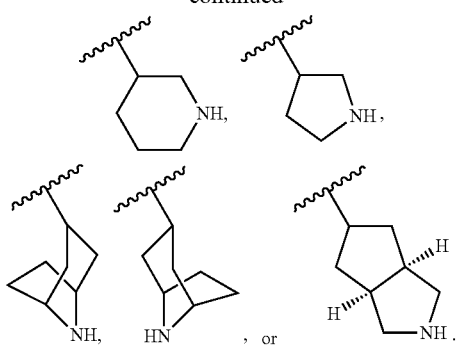

In yet another embodiment, $R^6$ is

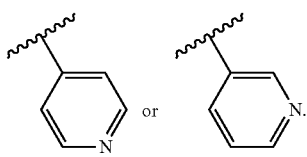 [SMILES: *c1ccncc1 ; "or" ; *c1cccnc1]

In another embodiment, $R^8$ is hydrogen.
In another embodiment, $R^4$ is

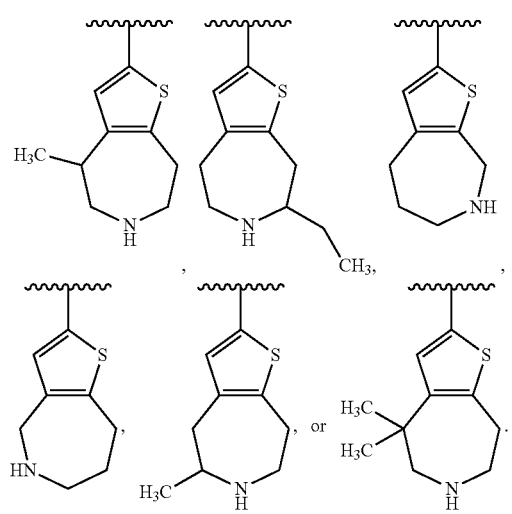

In one embodiment of compounds of formula I, one or two of $R^1$, $R^2$, $R^3$, and $R^4$ is fluorine and the remainder of $R^1$, $R^2$, $R^3$, and $R^4$ are hydrogen. In a further embodiment, each of $R^1$ and $R^2$ is fluorine and each of $R^3$ and $R^4$ is hydrogen.

In another embodiment, $R^5$ is $C_{1-4}$ aliphatic, cyclopropyl, $O$—$C_{1-4}$ aliphatic or —$OCH_2$-cyclopropyl In another embodiment of compounds of formula I, $R^5$ is

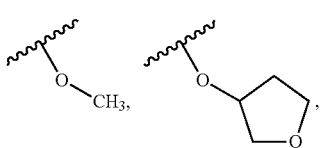

-continued

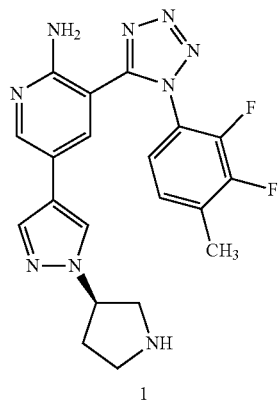 [SMILES: Cc1ccc(-n2nnnc2-c2cc(-c3cnn([C@@H]4CCNC4)c3)cnc2N)c(F)c1F]

In another aspect, the invention features a compound in Table 1.

TABLE 1

Compounds of Formula I

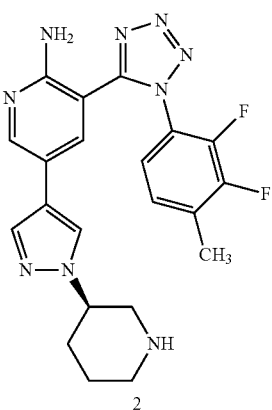 [SMILES: Cc1ccc(-n2nnnc2-c2cc(-c3cnn([C@@H]4CCCNC4)c3)cnc2N)c(F)c1F]

1

2

TABLE 1-continued
Compounds of Formula I
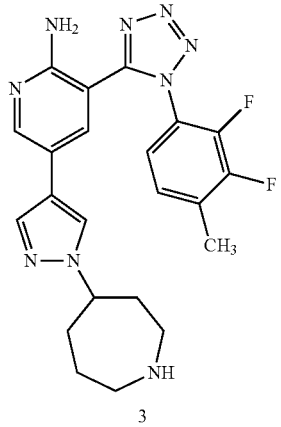 [SMILES: Cc1ccc(-n2nnnc2-c2cc(-c3cnn(C4CCCNCC4)c3)cnc2N)c(F)c1F]
3
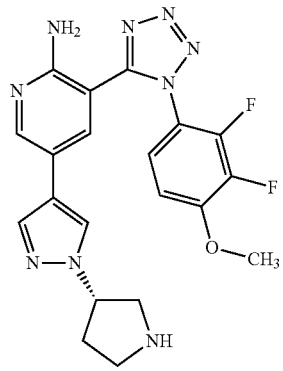
6
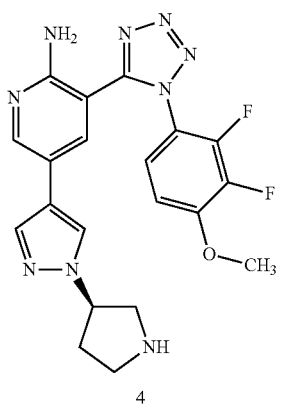 [SMILES: COc1ccc(-n2nnnc2-c2cc(-c3cnn([C@@H]4CCNC4)c3)cnc2N)c(F)c1F]
4
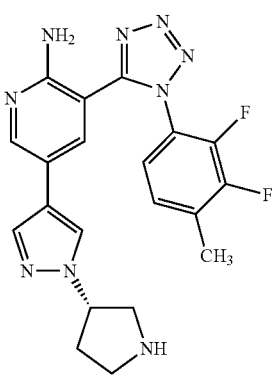
7
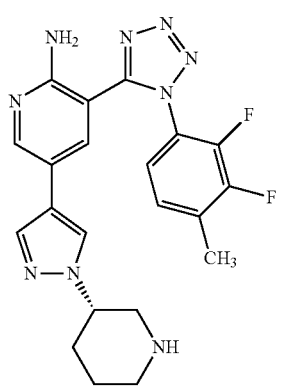
5
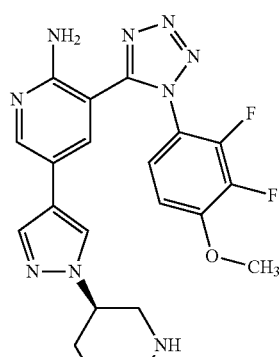
8

TABLE 1-continued
Compounds of Formula I
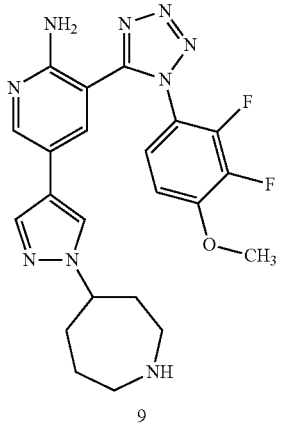 [SMILES: COc1ccc(-n2nnnc2-c2cc(-c3cnn(C4CCCNCC4)c3)cnc2N)c(F)c1F]
9
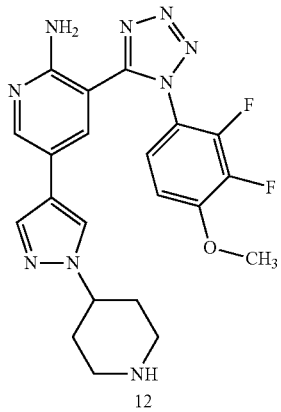
12
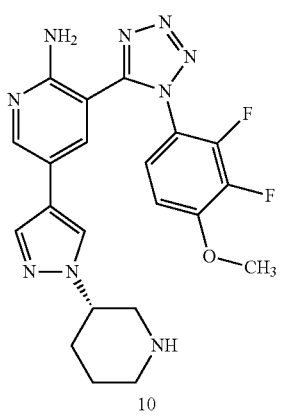 [SMILES: COc1ccc(-n2nnnc2-c2cc(-c3cnn([C@H]4CCCNC4)c3)cnc2N)c(F)c1F]
10
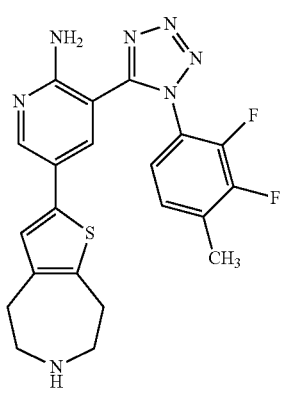
13
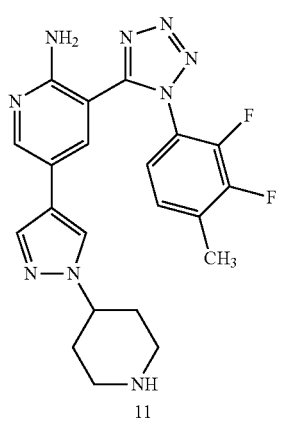 [SMILES: Cc1ccc(-n2nnnc2-c2cc(-c3cnn(C4CCNCC4)c3)cnc2N)c(F)c1F]
11
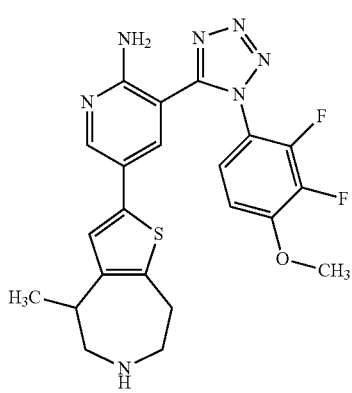
14

TABLE 1-continued
Compounds of Formula I
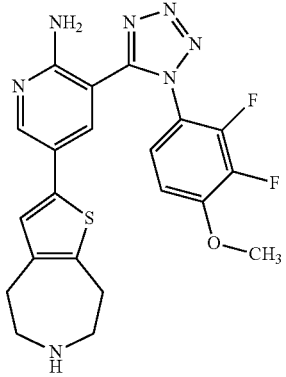
15
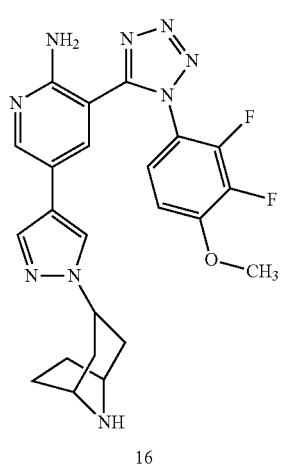 [SMILES: COc1ccc(-n2nnnc2-c2cc(-c3cnn(C4CC5CCC(C4)N5)c3)cnc2N)c(F)c1F]
16
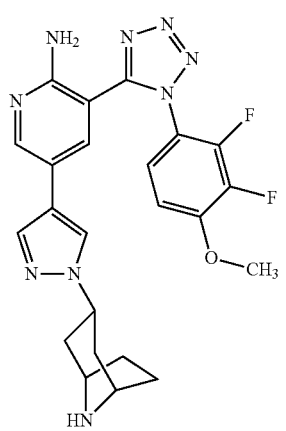
17
TABLE 1-continued
Compounds of Formula I
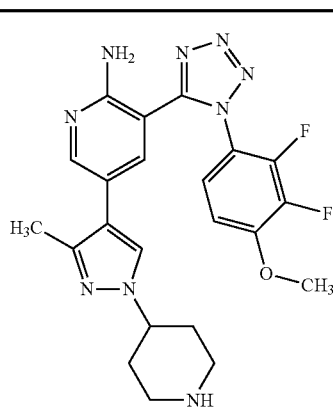
18
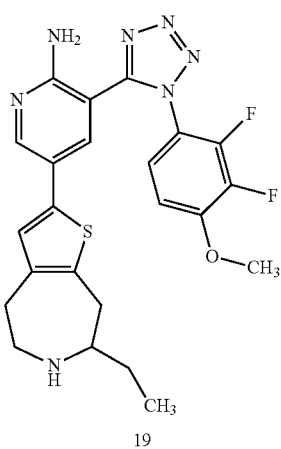 [SMILES: CCC1Cc2sc(-c3cnc(N)c(-c4nnnn4-c4ccc(OC)c(F)c4F)c3)cc2CCN1]
19
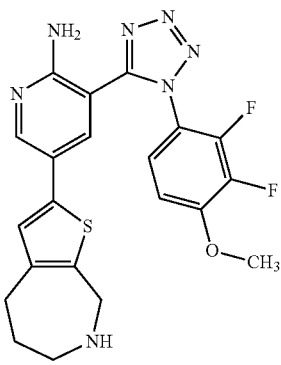
20

TABLE 1-continued
Compounds of Formula I
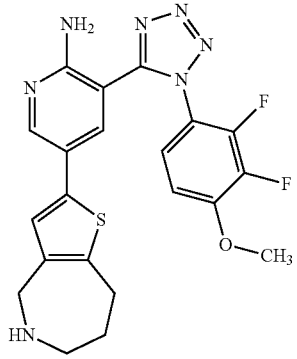
21
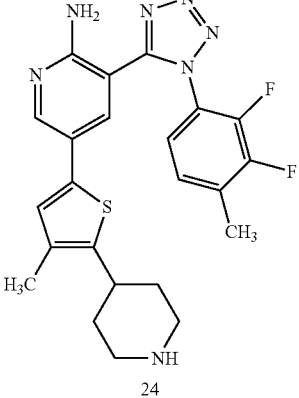
24
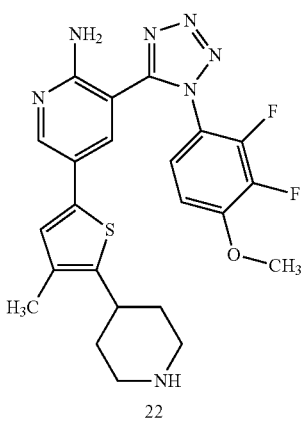 [SMILES: COc1ccc(-n2nnnc2-c2cc(-c3cc(C)c(C4CCNCC4)s3)cnc2N)c(F)c1F]
22
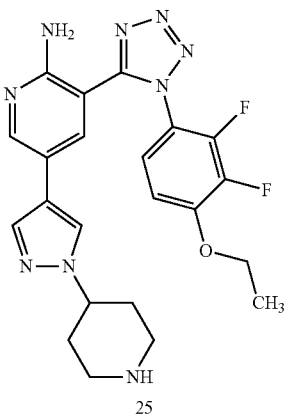 [SMILES: CCOc1ccc(-n2nnnc2-c2cc(-c3cnn(C4CCNCC4)c3)cnc2N)c(F)c1F]
25
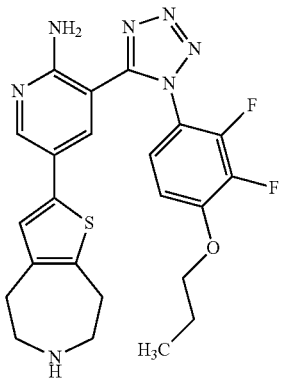
23
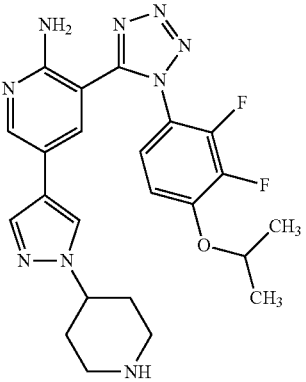
26

TABLE 1-continued
Compounds of Formula I
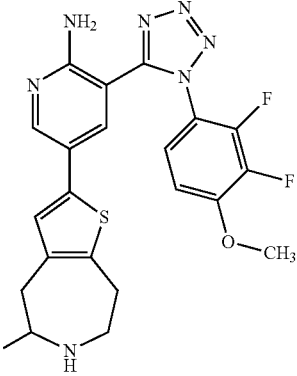
27
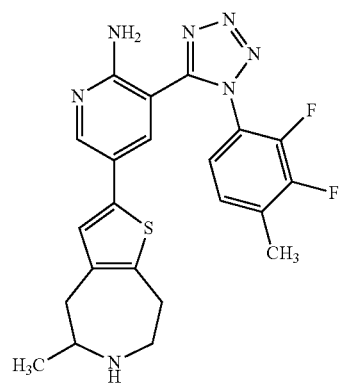
28
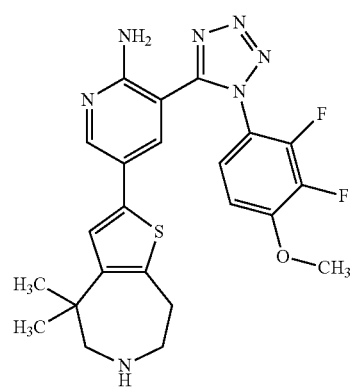
29
TABLE 1-continued
Compounds of Formula I
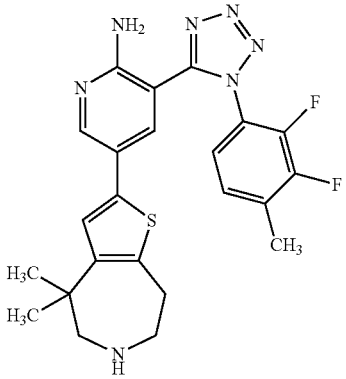
30
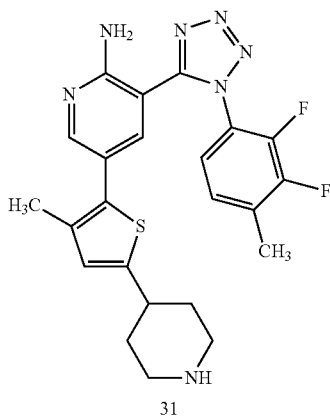 [SMILES: Cc1cc(C2CCNCC2)sc1-c1cnc(N)c(-c2nnnn2-c2ccc(C)c(F)c2F)c1]
31
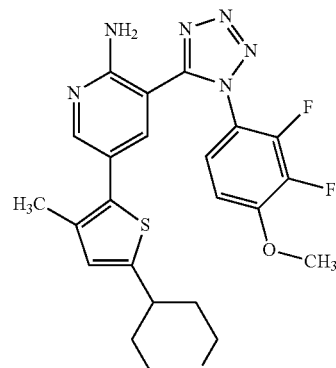
32

TABLE 1-continued
Compounds of Formula I
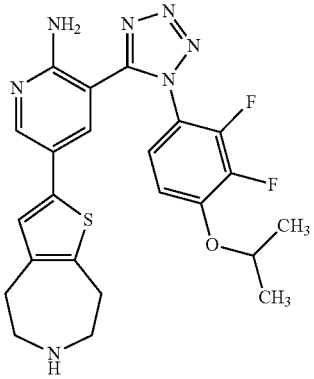
33
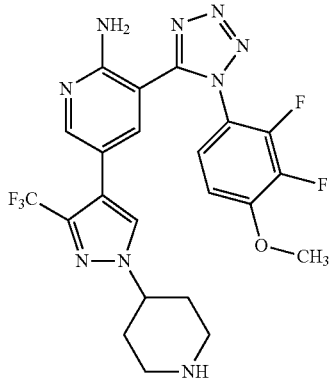
36
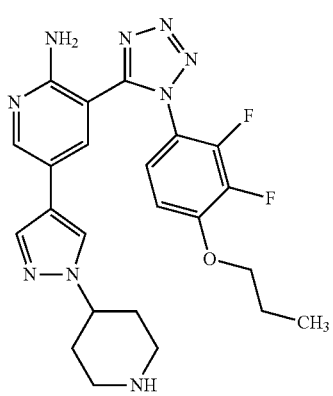
34
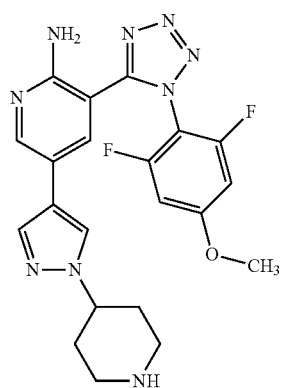
37
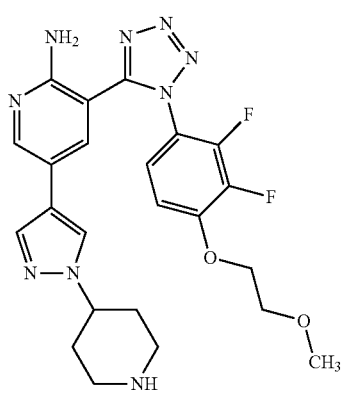
35
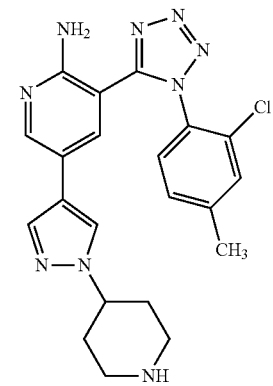
38

TABLE 1-continued
Compounds of Formula I
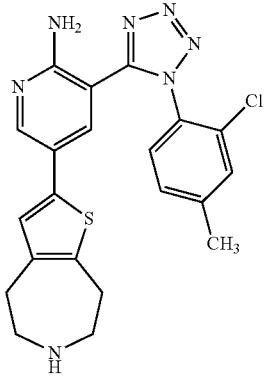
39
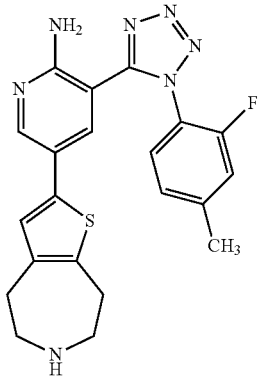
42
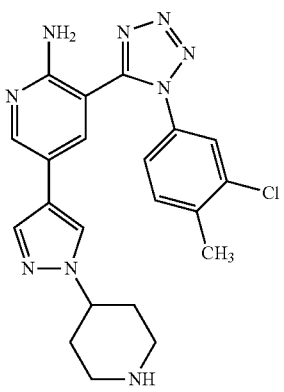
40
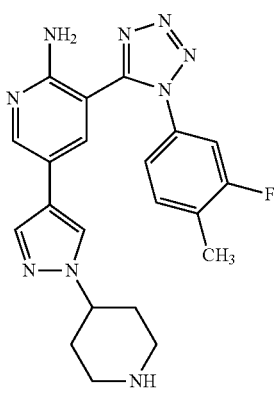
43
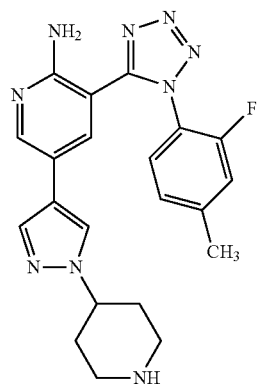
41
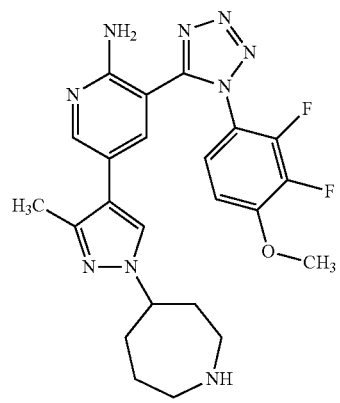
44

TABLE 1-continued
Compounds of Formula I
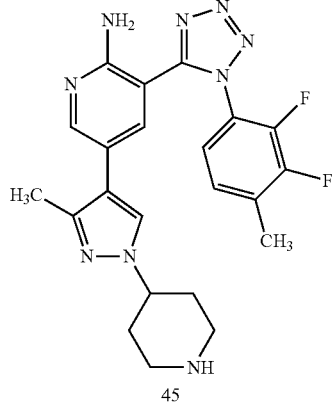 [SMILES: Cc1ccc(-n2nnnc2-c2cc(-c3cn(C4CCNCC4)nc3C)cnc2N)c(F)c1F]
45
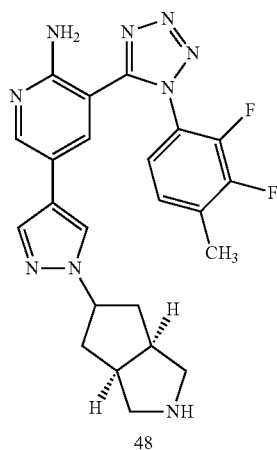
48
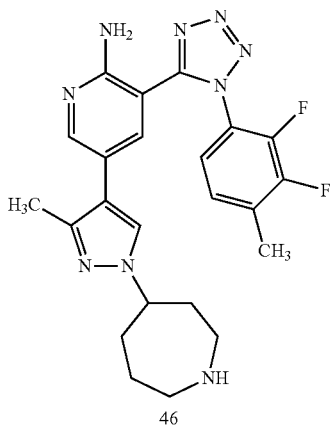 [SMILES: Cc1ccc(-n2nnnc2-c2cc(-c3cn(C4CCCNCC4)nc3C)cnc2N)c(F)c1F]
46
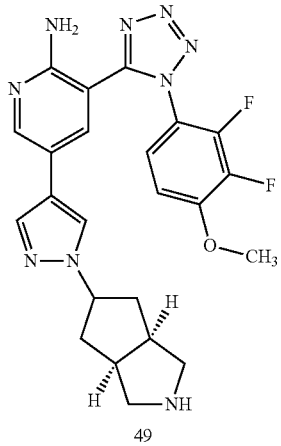
49
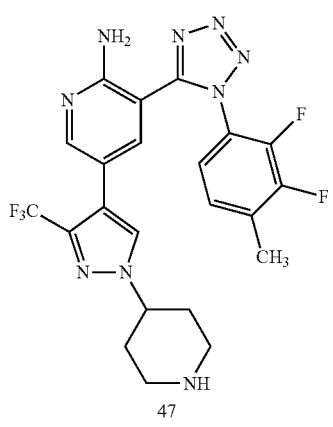 [SMILES: Cc1ccc(-n2nnnc2-c2cc(-c3cn(C4CCNCC4)nc3C(F)(F)F)cnc2N)c(F)c1F]
47
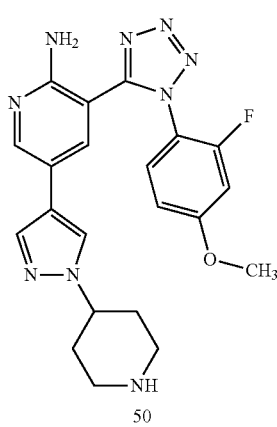 [SMILES: COc1ccc(-n2nnnc2-c2cc(-c3cnn(C4CCNCC4)c3)cnc2N)c(F)c1]
50

TABLE 1-continued
Compounds of Formula I
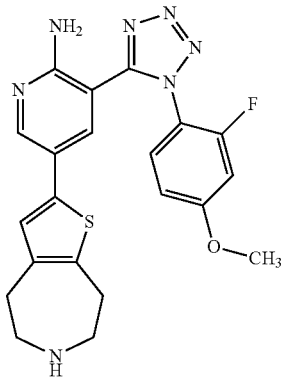
51
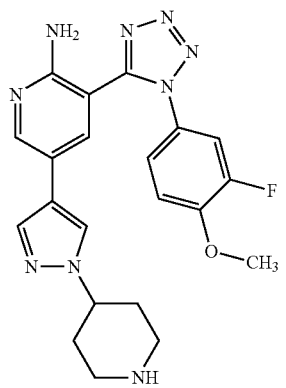
52
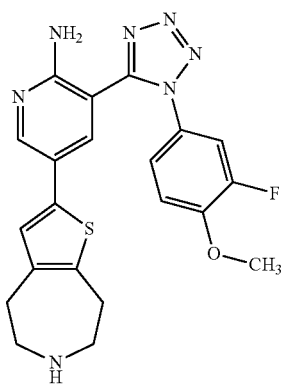
53
TABLE 1-continued
Compounds of Formula I
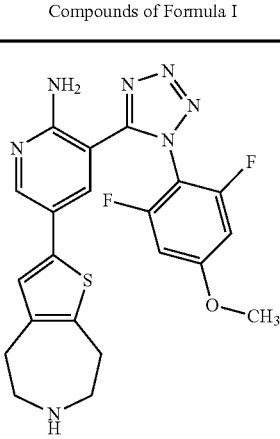
54
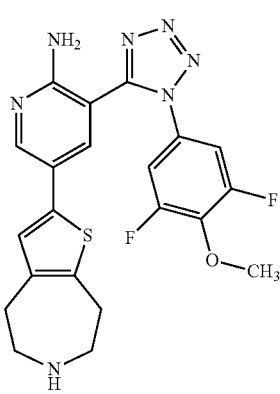
55
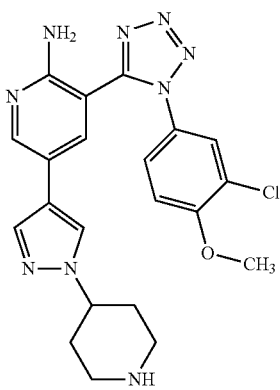
56

TABLE 1-continued
Compounds of Formula I
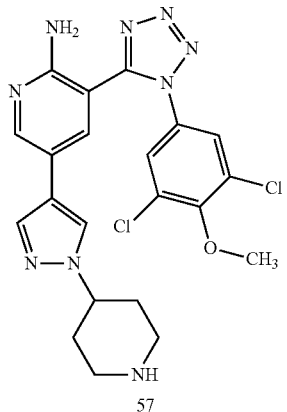 [SMILES: COc1c(Cl)cc(-n2nnnc2-c2cc(-c3cnn(C4CCNCC4)c3)cnc2N)cc1Cl]
57
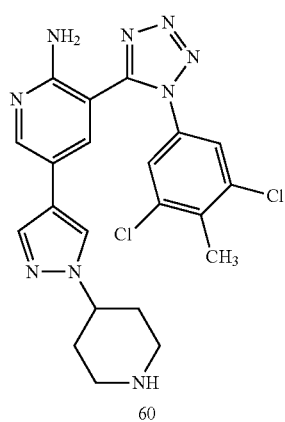 [SMILES: Cc1c(Cl)cc(-n2nnnc2-c2cc(-c3cnn(C4CCNCC4)c3)cnc2N)cc1Cl]
60
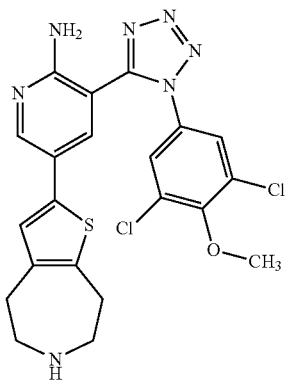
58
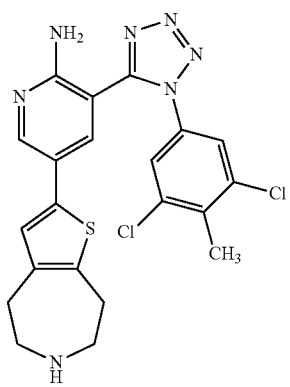
61
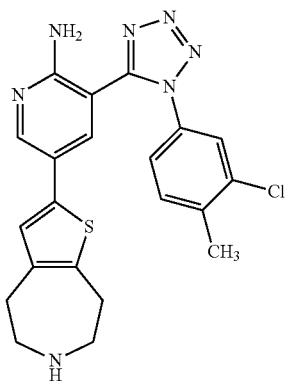
59
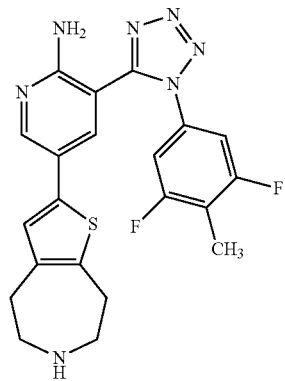
62

TABLE 1-continued
Compounds of Formula I
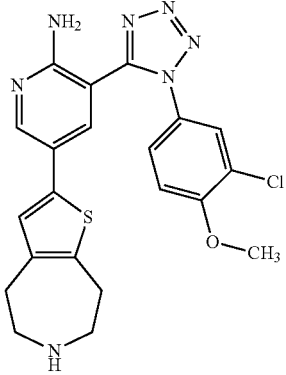
63
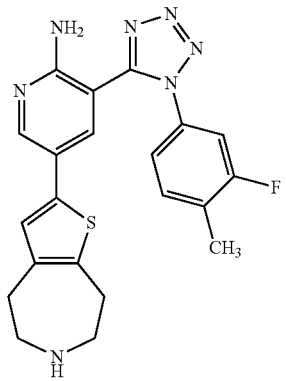
64
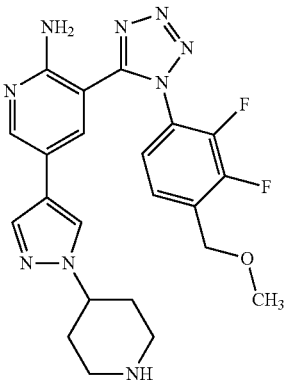
65
TABLE 1-continued
Compounds of Formula I
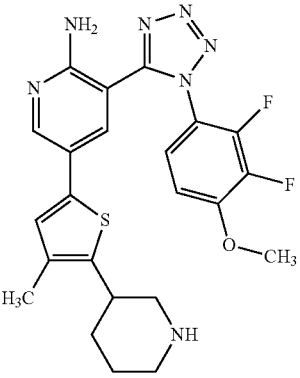
66
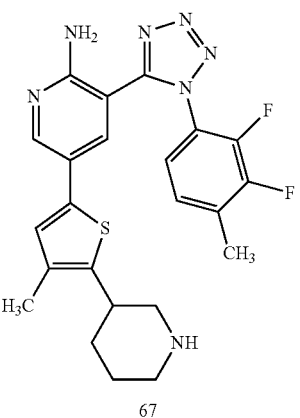 [SMILES: Cc1cc(-c2cnc(N)c(-c3nnnn3-c3ccc(C)c(F)c3F)c2)sc1C1CCCNC1]
67
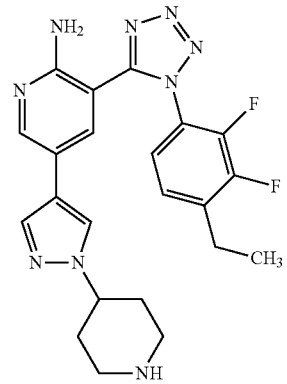
68

TABLE 1-continued
Compounds of Formula I
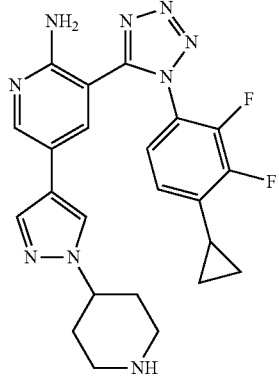
69
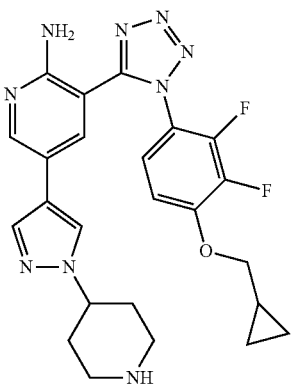
70
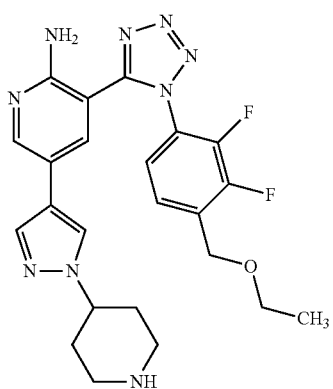
71
TABLE 1-continued
Compounds of Formula I
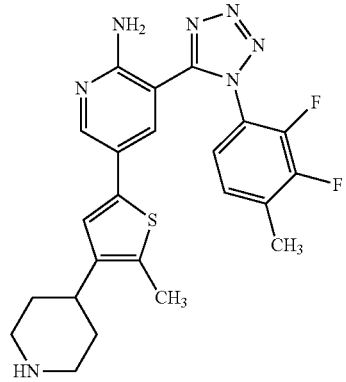
72
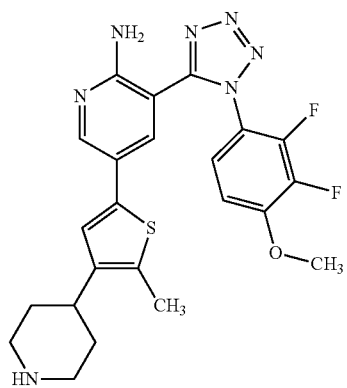
73
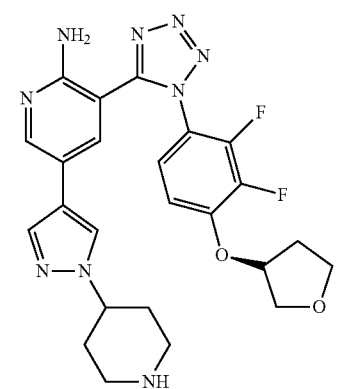
74

TABLE 1-continued
Compounds of Formula I
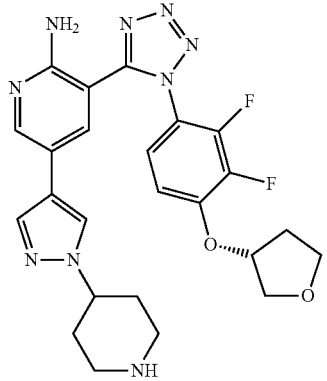
75
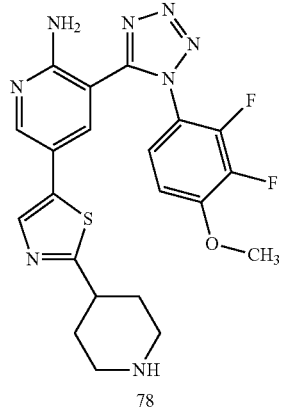 [SMILES: COc1ccc(-n2nnnc2-c2cc(-c3cnc(C4CCNCC4)s3)cnc2N)c(F)c1F]
78
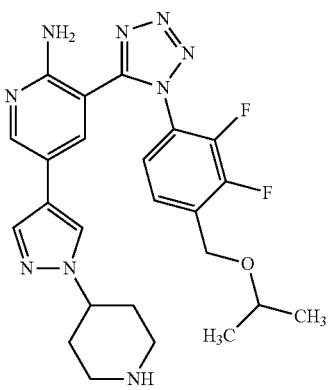
76
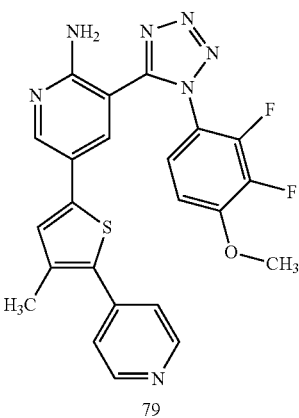 [SMILES: COc1ccc(-n2nnnc2-c2cc(-c3cc(C)c(-c4ccncc4)s3)cnc2N)c(F)c1F]
79
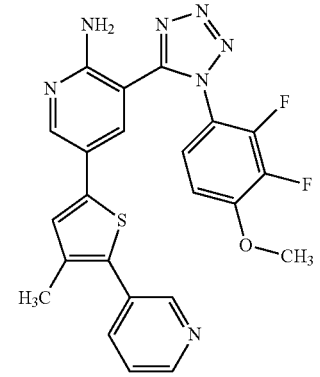
77
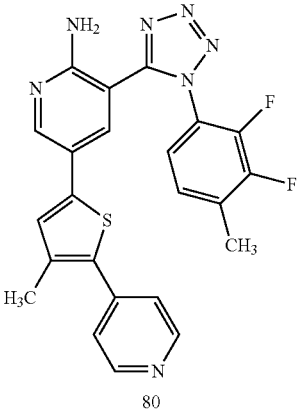 [SMILES: Cc1cc(-c2cnc(N)c(-c3nnnn3-c3ccc(C)c(F)c3F)c2)sc1-c1ccncc1]
80

TABLE 1-continued

Compounds of Formula I

81

Compositions, Formulations, and Administration of Compounds of the Invention

In another aspect, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit c-MET in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil;

olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol.

Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration.

Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

According to one embodiment, the invention relates to a method of inhibiting c-MET protein kinase activity in a biological sample comprising the step of contacting said biological sample with a compound of this invention, or a composition comprising said compound. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity in a biological sample is useful for a variety of purposes known to one of skill in the art. Examples of such purposes include, but are not limited to, biological specimen storage and biological assays. In one embodiment, the method of inhibiting kinase activity in a biological sample is limited to non-therapeutic methods.

The term "c-MET" is synonymous with "c-Met," "cMet", "MET", "Met" or other designations known to one skilled in the art.

According to another embodiment, the invention relates to a method of inhibiting c-MET kinase activity in a patient comprising the step of administering to said patient a compound of the present invention, or a composition comprising said compound.

The term "c-MET-mediated disease" or "c-MET-mediated condition", as used herein, means any disease state or other deleterious condition in which c-MET is known to play a role. The terms "c-MET-mediated disease" or "c-MET-mediated condition" also mean those diseases or conditions that are alleviated by treatment with a c-MET inhibitor. Such conditions include, without limitation, renal, gastric, colon, brain, breast, prostate, and lung cancer, glioblastoma, atherosclerosis, lung fibrosis, conditions associated with organ transplantation, allergic disorders, and autoimmune disorders.

In one aspect, the present invention features a method treating a proliferative disorder in a patient comprising the step of administering to the patient a therapeutically effective dose of any of the compounds or compositions of the invention.

According to one embodiment, the proliferative disorder is cancer, such as, for example, renal, gastric, colon, brain, breast, liver, prostate, and lung cancer, or a glioblastoma.

In another embodiment, the present invention relates to a method of treating or lessening the severity of brain cancer in a patient in need thereof, comprising administering to said patient a compound of the present invention or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient a compound of the present invention or composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with the compounds of this invention to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycinp, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), aza-epothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), O6 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

Preparation of Compounds of the Invention

The following definitions describe terms and abbreviations used herein:
Boc t-butoxylcarbonyl
brine saturated NaCl (aqueous)
BSA bovine serum albumin
DCM dichloromethane
DIEA diisopropylethylamine
DMA dimethylacetamide
DME 1,2-dimethoxyethane
DMF dimethylformamide
DMSO methylsulfoxide
ESMS electrospray mass spectrometry
Et ethyl
$Et_2O$ ethyl ether
EtOAc ethyl acetate
EtOH ethyl alcohol
HOAc acetic acid
HPLC high performance liquid chromatography
J In some structures, "J" is used to represent an iodine atom
LAH lithium aluminum hydride
Lawesson's Reagent 2,4-bis(4-methoxyphenyl)-1,3-dithia-2,4-diphosphetane-2,4-disulfide
LCMS liquid chromatography-mass spectrometry
Me methyl
MeOH methanol
Ms methanesulfonyl
NBS N-bromosuccinimide
NMP N-methylpyrrolidine
$PdCl_2(dppf)$ 1,1'-bis(diphenylphosphino)ferrocene]dichloropalladium(II)
Ph phenyl
RT or rt room temperature
tBu tertiary butyl
TCA trichloroacetic acid
THF tetrahydrofuran
TEA triethylamine
Tf trifluoromethanesulfonyl
TFA trifluoacetic acid
TsOH p-toluenesulfonic acid As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

General Synthetic Procedures

In general, the compounds of this invention may be prepared by methods described herein or known to those skilled in the art for the preparation of analogous compounds. The following non-limiting schemes and examples are presented to further exemplify the invention. Physiochemical characterization of selected compounds of the invention is provided in Table 2.

Compounds of the invention can, in general, be prepared as shown in Scheme 1. Accordingly, 2-fluoronicotinic acid is coupled to an aniline of formula I-a to produce a compound of formula I-b, wherein $R^1$, $R^2$, $R^3$, $R^4$, and $R^5$ are as defined elsewhere herein for a compound or formula I. The coupling can be affected by first forming an acyl chloride or a mixed anhydride followed by reaction with the aniline. Suitable reagents for the formation of acyl chlorides include oxalyl chloride. Suitable reagents for the formation of a mixed anhydride include isobutylchloroformate. Alternatively, the coupling reaction can be performed using a conventional amide bond-forming reagent known to a person skilled in the art, such as, for example, 1-benzotriazol-1-yloxy-bis(pyrrolidino)uronium hexafluorophosphate (BBC), O-(7-azabenzotriazol-1-yl)-1,1,3,3-tetramethyluronium hexafluorophosphate (HATU), O-(7-azabenzotriazol-1-yl)-1,1,3,3-bis(tetramethylene)uronium hexafluorophosphate (HAPyU), O-(benzotriazol-1-yl)-1,1,3,3-tetramethyluronium hexafluorophosphate (HBTU), 1,3-diisopropylcarbodiimide (DIC), 1-ethyl-3-(3'-dimethylaminopropyl)carbodiimide hydrochloride (EDC), O-(7-azabenzotriazol-1-yl)-tris(dimethylamino)phosphonium hexafluorophosphate (AOP), 1-benzotriazolyoxytris(dimethylamino)phosphonium hexafluorophosphate (BOP), 7-azobenzotriazolyoxytris(pyrrolidino)phosphonium hexafluorophosphate (PyABOP), or 1-benzotriazolyoxytris(pyrrolidino)phosphonium hexafluorophosphate (PyBOP).

The fluoro group of a compound of formula I-b is then displaced with an amine to form a compound of formula I-c. The amine can be protected with a group (PG) that keeps the amine nitrogen sufficiently nucleophilic for the displacement to take place. Examples include t-butyl or benzyl-type amine protecting groups.

The amide moiety of a compound of formula I-c is then transformed into a tetrazole ring to produce a compound of formula I-d. This transformation can be affected by sequential reaction of the amide with triphenylphosphine and trimethylsilyl azide, followed by heating. Alternatively, the compound of formula I-c can be sequentially reacted with 2,4-bis(4-methoxyphenyl)-1,3-dithia-2,4-diphosphetane-2,4-disulfide (Lawesson's reagent), hydrazine, and $NaNO_2$.

The amino pyridine ring of a compound of formula I-d is then halogenated to produce a compound of formula I-e. In one example, halogenation is affected with N-bromosuccinimide to produce the bromide. The compound of formula I-e can then be reacted with intermediate $R^4$-Metal in a catalyst-mediated cross coupling reaction and any protecting groups removed to form a compound of formula I, wherein $R^4$ is as defined elsewhere herein. Non-limiting examples of $R^4$ include optionally substituted pyrazoles, thiophenes, thienoazepines, or thiazoles. The Metal group can be, for example, —B(OAlkyl)$_2$ or —B(OH)$_2$(Suzuki reaction), —Mg-Hal (Kumada reaction), —Zn-Hal (Negishi reaction), —Sn(Alkyl)$_3$ (Stille reaction), —Si(Alkyl)$_3$ (Hiyama reaction), —Cu-Hal, —ZrCp$_2$Cl, or —AlMe$_2$. The catalyst for the cross-coupling reaction can be, for example, a palladium catalyst/ligand system (such as, for example, Pd(PPh$_3$)$_4$, Pd(PtBu$_3$)$_4$, Pd[P(Me)(tBu$_3$)]$_4$, PdCl$_2$(PPh$_3$)$_2$, PdCl$_2$(dppf), Pd$_2$(dba)$_3$BINAP, or Pd$_2$(dba)$_3$P(o-tol)$_3$ (see Fu and Littke, *Angew. Chem. Int. Ed.* 41:4176-4211, 2002; Nicolaou et al., *Angew. Chem. Int. Ed.* 44:4442-4489, 2005; or Hassen et al., *Chemical Reviews* 102(5):1359-1469, 2002). The reaction is usually performed in the presence of a base. Alternatively, compound of formula I-e can be transformed into a boronate or boronic acid of formula I-f. Subsequent reaction with $R^4$-halide in a catalyst-mediated cross coupling reaction as described above also produces a compound of formula I.

Scheme 1.
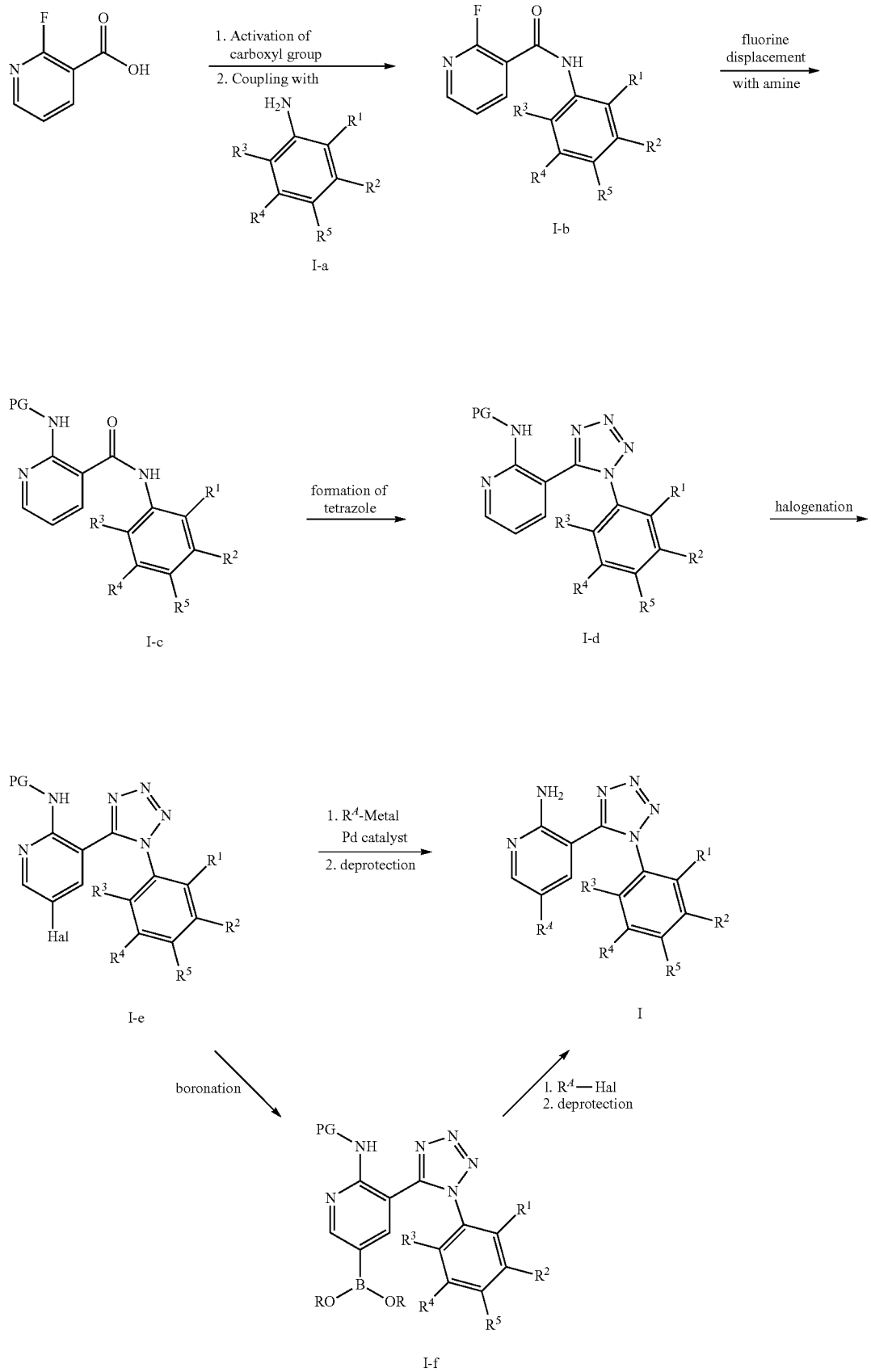

SYNTHETIC EXAMPLES

Example 1 tert-Butyl 4-(4-bromo-1H-pyrazol-1-yl)piperidine-1-carboxylate

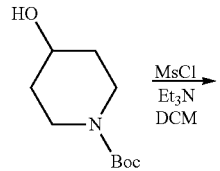

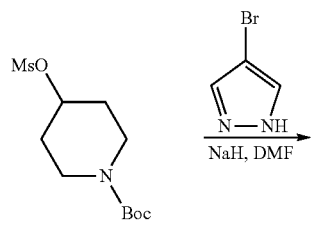

Example 2

4-(4-bromo-3-methyl-1H-pyrazol-1-yl)piperidine

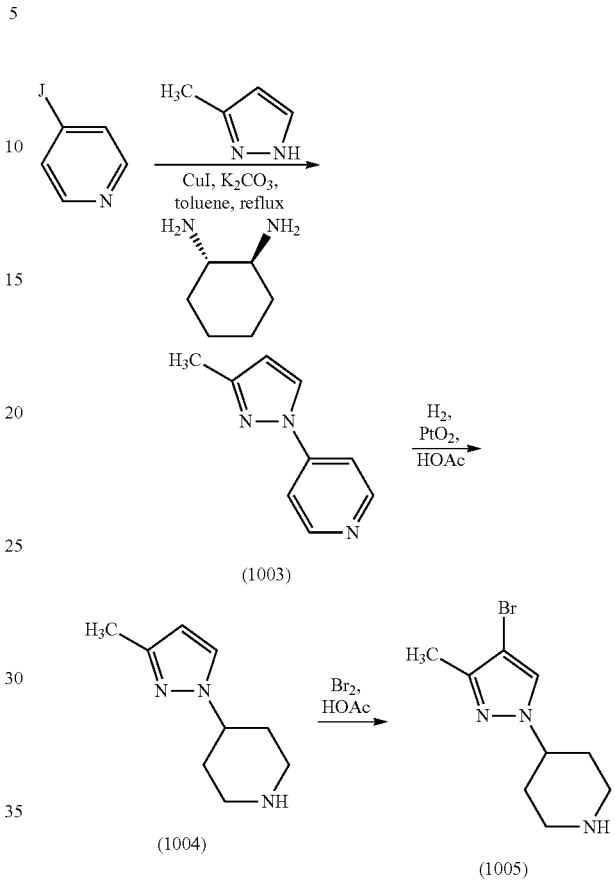

N-Boc-4-hydroxypiperidine (30 g, 149.1 mmol, 1 eq.), triethyl amine (22.87 mL, 164 mmol, 1.1 eq.) and N,N-dimethylpyridin-4-amine (DMAP) (1.83 g, 14.98 mmol, 0.1 eq.) were dissolved in anhydrous methylene chloride (500 mL) and cooled to 0° C. in an ice bath. Methanesulfonyl chloride (12.12 mL, 156.6 mmol, 1.05 eq.) was added dropwise. Upon completion of the addition, the reaction was allowed to warm to room temperature and stirred overnight. The reaction was washed with water (3×100 mL), then saturated sodium bicarbonate (3×100 mL), extracted with additional methylene chloride, dried ($Na_2SO_4$) and concentrated to give 40.83 g (146.2 mmol) of 1-(tert-butoxycarbonyl)piperidin-4-yl methanesulfonate (Compound 1001, 98% yield), an off white solid that was used without further purification.

To a solution of 4-bromopyrazole (4.68 g, 31.83 mmol) in DMF (300 mL) at 0° C. was added sodium hydride (60% on mineral oil, 1.27 g, 31.83 mmol). The solution was allowed to stir at 0° C. for one hour, at which point a solution of Compound 1001 (9.78 g, 31.83 mmol) in DMF (50 mL) was added dropwise. The reaction mixture was allowed to stir at room temperature for 1 hour before refluxing overnight. Disappearance of both starting materials was tracked by TLC (1:1 Hexanes/Ethyl Acetate). The reaction was cooled to room temperature and quenched by addition of aqueous NaCl (300 mL), extracted with ethyl acetate (3×200 mL), washed with 1% aqueous LiCl (3×200 mL), dried and concentrated in vacuo. The resulting crude bromide was purified by silica gel chromatography (0-25% Ethyl Acetate in Hexanes) to give Compound 1002.

4-Iodopyridine (15 g, 73.17 mmol, 1 eq.), copper (I) iodide (696.7 mg, 3.66 mmol, 0.05 eq.), and $K_2CO_3$ (21.24 g, 153.7 mmol, 2.1 eq.) were combined and evacuated and purged with $N_2$ three times. Anhydrous toluene (75 mL) was added, followed by the addition of trans-1,2-diaminocyclohexane (1.76 mL, 14.63 mmol, 0.2 eq.) and 3-methyl-1H-pyrazole (6.6 g, 80.49 mmol, 1.1 eq.). The reaction was sealed and stirred at 110° C. overnight, then cooled and filtered through florisil, eluting with ethyl acetate. The combined fractions were concentrated and the product was recrystallized from ether and hexanes to give 10.5 g (65.96 mmol) of 4-(3-methyl-1H-pyrazol-1-yl)pyridine (Compound 1003, 90% yield %); $^1$H NMR (300 MHz, $CDCl_3$): δ 8.1 (m, 2H), 7.94 (d, J=2.5 Hz, 1H), 7.65 (m, 2H), 6.35 (d, J=2.5 Hz, 1H), 2.38 (s, 3H).

To Compound 1003 (1.0 g, 6.3 mmol, 1 eq.) was added a solution of dry $PtO_2$ (286 mg, 1.26 mmol, 0.2 eq.) in acetic acid. The reaction was hydrogenated at 50 psi overnight. The acetic acid was decanted and the catalyst was washed with additional acetic acid. The combined fractions containing product were concentrated to give 1.0 g (6.05 mmol) of 4-(3-methyl-1H-pyrazol-1-yl)piperidine (Compound 1004, 96% yield); $^1$H NMR (300 MHz, DMSO-$d_6$): δ 7.6 (d, J=1.9 Hz, 1H), 6.0 (d, J=1.9 Hz, 1H), 4.13 (m, 1H), 3.1 (m, 2H), 2.9 (m, 1H), 2.65 (m, 2H), 2.14 (s, 3H), 2.0-1.5 (m, 4H).

To Compound 1004 (as the HCl salt, 1.0 g, 4.958 mmol, 1 eq.) in glacial acetic acid (5 mL) was added $Br_2$ (0.281 mL, 5.45 mmol, 1.1 eq.) in acetic acid (5 mL) dropwise. The reaction was refluxed for 2 hours then cooled to room temperature. The resulting solid was filtered and dried in vacuo to give 1.2 g (3.69 mmol) of 4-(4-bromo-3-methyl-1H-pyrazol-1-yl)piperidine (Compound 1005, 74% yield) as the HBr salt; $^1$H NMR (300 MHz, DMSO-$d_6$): δ 8.69 (bs, 1H), 8.56 (bs, 1H), 7.94 (s, 1H), 4.45-4.35 (m, 1H), 3.36 (m, 2H), 3.03 (m, 2H), 2.13 (s, 3H), 2.04 (m, 4H).

Example 3 tert-Butyl 4-(4-bromo-3-(trifluoromethyl)-1H-pyrazol-1-yl)piperidine-1-carboxylate

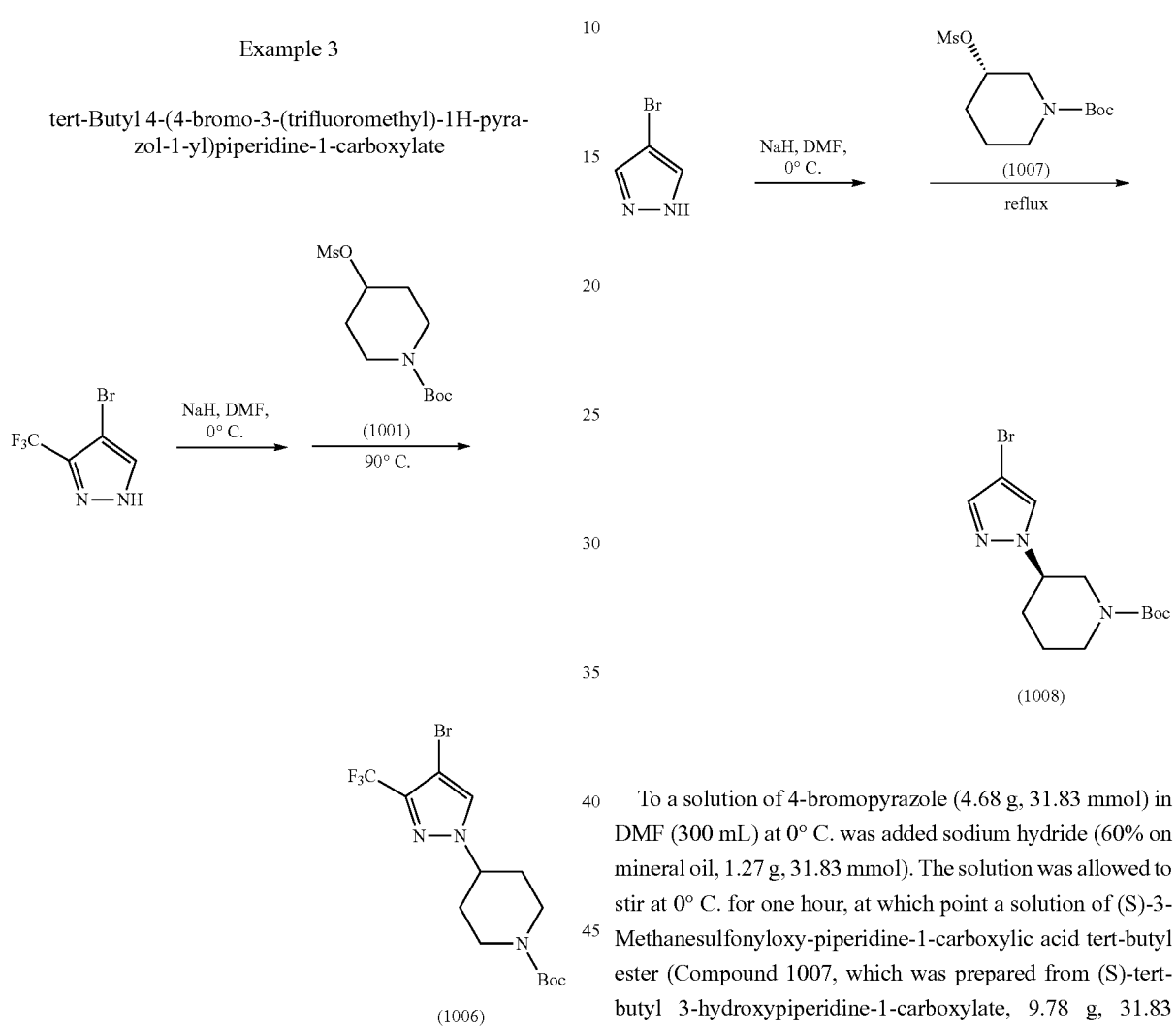

4-Bromo-3-(trifluoromethyl)-1H-pyrazole (0.96 g, 4.47 mmol, 1 eq.), was diluted in anhydrous DMF (10 mL) and cooled to 0° C. in an ice bath. NaH (60% in mineral oil, 230 mg, 5.75 mmol, 1.29 eq.) was added slowly and the suspension was stirred at 0° C. for 1 hour. tert-Butyl 4-(methylsulfonyloxy)piperidine-1-carboxylate (Compound 1001, 1.38 g, 4.94 mmol, 1.1 eq.) was diluted in DMF (3 mL) and added to the cooled mixture. The reaction was stirred at 90° C. overnight. After cooling, the reaction was poured into water (20 mL) and extracted with ethyl acetate (3×50 mL). The combined organic layers were washed with brine (3×30 mL), dried (Na$_2$SO$_4$), and concentrated. The resulting oil was purified via silica gel chromatography eluting with hexanes:ethyl acetate to give 1.23 g (3.09 mmol) of tert-Butyl 4-(4-bromo-3-(trifluoromethyl)-1H-pyrazol-1-yl)piperidine-1-carboxylate (Compound 1006, 69% yield %); $^1$H NMR (300 MHz, CDCl$_3$): δ 7.52 (s, 1H), 4.45-4.2 (m, 3H), 2.85 (m, 2H), 2.15 (m, 2H), 1.9 (m, 1H), 1.45 (m, 9H).

Example 4

(R)-tert-butyl 3-(4-bromo-1H-pyrazol-1-yl)piperidine-1-carboxylate

To a solution of 4-bromopyrazole (4.68 g, 31.83 mmol) in DMF (300 mL) at 0° C. was added sodium hydride (60% on mineral oil, 1.27 g, 31.83 mmol). The solution was allowed to stir at 0° C. for one hour, at which point a solution of (S)-3-Methanesulfonyloxy-piperidine-1-carboxylic acid tert-butyl ester (Compound 1007, which was prepared from (S)-tert-butyl 3-hydroxypiperidine-1-carboxylate, 9.78 g, 31.83 mmol) in DMF (50 mL) was added dropwise. The reaction mixture was allowed to stir at room temperature for 1 hour before refluxing overnight. Disappearance of both starting materials was tracked by TLC (1:1 Hexanes/Ethyl Acetate). The reaction was cooled to room temperature and quenched by addition of aqueous NaCl (300 mL), extracted with ethyl acetate (3×200 mL), washed with 1% aqueous LiCl (200 mL×3), dried and concentrated in vacuo. The resulting crude bromide (Compound 1008) was purified by silica gel chromatography (0-25% Ethyl Acetate in Hexanes) to give (R)-tert-butyl 3-(4-bromo-1H-pyrazol-1-yl)piperidine-1-carboxylate as a colourless waxy solid (4.54 g, 43% yield); $^1$H NMR (300.0 MHz, CDCl$_3$): δ 7.42 (s, 1H), 7.40 (s, 1H), 4.13-4.05 (m, 2H), 3.82 (d, J=13.2 Hz, 1H), 3.20 (dd, J=10.3, 14.0 Hz, 1H), 2.94-2.85 (m, 1H), 2.08-1.97 (m, 2H), 1.74-1.45 (m, 2H) and 1.39 (s, 9H) ppm.

Example 5 tert-Butyl 3-(4-Iodo-pyrazol-1-yl)-8-aza-bicyclo[3.2.1]octane-8-carboxylate (endo and exo isomers, Compounds 1012 and 1013, respectively)

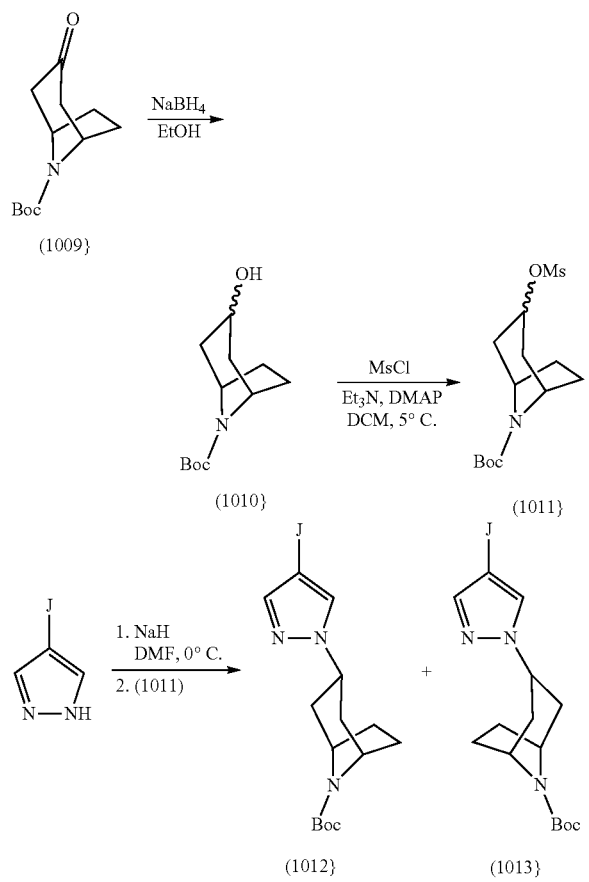

3-Oxo-8-aza-bicyclo[3.2.1]octane-8-carboxylic acid tert-butyl ester (Compound 1009, 8 g, 35.5 mmol) was dissolved in 100 mL of ethanol. Sodium borohydride (2 g, 53.5 mmol) was added to the solution portionwise at room temperature. After stirring for 3 hours, the reaction was evaporated in vacuo to give clear viscous oil. The oil was dissolved in dichloromethane, washed with water and brine, dried over anhydrous sodium sulfate, filtered and evaporated to afford 7.55 g of 3-hydroxy-8-aza-bicyclo[3.2.1]octane-8-carboxylic acid tert-butyl ester (Compound 1010) as a white crystalline solid; $^1$H NMR (300 MHz, DMSO-$d_6$): δ 4.23 (dd, J=2.7, 4.6 Hz, 1H), 4.18-4.06 (m, 2H), 2.17-2.06 (m, 1H), 1.99-1.91 (m, 3H), 1.72-1.50 (m, 5H), 1.47 (s, 9H).

Compound 1010 (7.55 g, 33.2 mmol), triethylamine (5.1 mL, 37 mmol), and 4-dimethylaminopyridine (36 mg, 0.3 mmol) were taken into 100 mL of dichloromethane and cooled to 5° C. in an ice bath. Methanesulfonyl chloride (2.6 mL, 33.2 mmol) was added to the solution dropwise and the reaction warmed to room temperature and stirred at room temperature for 18 hours. The reaction was washed with water and brine, dried over anhydrous sodium sulfate, and the solvent removed under reduced pressure to afford 10.2 g of 3-methanesulfonyloxy-8-aza-bicyclo[3.2.1]octane-8-carboxylic acid tert-butyl ester as a mixture of isomers (Compound 1011) as a clear yellow oil; $^1$H NMR (300 MHz, DMSO-$d_6$): δ 5.09-5.01 (m, 1H), 4.28 (s, 1H), 4.22 (s, 1H), 3.01 (s, 3H), 2.20-1.97 (m, 6H), 1.71-1.66 (m, 2H), 1.46 (s, 9H). This compound was used without further purification.

Sodium hydride (60% in mineral oil) (1.52 g, 38 mmol) was added slowly to a cooled solution (0° C.) of 4-iodopyrazole (6.6 g, 34 mmol) in anhydrous DMF (75 mL). After stirring for 1 hour, a solution of (3-methanesulfonyloxy-8-aza-bicyclo[3.2.1]octane-8-carboxylic acid tert-butyl ester (Compound 1011, 10.2 g, 34 mmol) in 25 mL of anhydrous DMF was added to the reaction. The reaction was heated to 100° C. for 18 hours. After cooling, the reaction was poured into 50 mL of water and extracted with ethyl acetate. The combined ethyl acetate extracts were washed with water (2×50 mL) and brine (2×50 mL), dried over anhydrous sodium sulfate, and the volatiles removed under reduced pressure to give 12.82 g of title compounds 1012 and 1013, as a mixture of endo and exo isomers. A 4 g portion of the crude material was purified by medium pressure silica gel chromatography, eluting with a 0%-10% ethyl acetate in hexane gradient over 30 minutes, to afford 1.5 g of the endo isomer as the first eluting compound and 1.3 g of the exo isomer as the second eluting compound; $^1$H NMR (300 MHz, DMSO-$d_6$) endo isomer: δ 7.58 (s, 1H), 7.52 (s, 1H), 7.26 (s, 1H), 4.34 (q, J=5.3 Hz, 1H), 4.27 (s, 2H), 2.44 (s, 4H), 1.89-1.85 (m, 2H), 1.60-1.53 (m, 2H), 1.49 (s, 9H), exo isomer: δ 7.48 (d, J=0.4 Hz, 1H), 7.41 (s, 1H), 7.26 (s, 1H), 4.68 (m, 1H), 4.37 (br s, 2H), 2.08-2.05 (m, 6H), 1.79-1.75 (m, 2H), 1.49 (s, 9H).

Example 6 tert-Butyl 4-(4-bromo-3-methyl-1H-pyrazol-1-yl)azepane-1-carboxylate

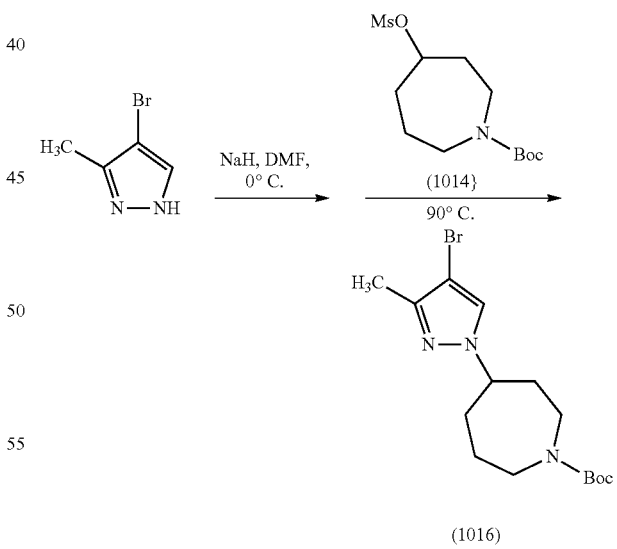

4-Bromo-3-methyl-1H-pyrazole (1.0 g, 6.25 mmol, 1 eq.) was diluted in DMF (10 mL) and cooled to 0° C. NaH (60% in mineral oil, 275 mg, 6.87 mmol, 1.1 eq.) was added slowly and stirred at 0° C. for 1 hour. tert-Butyl 4-(methylsulfonyloxy)azepane-1-carboxylate (Compound 1014, 1.85 g, 6.3 mmol, 1.01 eq.) was diluted in DMF (2.5 mL) and added to the mixture and the reaction was heated to 90° C. overnight.

After cooling, the reaction was poured into water (20 mL) and extracted with ethyl acetate (3×50 mL). The combined organic layers were washed with brine (3×30 mL), dried (Na$_2$SO$_4$), and concentrated. The oil was purified by silica gel chromatography eluting with hexanes:ethyl acetate to give 0.59 g of tert-Butyl 4-(4-bromo-3-methyl-1H-pyrazol-1-yl) azepane-1-carboxylate (Compound 1016, 1.65 mmol, 26% yield); $^1$H NMR (300 MHz, CDCl$_3$): δ 7.33 (s, 1H), 4.12 (m, 1H), 3.8-3.2 (m, 4H), 2.22 (s, 3H), 2.18-1.8 (m, 4H), 1.75-1.55 (m, 2H), 1.49 (m, 9H).

Example 7

(3aR,6aS)-tert-butyl5-(4-iodo-1H-pyrazol-1-yl) hexahydrocyclopenta[c]pyrrole-2(1H)-carboxylate

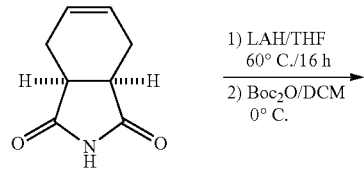

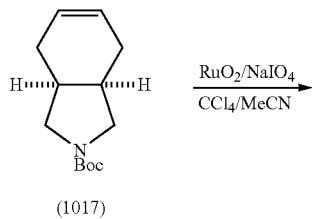

(1017)

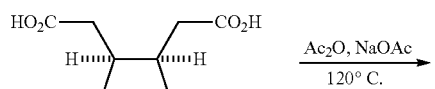

(1018)

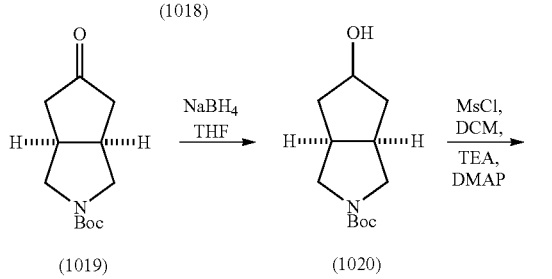

(1019)      (1020)

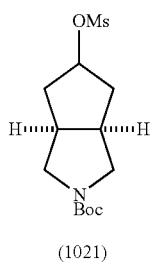

(1021)

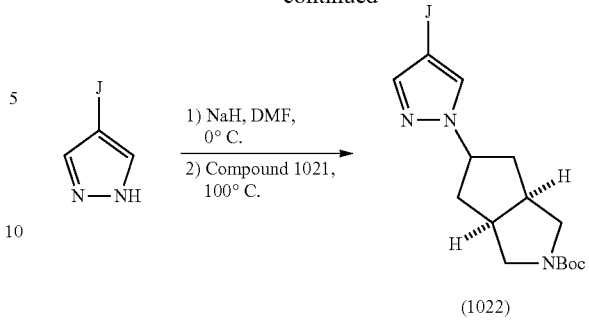

(1022)

To a solution of 1 M LAH in THF (800 mL; 0.8 mole; 2.3 eq) at rt was added, portionwise, tetrahydrophthalimide (52.6 g; 0.348 mole; 1 eq). The reaction mixture was stirred at 60° C. for 16 hours, then cooled to RT and quenched carefully with sequential addition of 30 mL of water, 30 mL of THF, 15% aqueous KOH (30 mL), and water (100 mL). The mixture was diluted with 135 mL of ether, stirred at RT for 1 hour, and filtered through a pad of diatomaceous earth on a 600 mL fritted glass filter funnel, washing the pad with 400 mL of DCM. The filtrate was concentrated in vacuo to yield (3aR, 7aS)-2,3,3a,4,7,7a-hexahydro-1H-isoindole as an oil, which was used directly in the next reaction as is.

Accordingly, the crude isoindole (38.9 g; 0.313 mole; 1 eq) in 400 mL of dry DCM at 0° C. was treated with Boc anhydride (103 g; 0.470 mole; 1.5 eq). The reaction mixture was stirred at 0° C. for 30 minutes and then at RT for 16 hours. The reaction was concentrated in vacuo to an oil, which was dissolved in 800 mL of ether, washed with 1 M citric acid (2×170 mL), water, satd' NaHCO$_3$, and brine. The organics were dried with sodium sulfate and concentrated in vacuo to an oil that was purified by passing it through a short plug of silica gel, eluting with 15% EtOAc/hexanes, to give (3aR, 7aS)-tert-butyl 3a,4,7,7a-tetrahydro-1H-isoindole-2(3H)-carboxylate (Compound 1017, 69 g, 80% yield for 2 steps); $^1$H NMR (CDCl$_3$): δ 5.7 (s, 2H), 3.45 (m, 2H), 3.15 (m, 2H), 2.3 (m, 4H), 1.9 (m, 2H), 1.5 (s, 9H).

Compound 1017 (32.6 g; 0.146 mole; 1 eq) in carbon tetrachloride (320 mL), acetonitrile (320 mL), and water (500 mL) was treated with sodium metaperiodate (124.9 g; 0.588 mole; 4 eq) followed by treatment with catalytic ruthenium oxide hydrate (778 mg; 5.8 mmole; 0.04 eq). The mixture was stirred vigourously for 24 hours at RT, diluted with DCM (450 mL) and water (80 mL), and filtered through a pad of diatomaceous earth. The filtrate was passed through a small plug of silica, using DCM as the eluent, and concentrated in vacuo to yield 2,2'-((3S,4R)-1-(tert-butoxycarbonyl)pyrrolidine-3,4-diyl)diacetic acid (Compound 1018, 33.18 g; 80% yield); $^1$H NMR (CDCl$_3$): δ 3.55 (m, 2H), 3.15 (m, 2H), 2.8 (m, 2H), 2.45 (m, 4H), 1.5 (s, 9H).

Compound 1018 (33.18 g; 0.115 mole) in 202 mL of acetic anhydride was treated with sodium acetate (0.093 mole). The reaction mixture was stirred at 120° C. for 3 hours then cooled to RT and filtered. The filtered material was washed with ether (2×200 mL) and the filtrate was evaporated in vacuo. The residue was purified by silica gel chromatography (30% EtOAc/hexanes) to provide (3aR,6aS)-tert-butyl 5-oxo-hexahydrocyclopenta[c]pyrrole-2(1H)-carboxylate (Compound 1019, 13.8 g, 55% yield); $^1$H NMR (CDCl$_3$): δ 3.7 (m, 2H), 3.25 (m, 2H), 2.9 (m, 2H), 2.5 (dd, 2H), 2.2 (dd, 2H), 1.5 (s, 9H).

Compound 1019 (4 g; 0.018 mole) was dissolved in 50 mL of ethanol. Sodium borohydride was added at RT portionwise. After stirring for 3 hours, the reaction was concentrated in vacuo. The resulting oil was dissolved in DCM (200 mL), washed with water, brine, (Na$_2$SO$_4$), and concentrated in vacuo to yield (3aR,6aS)-tert-butyl 5-hydroxyhexahydrocyclopenta[c]pyrrole-2(1H)-carboxylate as a yellow oil (Compound 1020, 3.79 g; 93% yield); $^1$H NMR (CDCl$_3$): δ 4.2 (m, 1H), 3.55 (dd, 2H), 3.4 (dd, 2H), 2.7 (m, 2H), 2.2 (m, 2H), 1.6 (m, 2H), 1.5 (s, 9H).

Compound 1020 (3.79 g; 0.0168 mole; 1 eq), TEA (0.0187 mole; 1.11 eq), and DMAP (20 mg; 0.168 mmole; 0.01 eq) were dissolved in 50 mL of dry DCM and cooled to 0° C. with an ice bath. Mesyl chloride (1.31 mL; 0.0168 mol; 1 eq) was slowly added to the solution dropwise and the reaction mixture stirred at RT for 16 hours. The reaction mixture was washed with water and brine, dried (Na$_2$SO$_4$), and concentrated in vacuo to yield (3aR,6aS)-2-(tert-butoxycarbonyl)-octahydrocyclopenta[c]pyrrol-5-yl methanesulfonate (Compound 1021) as an oil, which was used directly in the next step as is.

Sodium hydride (60% in mineral oil, 740 mg; 0.184 mole; 1.1 eq) was added slowly to a cooled 0° C. solution of 4-iodopyrazole (3.26 g; 0.0168 mole; 1 eq) in 38 mL of dry DMF. The mixture was stirred at 0° C. for 1 hour and then a solution of Compound 1021 (5.13 g; 0.0168 mole; 1 eq) in 12 mL of DMF was added. The reaction was heated at 100° C. for 6 h. The reaction mixture was diluted with ethyl acetate (200 mL) and washed with water, then brine. The organic phase was dried (Na$_2$SO$_4$), concentrated in vacuo, and purified by medium pressure silica gel chromatography (25%-40% EtOAc/hexanes) to provide (3aR,6aS)-tert-butyl5-(4-iodo-1H-pyrazol-1-yl)hexahydrocyclopenta[c]pyrrole-2(1H)-carboxylate (Compound 1022, 5.51 g, 60% yield); $^1$H NMR (CDCl$_3$): δ 7.5 (s, 1H), 7.4 (s, 1H), 4.9 (m, 1H), 3.7 (m, 2H), 3.2 (m, 2H), 2.9 (m, 2H), 2.4 (m, 2H), 2.2 (m, 2H), 1.5 (s, 9H).

Example 8

Ethyl 2-bromo-4,5,7,8-tetrahydrothieno[3,2-d]azepine-6-carboxylate

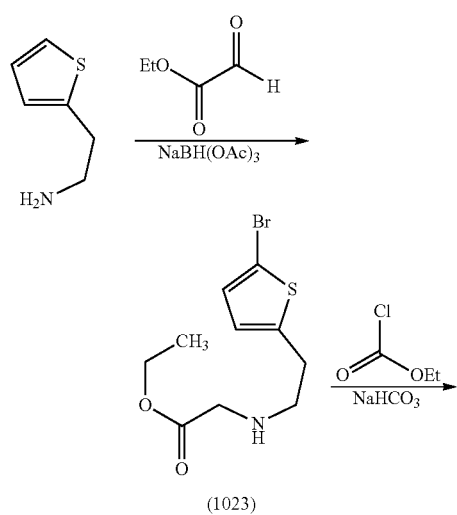

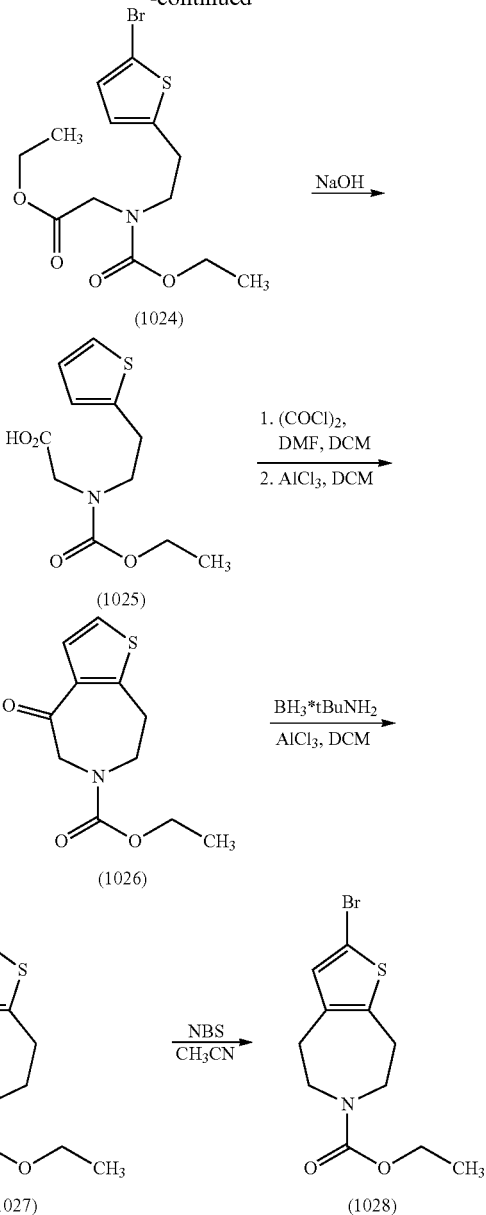

To a solution of 2-(thiophen-2-yl)ethanamine (20 g, 157.4 mmol) in CH$_2$Cl$_2$ at 0° C. was added ethyl glyoxylate followed by acetic acid (4 mL). The reaction mixture stirred for 15 minutes followed by the addition of NaBH(OAc)$_3$ (40 g, 204.7 mmol) in portions. The reaction mixture was stirred for an additional 1 hour and 7 mL of acetic acid was added. The reaction was warmed to RT and stirred until complete consumption of 2-(thiophen-2-yl)ethanamine was observed. The reaction mixture was concentrated in vacuo to yield compound 1023, which was taken up in THF (500 mL) and treated with solid NaHCO$_3$ (40 g, 472.2 mmol) at 0° C. This was followed by addition of ethyl chloroformate (19.5 mL, 157 mmol) and the slow addition of a saturated aq. NaHCO$_3$ solution until the gas evolution was minimal. The reaction mixture was stirred overnight and extracted with ethyl acetate. The combined organics were washed with brine solution and concentrated to obtain crude product, which was purified by silica gel chromatography to yield ethyl (ethoxycarbonyl)methyl2-(5-bromothiophen-2-yl)ethylcarbamate (Compound 1023, 15.0 g, 34% yield); ES-MS: 286.2 (M+H).

To solution of Compound 1024 (30.0 g, 105.26 mmol) in ethanol at 0° C. was added dropwise 200 mL of 1N NaOH. The reaction mixture was warmed to RT and stirred for 24 hours. The reaction mixture was extracted with $Et_2O$ to remove unreacted starting material and the aqueous layer acidified with 1N HCl until a pH of 1 was achieved. The aqueous solution was extracted with ethyl acetate (2×500 mL) and the combined organics were washed with brine solution, dried ($Na_2SO_4$), filtered, and the volatiles removed under reduced pressure to obtain crude product, which was washed with pentane to provide 2-(N-(Ethoxycarbonyl)-N-(2-(thiophen-2-yl)ethyl)amino)acetic acid (Compound 1025, 74% yield) as a colorless solid; ES-MS: 258.2 (M+H).

Compound 1025 (14 g, 54.41 mmol) was dissolved in dry dichloromethane (300 mL). To this suspension was added 0.1 mL of DMF, followed by the careful addition of oxayl chloride (10.4 g, 81.93 mmol). The reaction mixture was stirred at room temperature for 1 hour, at which time 0.5 mL of additional oxalyl chloride was added. The solvent was evaporated under vacuum to give 2-(N-(ethoxycarbonyl)-N-(2-(thiophen-2-yl)ethyl)amino)acetyl chloride. This acid chloride was re-dissolved in dry DCM (300 mL) and $AlCl_3$ (18.1 g, 135.74 mmol) was added at room temperature. The reaction was kept at room temperature for 1 hour then quenched by the slow addition of ethanol (about 10 mL). The mixture was then poured into ice and stirred for 1 hr. The aqueous mixture was extracted with DCM (3×150 mL). The combined organic layers were dried over $MgSO_4$, filtered, and the volatiles removed under reduced pressure to give a residue, which was purified by silica gel chromatography to produce ethyl 4,5,7,8-tetrahydro-4-oxothieno[3,2-d]azepine-6-carboxylate (Compound 1026, 7.4 g, 30.92 mmol).

A suspension of $AlCl_3$ (6.7 g, 50.25 mmol) in dry DCM (60 mL) was cooled to 0° C. and $BH_3.tBuNH_2$ solid (8.7 g, 100 mmol) was added. After stirring at 0° C. for 5 min, a solution of Compound 1026 (4 g, 16.72 mmol) in DCM was added. The reaction was stirred at room temperature for 14 hours, monitoring the progress by TLC. The mixture was carefully quenched by the addition of 2N HCl (gas evolution observed). When gas evolution ceased, more 2N HCl was added, and the mixture extracted with DCM (3×100 mL). The combined DCM layers were dried over $MgSO_4$, filtered, and the filtrate evaporated under vacuum to afford ethyl 4,5,7,8-tetrahydrothieno[3,2-c]azepine-6-carboxylate (Compound 1027) as a white solid. This product was used directly without purification in subsequent reactions.

Compound 1027 (16.72 mmol) was dissolved in $CH_3CN$ (150 mL) and NBS (4.74 g, 26.63 mmol) was added. The reaction was stirred at room temperature for 30 min, and poured into a solution of $Na_2SO_3$ (200 mL)/6N NaOH (5 mL). The aqueous layer was extracted with EtOAc (3×150 mL), dried over $MgSO_4$, filtered, and the volatiles removed under reduced pressure. The residue was purified by silica gel chromatography to provide ethyl 2-(2-bromo-4,5,7,8-tetrahydrothieno[3,2-d]azepin-6-yl)acetate (Compound 1028, 3.1 g, 10.20 mmol).

The same procedure was used with 1-(thiophen-2-yl)propan-2-amine as the starting material to produce ethyl 2-bromo-4,5,7,8-tetrahydro-7-methylthieno[3,2-c]azepine-6-carboxylate (Compound 1029).

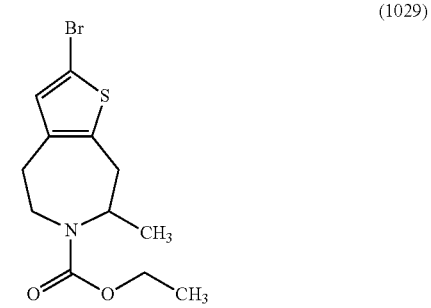 [SMILES: CCOC(=O)N1CCc2cc(Br)sc2CC1C]

(1029)

Example 9

Ethyl 2-bromo-4,5,7,8-tetrahydro-4-methylthieno[3,2-c]azepine-6-carboxylate

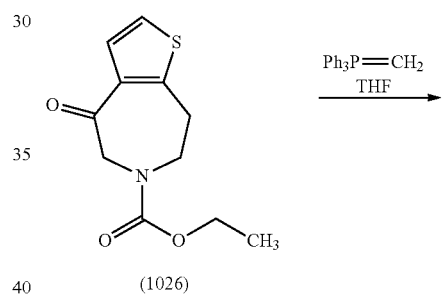

(1026)

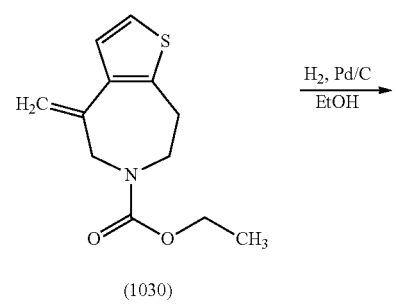

(1030)

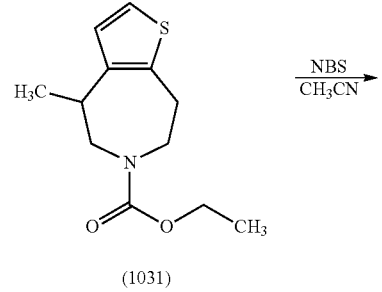

(1031)

-continued

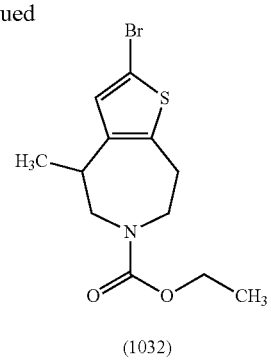

(1032)

A suspension of methyl(triphenylphosphinium) bromide (1 g, 2.8 mmol) in anhydrous THF (10 mL) was cooled to 0° C. To this suspension was added potassium hexamethyldisilazide (KHMDS, 520 mg, 2.6 mmol). The mixture was stirred at 0° C. for 30 min, Compound 1026 (480 mg, 2.0 mmol) was added, and the reaction warmed up to RT and stirred for another 1 hour. The solvent was removed under reduced pressure and the residue was purified by medium pressure silica gel chromatography to give ethyl 4-methylene-7,8-dihydro-4H-thieno[2,3-d]azepine-6(5H)-carboxylate (Compound 1030, 310 mg, 65% yield) as an oil; $^1$H NMR (300 MHz, CDCl$_3$): δ 6.90 (s, 2H), 5.17-5.02 (m, 2H), 4.12 (d, J=22.3 Hz, 2H), 4.02 (q, J=7.1 Hz, 2H), 3.65-3.58 (m, 2H), 2.97-2.94 (m, 2H), 1.13 (t, J=7.1 Hz, 3H).

Compound 1030 (310 mg, 1.31 mmol) was dissolved in ethanol (50 mL). The solution was degassed three times before addition of 10% Pd/C (100 mg). The flask was charged with hydrogen at atmospheric pressure (H$_2$ balloon) and stirred at RT for 14 hours. The catalyst was removed by filtration through diatomaceous earth and the volatiles removed under reduced pressure to yield ethyl 4,5,7,8-tetrahydro-4-methylthieno[3,2-d]azepine-6-carboxylate (Compound 1031), which was used in subsequent reactions without further purification.

To a solution of Compound 1031 in acetonitrile (30 mL) was added NBS (233 mg, 1.31 mmol). The reaction mixture was stirred at RT for 30 min and quenched by the addition of an aqueous solution of Na$_2$SO$_3$ and saturated NaHCO$_3$ solution. The aqueous layer was extracted with EtOAc. After drying over MgSO$_4$, the organics were concentrated in vacuo. The residue was purified by medium pressure silica gel chromatography to give ethyl 2-bromo-4-methyl-7,8-dihydro-4H-thieno[2,3-d]azepine-6(5H)-carboxylate (Compound 1032, 280 mg, 0.88 mmol, 67%); $^1$H NMR (300.0 MHz, CDCl$_3$): δ 6.82 (s, 1H), 4.18 (q, J=7.0 Hz, 2H), 3.71-3.47 (m, 4H), 3.10-2.90 (m, 3H) and 1.28 (t, J=7.1 Hz, 3H).

Example 10

Ethyl 2-bromo-4,5,7,8-tetrahydro-4,4-dimethylthieno[3,2-d]azepine-6-carboxylate

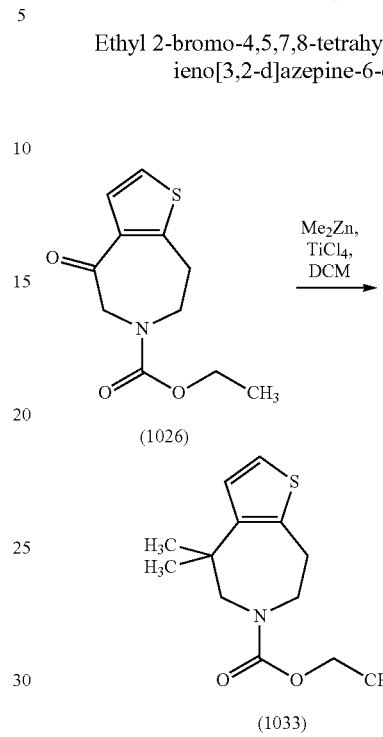

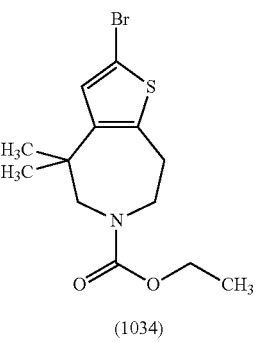

(1034)

To anhydrous DCM (100 mL) at −78° C. was added TiCl$_4$ (4.76 g, 25.1 mmol) and Me$_2$Zn (2.0 M in PhMe, 13 mL, 26.0 mmol). The resulting mixture was stirred at −78° C. for 5 minutes, then a solution of ethyl 4-oxo-7,8-dihydro-4H-thieno[2,3-d]azepine-6-carboxylate (1 g, 4.18 mmol) in DCM (10 mL) was slowly added. After the addition, the reaction was allowed to warm up to RT and stirred for 3 hours. The solution was then carefully poured into an iced-water and extracted with DCM. The combined organic layers were dried over MgSO$_4$ and the volatiles removed under reduced pressure. The crude residue, which contained Compound 1033, was dissolved in acetonitrile (100 mL). To this solution was added NBS (0.82 g, 4.61 mmol). The reaction mixture was stirred at RT for 1 h and quenched by addition of aqueous solution of Na$_2$SO$_3$ and saturated NaHCO$_3$ solution. The aqueous solution was extracted with EtOAc, the organics dried over MgSO4, and the volatiles removed under reduced pressure. The residue was purified by medium pressure silica gel chromatography to give ethyl 2-bromo-4,4-dimethyl-7,8-dihydro-4H-thieno[2,3-d]azepine-6-carboxylate (Compound 1034, 1 g, 3.0 mmol, 72% yield); LCMS (M+H)

=332.0; ¹H NMR (300.0 MHz, CDCl₃): δ 6.87 (s, 1H), 4.19 (q, J=6.6 Hz, 2H), 3.67-3.58 (m, 2H), 3.58 (s, 1H), 3.51 (s, 1H), 2.93 (m, 2H) and 1.30 (t, J=7.1 Hz, 3H) ppm.

Example 11

Ethyl 2-bromo-7-ethyl-4,5,7,8-tetrahydrothieno[3,2-d]azepine-6-carboxylate

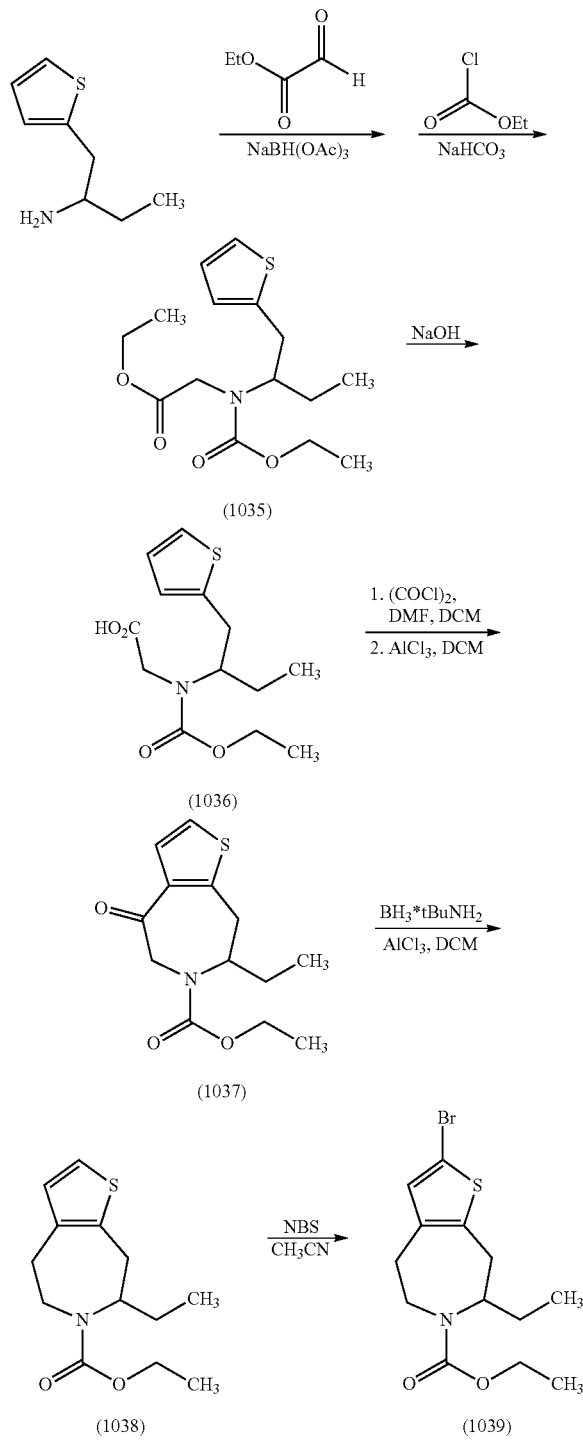

To a solution of 1-(thiophen-2-yl)butan-2-amine (2.1 g, 13.72 mmol) in methylene chloride (40 mL) was added ethyl glyoxylate (2.80 g, 13.72 mmol) at RT. One drop of acetic acid was added, the mixture stirred at RT for 75 min, and sodium triacetoxyborohydride (4.36 g, 20.58 mmol) was added. The reaction was stirred at RT for 15 hours before quenching the reaction by adding 5 mL of acetic acid. The volatiles were removed under reduced pressure and the residue dissolved in 40 mL THF. Saturated sodium bicarbonate (40 mL) was added carefully, followed by the addition of ethyl chloroformate (2.978 g, 2.624 mL, 27.44 mmol). Solid NaHCO₃ was subsequently added portionwise until gas evolution ceased. The reaction was stirred at RT overnight and extracted with EtOAc (2×). The organics were dried over Na₂SO₄, the volatiles removed under reduced pressure, and there resulting yellow oil purified by silica gel chromatography, using a 0-35% EtOAc/hexanes gradient as eluant, to produce ethyl 2-(ethoxycarbonyl-(1-(thiophen-2-yl)butan-2-yl)amino)acetate (Compound 1035, 3.03 g) as a colorless oil.

A solution of Compound 1035 (3.03 g, 9.668 mmol) in EtOH (50 mL) was treated with 1 M NaOH (48 mL) at RT overnight. The reaction mixture was diluted with 50 mL 1 M NaOH and 100 mL water, washed with EtOAc, and the aqueous layer was acidified with 6M HCl (30 mL) and extracted with EtOAc (2×). The organics were dried over Na₂SO₄, and the volatiles were evaporated under vacuum to give 2.23 g of (ethoxycarbonyl-(1-thiophen-2-ylmethyl-propyl)-amino)-acetic acid (Compound 1036).

To a solution of Compound 1036 (2.25 g, 7.885 mmol) in DCM (35 mL) was added 0.1 mL of DMF followed by addition of oxalyl chloride (1.502 g, 1.032 mL, 11.83 mmol). The reaction mixture was stirred at RT for 1 hour and the volatiles were removed in vacuo. The residue was taken up in benzene and the volatiles were again removed in vacuo (2×), followed by drying under vacuum. The residue was taken up in dry DCM (35 mL) and AlCl₃ (3.679 g, 27.59 mmol) was added at RT. The mixture was stirred at RT for 1.5 hours and the reaction quenched with ethanol. The resulting solution was poured into ice water and extracted with DCM (2×). The combined organic layers were dried over Na₂SO₄, concentrated under vacuum, and the residue purified by silica gel chromatography, using a 5%-20% ethyl acetate/hexanes gradient as eluant, to produce ethyl 7-ethyl-4-oxo-7,8-dihydro-4H-thieno[2,3-d]azepine-6(5H)-carboxylate (Compound 1037, 671 mg).

Aluminum chloride (972.2 mg, 7.291 mmol) was added to DCM (60 mL) at 0° C., followed by addition of borane-tert-butylamine complex (1.268 g, 14.58 mmol). To the mixture was added a solution of Compound 1037 (650 mg, 2.431 mmol) in DCM (5 mL). The reaction was allowed to warm up to RT and stirred for 18 hours, followed by quenching the reaction with 2N HCl solution until gas evolution ceased. The mixture was extracted with DCM, dried over Na₂SO₄, and the volatiles removed under reduced pressure. The resulting residue (Compound 1038) was dissolved in acetonitrile and N-Bromosuccinamide (432.7 mg, 2.431 mmol) was added dropwise. The reaction mixture was stirred at RT for 1 hour, then concentrated under vacuum. The residue was purified by silica gel chromatography, using a 0-20% EtOAC/hexanes gradient as eluant, to give ethyl 2-bromo-7-ethyl-7,8-dihydro-4H-thieno[2,3-d]azepine-6(5H)-carboxylate (Compound 1039, 300 mg).

Example 12

Ethyl 2-bromo-5,6-dihydro-4H-thieno[2,3-c]azepine-7(8H)-carboxylate

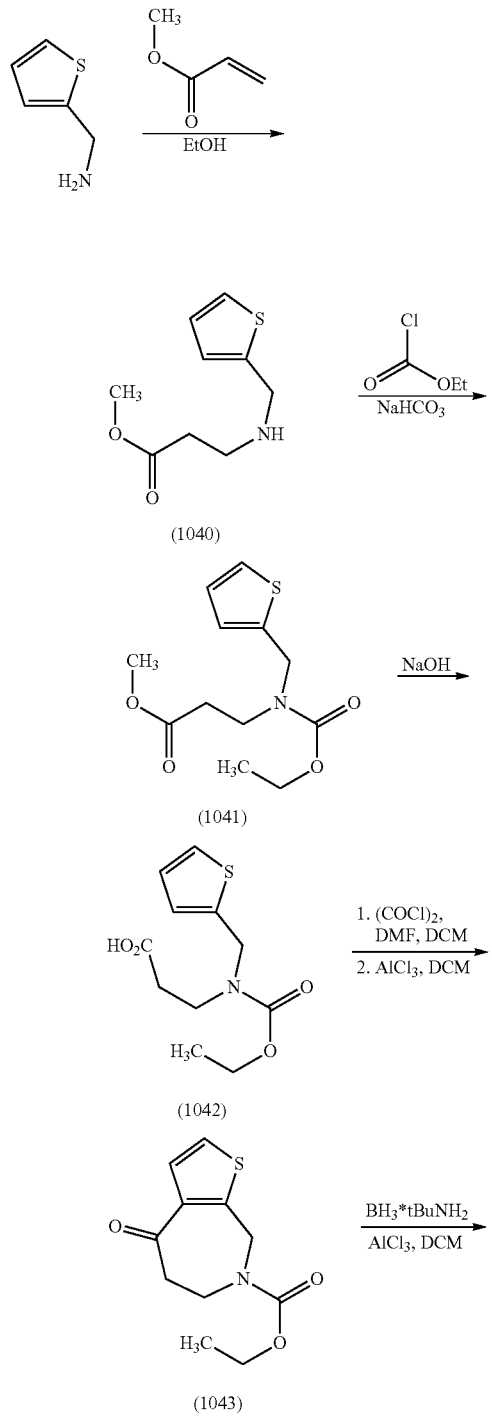

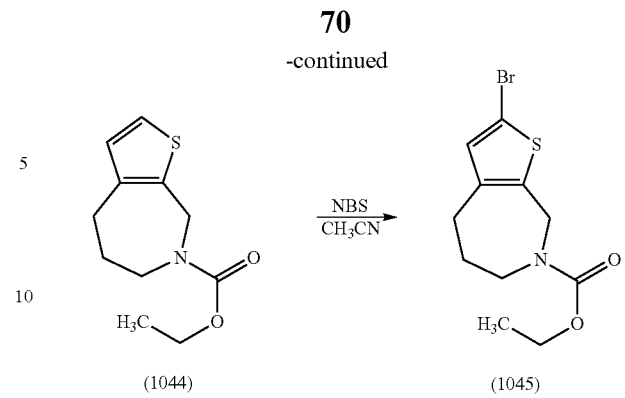

To a solution of thiophen-2-ylmethanamine (20.0 g, 176.7 mmol) in ethanol (1 L) at 0° C. was added methyl acrylate (15.21 g, 176.7 mmol). The reaction was allowed to warm to room temperature overnight, at which point HPLC analysis indicated that the reaction was complete. The solvent was removed in vacuo to give methyl 3-(thiophen-2-ylmethylamino)propanoate (Compound 1040) as a pale tan oil (35.21 g, 99%); $^1$H NMR (300 MHz, CDCl$_3$): δ 7.28 (s, CHCl$_3$), 7.22 (dd, J=1.5, 4.7 Hz, 1H), 6.97-6.95 (m, 2H), 4.16 (q, J=7.1 Hz, 2H), 4.02 (s, 3H), 3.69 (d, J=5.0 Hz, 2H), 2.95 (t, J=6.5 Hz, 2H) and 2.57-2.48 (m, 2H).

To a solution of Compound 1040 (35.2 g, 176.6 mmol) in 1:1 water/THF (1. L) was added solid sodium bicarbonate (32.6 g, 388.6 mmol) and ethyl chloroformate (20.3 mL, 212.0 mmol). The reaction was stirred at room temperature overnight, at which point LCMS indicated complete disappearance of starting material. The reaction mixture was diluted with water, extracted with ethyl acetate, and the volatiles removed under reduced pressure to give methyl 3-(ethoxycarbonyl(thiophen-2-ylmethyl)amino)propanoate as a pale yellow oil (Compound 1041, 19.9 g, 41%); $^1$H NMR (300 MHz, CDCl$_3$): δ 7.20-7.12 (m, 1H), 6.94-6.83 (m, 2H), 4.56 (s, 2H), 4.10 (td, J=14.5, 7.3 Hz, 2H), 3.52 (s, 3H), 3.46 (t, J=6.6 Hz, 2H), 2.47-2.39 (m, 2H), 1.97 (s, H) and 1.24-1.15 (m, 3H) ppm. The aqueous layer contained some 3-(ethoxycarbonyl(thiophen-2-ylmethyl)amino)propanoic acid (Compound 1042) resulting from hydrolysis of the methyl ester. Compound 1042 could be isolated by adjusting the pH of the aqueous layer to 2 with 6M HCl followed by extraction with 10% n-BuOH in chloroform, which after concentration gave the carboxylic acid as a pale yellow oil (17.33 g).

A solution of Compound 1041 (19.9 g, 73.3 mmol) in ethanol (700 mL) containing KOH (4.94 g, 88.01 mmol) was stirred at room temperature for 3 hours, at which time LCMS analysis indicated complete disappearance of starting material. The crude reaction was concentrated in vacuo, the pH adjusted to 2 by the addition of 1 M HCl, and the resulting solution extracted with 10% n-BuOH in chloroform. The organics were concentrated to give 3-(ethoxycarbonyl (thiophen-2-ylmethyl)amino)propanoic acid as a pale tan oil (Compound 1042, 17.1 g, 90%); $^1$H NMR (300 MHz, CDCl$_3$) d 7.19-7.11 (m, 1H), 6.87 (dd, J=3.3, 5.0 Hz, 2H), 4.58 (s, 2H), 4.14 (q, J=7.1 Hz, 2H), 3.47 (t, J=6.9 Hz, 4H) and 1.23 (t, J=7.0 Hz, 3H).

To a solution of Compound 1042 (5.0 g, 19.43 mmol) in methylene chloride (200 mL) containing one drop of DMF at 0° C. was added oxalyl chloride (2.03 mL, 23.32 mmol). The reaction mixture was stirred at RT until LCMS analysis (after a benzyl amine quench of the aliquot to be analyzed) indicated complete conversion to the intermediate acyl chloride. The reaction was concentrated by 50%, at which point solid aluminum chloride (5.18 g, 38.86 mmol) was added. The reaction was then stirred at room temperature overnight. The reaction was cooled to 0° C. and methanol (50 mL) carefully added. After gas evolution had ceased, 100 mL of saturated sodium bicarbonate was added carefully. After gas evolution had ceased the reaction was extracted with 10% n-BuOH in chloroform, concentrated, and the residue purified by silica chromatography (0-50% ethyl acetate/hexanes) to give ethyl 4-oxo-5,6-dihydro-4H-thieno[2,3-c]azepine-7(8H)-carboxylate (Compound 1043) as a pale tan oil (1.27 g, 27%).

Solid borane-t-butylamine pellets (2.77 g, 31.84 mmol) were crushed and suspended in methylene chloride (300 mL) at 0° C. Solid aluminum trichloride (2.12 g, 15.92 mmol) was added and the mixture was stirred for 1 hour. Compound 1043 (1.27 g, 5.31 mmol) was added slowly and the reaction mixture allowed to warm to room temperature overnight. The reaction was quenched by addition of ethanol (50 mL) then saturated ammonium chloride (100 mL). The mixture was brought to a neutral pH with saturated sodium bicarbonate, extracted with ethyl acetate (3×100 mL), and concentrated to give ethyl 5,6-dihydro-4H-thieno[2,3-c]azepine-7(8H)-carboxylate (Compound 1044) as a tan oil; $^1$H NMR (300 MHz, CDCl$_3$): δ 6.95-6.85 (m, 1H), 6.70 (d, J=4.7 Hz, 1H), 4.49 (s, 2H), 4.18-4.00 (m, 2H), 3.66-3.58 (m, 2H), 2.77 (t, J=5.7 Hz, 2H), 1.62 (qn, J=6.0 Hz, 2H) and 1.24-1.08 (m, 3H).

To a solution of Compound 1044 (1.78 g, 7.90 mmol) in acetonitrile (80 mL) at 0° C. was slowly added NBS (1.69 g, 9.48 mmol). The reaction was stirred at room temperature for 30 minutes, at which point HPLC analysis indicated disappearance of starting material. The reaction was quenched by addition of saturated sodium bicarbonate (50 mL) and stirred for one hour. The reaction was then extracted with diethyl ether (3×100 mL), the organics concentrated, and the residue purified by silica chromatography (5-30% ethyl acetate in hexanes) to give ethyl 2-bromo-5,6-dihydro-4H-thieno[2,3-c]azepine-7(8H)-carboxylate as a pale yellow oil (Compound 1045, 2.07 g, 86% yield); $^1$H NMR (300 MHz, CDCl$_3$): δ 6.67 (s, 1H), 4.38 (s, 2H), 4.15-3.99 (m, 4H), 3.64 (d, J=3.8 Hz, 2H), 2.73-2.67 (m, 2H) and 1.22-1.09 (m, 3H).

Example 13

Ethyl 2-bromo-7,8-dihydro-4H-thieno[3,2-c]azepine-5-carboxylate

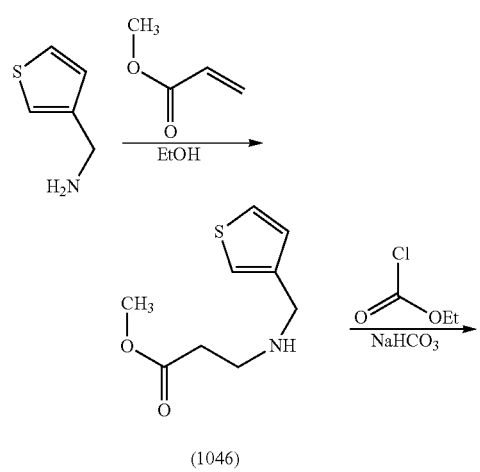

(1046)

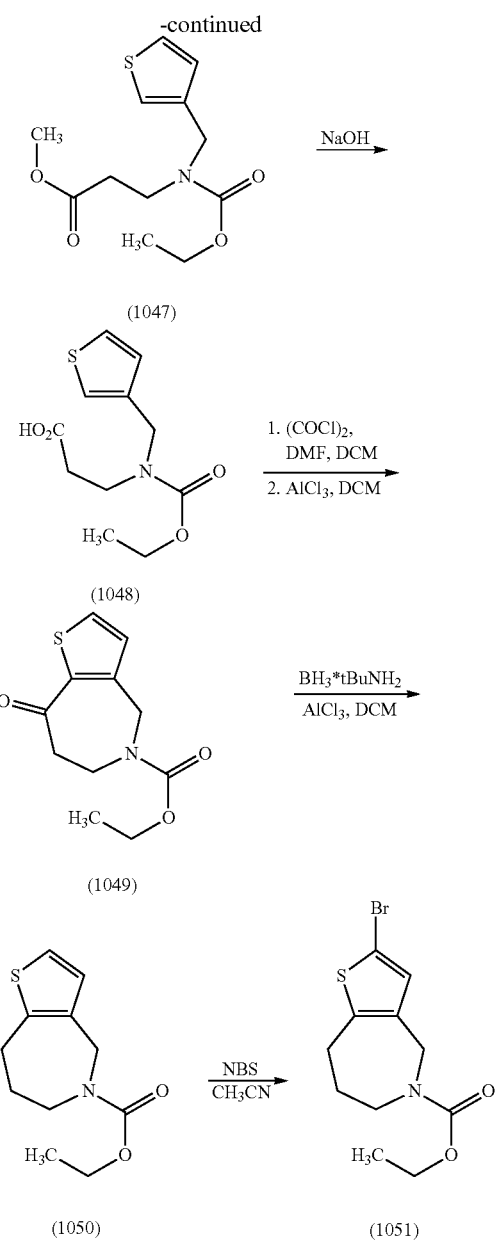

To a solution of thiophen-3-ylmethanamine (4.0 g, 35.34 mmol) and ethyl acrylate (0.921 mL, 35.34 mmol) in ethanol was stirred at room temperature overnight, at which point HPLC analysis indicated disappearance of starting material. The reaction was concentrated to give ethyl 3-(thiophen-3-ylmethylamino)propanoate (Compound 1046, 3.36 g, 45% yield) as a pale yellow oil.

To a solution of Compound 1046 (3.36 g, 15.75 mmol) in ethanol (100 mL) was added saturated sodium bicarbonate (25 mL) and ethyl chloroformate (1.801 mL, 18.9 mmol). The reaction mixture was stirred at room temperature overnight, at which point 1.0 M aqueous potassium hydroxide (63.0 mL, 63.0 mmol) was added. The mixture was stirred at room temperature overnight, concentrated under reduced pressure, made acidic with 6N HCl, and extracted with 10% nBuOH in chloroform. The organics were concentrated to give 3-(ethoxycarbonyl(thiophen-3-ylmethyl)amino)propanoic acid as a tan oil (Compound 1048, 2.04 g, 50%); $^1$H NMR (300 MHz, CDCl₃): δ 7.56-7.48 (m, 1H), 7.44-7.38 (m, 2H), 4.75 (s, 2H), 4.49-4.39 (m, 4H), 3.92-3.77 (m, 2H), 2.62-2.58 (m, 2H) and 1.68-1.48 (m, 3H).

To a solution of Compound 1048 (2.05 g, 7.97 mmol) in methylene chloride (80 mL) containing one drop DMF at 0° C. was added oxalyl chloride (4.78 mL, 9.56 mmol). The mixture was stirred at 0° C. for one hour and the volatiles were removed in vacuo. The resulting intermediate acyl chloride was dissolved in methylene chloride and cooled to 0° C., followed by the addition of aluminum trichloride (2.66 g, 19.92 mmol). The reaction was allowed to warm to room temperature overnight. The mixture was carefully quenched with ethanol (25 mL) and allowed to stir for 30 minutes before washing with 100 mL 1N HCl, saturated sodium bicarbonate, and again with 1N HCl. The organic layer was dried, filtered through silica with the aid of methylene chloride/ethanol, then concentrated under reduced pressure to give ethyl 8-oxo-7,8-dihydro-4H-thieno[3,2-c]azepine-5-carboxylate as a pale yellow oil (Compound 1049, 1.645 g, 86%); ¹H NMR (300 MHz, CDCl₃): δ 7.51 (d, J=5.1 Hz, 1H), 6.89 (dd, J=5.1, 9.0 Hz, 1H), 4.82 (s, 2H), 4.10 (qn, J=7.0 Hz, 2H), 3.66 (t, J=10.9 Hz, 2H), 2.97-2.90 (m, 2H) and 1.21 (t, J=6.8 Hz, 3H).

Solid borane-t-butylamine pellets (3.59 g, 41.24 mmol) were crushed and suspended in methylene chloride (70 mL) at 0° C. Solid aluminum trichloride (2.75 g, 20.62 mmol) was added and this mixture was stirred for 1 hour. Compound 1049 (1.27 g, 5.31 mmol) was added slowly and the reaction mixture was allowed to warm to room temperature overnight. The reaction was quenched by addition of ethanol (50 mL) then saturated ammonium chloride (100 mL). The mixture was brought to a neutral pH with saturated sodium bicarbonate, extracted with ethyl acetate (3×100 mL), and concentrated under reduced pressure to give ethyl 7,8-dihydro-4H-thieno[3,2-c]azepine-5-carboxylate (Compound 1050) as a tan oil; ¹H NMR (300 MHz, CDCl₃): δ 6.91 (d, J=4.9 Hz, 1H), 4.45 (d, J=16.5 Hz, 2H), 4.08 (t, J=6.9 Hz, 2H), 3.72 (s, 2H), 2.94 (t, J=5.8 Hz, 2H), 1.86 (d, J=2.0 Hz, 2H), 1.21 (d, J=6.3 Hz, 3H) and 0.07 (s, H).

To a solution of Compound 1050 (1.53 g, 6.79 mmol) in acetonitrile (70 mL) at 0° C. was slowly added NBS (1.69 g, 9.48 mmol). The reaction was stirred at room temperature for 30 minutes, at which point HPLC analysis indicated disappearance of starting material. The reaction was quenched by addition of saturated sodium bicarbonate (50 mL) and stirred for one hour. The mixture was extracted with diethyl ether (3×100 mL), the volatiles removed under reduced pressure, and the residue purified by silica chromatography (0-30% ethyl acetate in hexanes) to give ethyl 2-bromo-7,8-dihydro-4H-thieno[3,2-c]azepine-5-carboxylate as a pale yellow oil (Compound 1051, 2.07 g, 86% yield); ¹H NMR (300 MHz, CDCl₃): δ 6.84-6.70 (m, 1H), 4.30 (d, J=15.4 Hz, 2H), 4.02 (q, J=6.7 Hz, 2H), 3.63 (s, 2H), 2.78 (dd, J=4.6, 5.7 Hz, 2H), 1.80 (s, 2H) and 1.16 (t, J=6.8 Hz, 3H).

Example 14 tert-Butyl 4-(5-bromo-3-methylthiophen-2-yl)piperidine-1-carboxylate

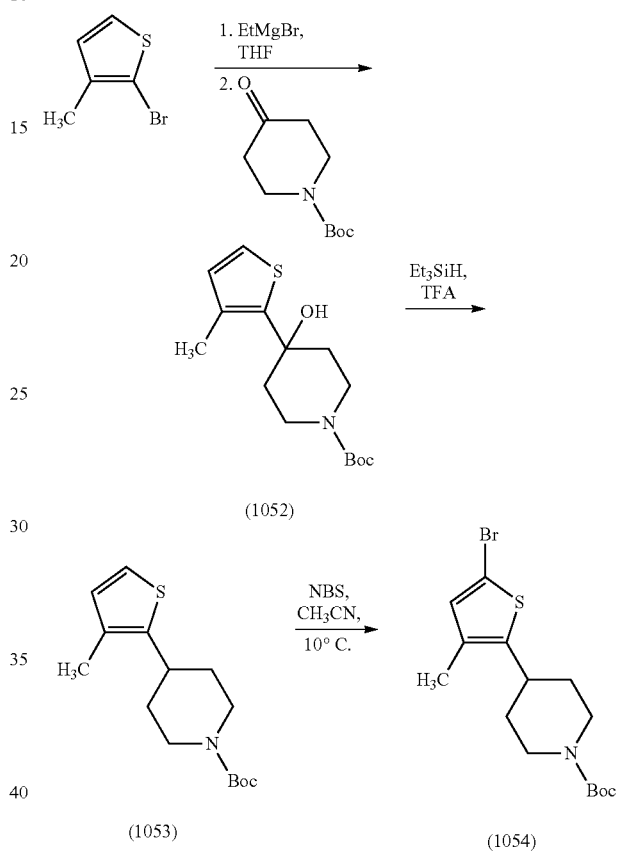

To a solution of EtMgBr (300 mL of 1.0M, 300 mmol) in THF (400 mL) at RT was added 2-bromo-3-methylthiophene (48.28 g, 272.7 mmol) dropwise. The mixture was stirred at RT for 72 hours. To the reaction mixture was added a solution of tert-butyl 4-oxopiperidine-1-carboxylate (54.33 g, 272.7 mmol) in THF at RT. The reaction was stirred for 3 hours and 2 N HCl was added to quench the reaction. The mixture was extracted with EtOAc and the combined organics washed with water, satd' NaHCO₃ solution, and dried over MgSO₄. Removal of the volatiles in vacuo gave a gummy product, to which was added EtOAc. After shaking for 10 min a white precipitate appeared, which was collected by filtration and washed with EtOAc. The filtrate was evaporated again and the precipitation step repeated to obtain additional product, which was combined with the solid previously collected to yield tert-Butyl 4-hydroxy-4-(3-methylthiophen-2-yl)piperidine-1-carboxylate (Compound 1052, 58 g, 71.5% yield; ¹H NMR (300 MHz, DMSO-d₆): δ 7.17 (d, J=5.0 Hz, 1H), 6.79 (d, J=5.1 Hz, 1H), 5.47 (s, 1H), 3.82 (brd, 2H), 3.09 (brs, 2H), 2.26 (s, 3H), 1.84-1.79 (m, 4H) and 1.41 (s, 9H).

To a solution of Compound 1052 (41.5 g, 139.5 mmol) in dry DCM (400 mL) was added triethylsilane (81.10 g, 111.4 mL, 697.5 mmol). The mixture was cooled to −78° C. and TFA (79.53 g, 53.74 mL, 697.5 mmol) was added slowly. The reaction mixture was warmed to −10° C. with stirring during 3 hours. Additional TFA was added and the reaction was warmed to RT and stirred for 3 hours. The volatiles were removed in vacuo and the residue poured into a solution of 2N HCl. The aqueous solution was washed with hexanes followed by adjusting to pH to 12 with solid NaOH under an atmosphere of nitrogen. To this basic solution was added equal volume of DCM, followed by the addition of di-t-butyldicarbonate (36.53 g, 167.4 mmol). The mixture was stirred at RT for 30 min, extracted with DCM, the organics dried over MgSO₄, filtered, and evaporated under vacuum to afford tert-butyl 4-(3-methylthiophen-2-yl)piperidine-1-carboxylate (Compound 1053), which was used as is in the subsequent reaction.

To a solution of tert-butyl 4-(5-bromo-3-methylthiophen-2-yl)piperidine-1-carboxylate (39 g, 138.6 mmol) in CH₃CN (328.0 mL) was added NBS (24.67 g, 138.6 mmol) at 10° C. The reaction mixture was stirred at RT for 30 min. Aqueous Na₂SO₃ was added to quench the reaction and the mixture diluted with EtOAc, washed with 2N NaOH, and the volatiles removed under reduced pressure. The residue was purified by medium pressure silica gel chromatography, eluting with 2%-10% EtOAc/Hexane over 20 minutes, to give 47 g tert-butyl 4-(5-bromo-3-methylthiophen-2-yl)piperidine-1-carboxylate (Compound 1054) as white solid; $^1$H NMR (300 MHz, CDCl₃): δ 6.74 (s, 1H), 4.25 (br, 2H), 3.00-2.90 (m, 1H), 2.78 (t, 2H), 2.15 (s, 3H), 1.85 (brd, 2H), 1.56-1.52 (m, 2H) and 1.49 (s, 9H).

tert-Butyl 3-(5-bromo-3-methylthiophen-2-yl)piperidine-1-carboxylate (Compound 1055) and tert-butyl 4-(5-bromo-3-methylthiophen-2-yl)azepane-1-carboxylate (Compound 1056) were prepared by procedures similar to that provided above for the preparation of Compound 1054.

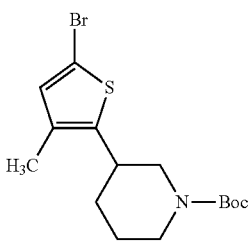

(1055)

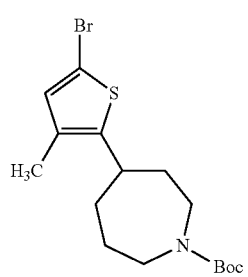

(1056)

Example 15 tert-Butyl 4-(5-bromo-2-methylthiophen-3-yl)piperidine-1-carboxylate

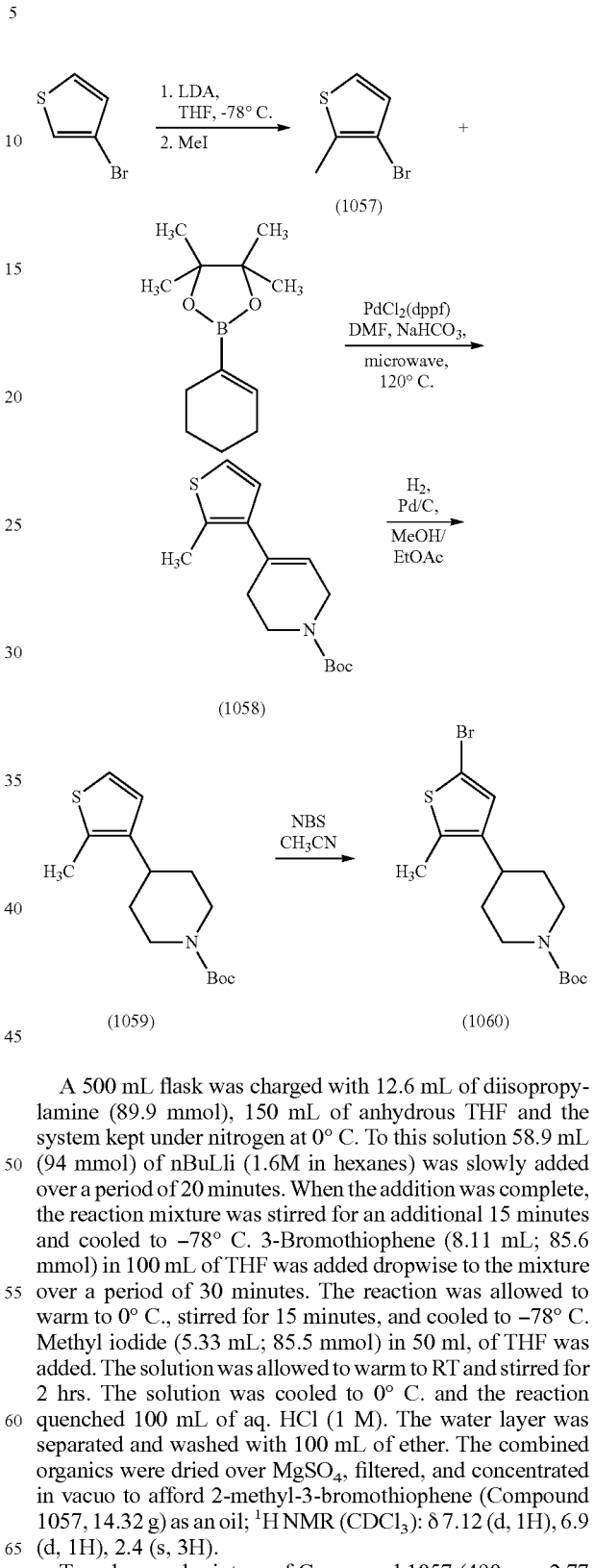

A 500 mL flask was charged with 12.6 mL of diisopropylamine (89.9 mmol), 150 mL of anhydrous THF and the system kept under nitrogen at 0° C. To this solution 58.9 mL (94 mmol) of nBuLli (1.6M in hexanes) was slowly added over a period of 20 minutes. When the addition was complete, the reaction mixture was stirred for an additional 15 minutes and cooled to −78° C. 3-Bromothiophene (8.11 mL; 85.6 mmol) in 100 mL of THF was added dropwise to the mixture over a period of 30 minutes. The reaction was allowed to warm to 0° C., stirred for 15 minutes, and cooled to −78° C. Methyl iodide (5.33 mL; 85.5 mmol) in 50 ml, of THF was added. The solution was allowed to warm to RT and stirred for 2 hrs. The solution was cooled to 0° C. and the reaction quenched 100 mL of aq. HCl (1 M). The water layer was separated and washed with 100 mL of ether. The combined organics were dried over MgSO₄, filtered, and concentrated in vacuo to afford 2-methyl-3-bromothiophene (Compound 1057, 14.32 g) as an oil; $^1$H NMR (CDCl₃): δ 7.12 (d, 1H), 6.9 (d, 1H), 2.4 (s, 3H).

To a degassed mixture of Compound 1057 (490 mg; 2.77 mmol) in dry DMF (2 mL) was added tert-butyl 4-(4,4,5,5- tetramethyl-1,3,2-dioxaborolan-2-yl)-5,6-dihydropyridine-1 (2H)-carboxylate (779 mg; 2.52 mmol), saturated NaHCO₃ (3.15 mL; 3.78 mmol), and 184 mg of Pd Cl₂ (dppf). The reaction mixture was heated for 10 minutes at 120° C. under microwave irradiation, diluted with EtOAc, and filtered. The filtrate was washed with water and brine, dried over sodium sulfate, and concentrated in vacuo. The residue was purified by medium pressure silica gel chromatography, eluting with 0-30% EtOAc/hexanes over 30 minutes, to give tert-butyl 5,6-dihydro-4-(2-methylthiophen-3-yl)pyridine-1(2H)-carboxylate (Compound 1058, 557 mg, 79% yield) as a light yellow oil; ¹H NMR (CDCl₃): δ 7.12 (d, 1H), 6.85 (d, 1H), 5.7 (bs, 1H), 4.1 (bs, 2H), 3.6 (t, 2H), 2.4 (s, 3H), 2.3 (m, 2H).

Compound 1058 (835 mg; 3 mmol) was dissolved in 50 mL of MeOH/EtOAc (1:1) and stirred under an atmosphere of hydrogen at 45 psi for 3 hours. The mixture was filtered through diatomaceous earth and concentrated in vacuo to give tert-butyl 4-(2-methylthiophen-3-yl)piperidine-1-carboxylate (Compound 1059, 0.816 g, 97% yield) as an oil.

To a solution of Compound 1059 (810 mg; 2.89 mmol) in 15 mL of acetonitrile was added NBS portionwise (505 mg; 2.83 mmol). The reaction mixture was stirred at room temperature for 10 minutes, quenched with saturated Na₂SO₃ solution, and extracted with EtOAc (3×). The combined organics were dried (Na₂SO₄), filtered, and concentrated in vacuo to give a crude light yellow semi-solid. The residue was purified by medium pressure silica gel chromatography, eluting with 0-20% EtOAc/hexanes over 25 minutes, to give tert-butyl 4-(5-bromo-2-methylthiophen-3-yl)piperidine-1-carboxylate (Compound 1060, 590 mg, 57%); ¹H NMR (CDCl₃): δ 6.7 (s, 1H), 4.2 (m, 2H), 2.6 (m, 3H), 2.2 (s, 3H), 1.6 (m, 2H), 1.5 (m, 2H), 1.45 (s, 9H).

Example 16 tert-Butyl 4-(5-bromo-4-methylthiophen-2-yl)piperidine-1-carboxylate

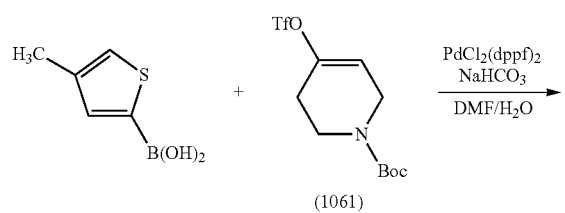

(1061)

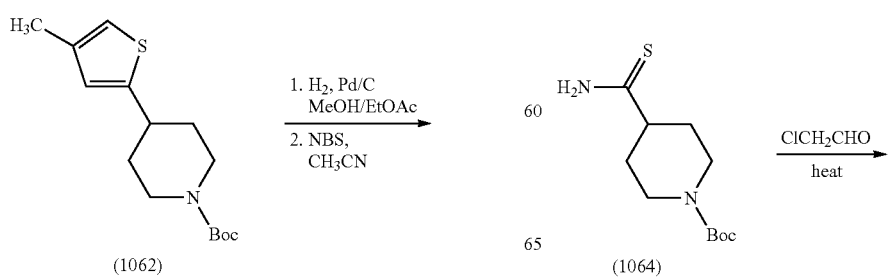

(1062)

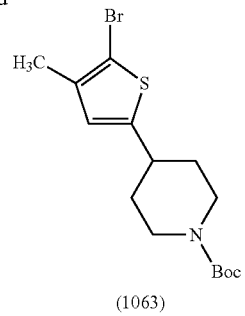

(1063)

A solution of 1-(tert-butoxycarbonyl)-1,2,3,6-tetrahydropyridin-4-yl trifluoromethanesulfonate (Compound 1061, 2.65 g, 8 mmol, prepared according to the procedure described in *Organic Letters*, 3(15), pp. 2317-2320, 2001), 4-methylthiophene-2-boronic acid (1.14 g, 8 mmol), and sodium bicarbonate (1.01 g in 10 mL water, 12 mmol) in DMF (30 mL) was degassed with a nitrogen stream for 20 minutes. To the mixture was added tris(diphenylphosphinoferrocene) dichloropalladium (584 mg, 0.8 mmol) and the reaction was stirred for 10 minutes at 120° C. under microwave irradiation. The crude mixture was diluted with ethyl acetate and washed successively with water (2×15 mL) and brine (1×15 mL). The organic layer was dried over magnesium sulfate and concentrated under reduced pressure. The resulting residue was purified via silica gel chromatography to afford 1.67 g of tert-butyl 4-(4-methylthiophen-2-yl)piperidine-1-carboxylate (Compound 1062) as a yellow oil; ESMS (M+H)=224.

To Compound 1062 (1.67 g, 5.98 mmol) in a solution of methanol and ethyl acetate (40 mL, 1:1) was added palladium on carbon (1 g, 10%, Degussa type). The reaction was shaken under hydrogen atmosphere at 45 psi on a Parr apparatus for 1 hour, filtered through diatomaceous earth, and concentrated under reduced pressure. The resulting material was dissolved in acetonitrile (30 mL) and treated with N-bromosuccinimide (1.14 g, 6.4 mmol). The reaction mixture was stirred for 30 minutes at room temperature and quenched with a saturated solution of sodium sulfite. The crude product was extracted with EtOAc (2×30 mL) and the combined organics were dried over magnesium sulfate and concentrated under reduced pressure. The residue was purified via silica gel chromatography to provide 1.26 g of tert-butyl 4-(5-bromo-4-methylthiophen-2-yl)piperidine-1-carboxylate Compound 1063) as a pale yellow solid; ¹H NMR (300 MHz, CDCl₃): δ 6.42 (s, H), 4.20-4.01 (m, 2H), 2.77-2.68 (m, 3H), 2.05 (s, 3H), 1.84 (d, J=12.3 Hz, 2H) and 1.50-1.39 (m, 11H).

Example 17 tert-Butyl 4-(5-bromothiazol-2-yl)piperidine-1-carboxylate (1064)

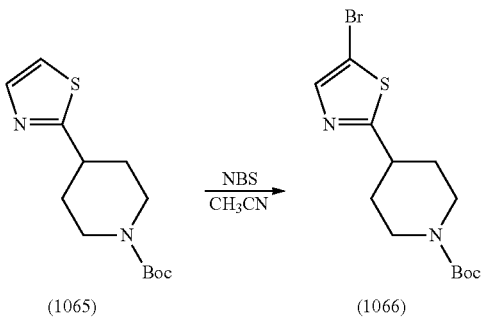

To a solution of tert-butyl 4-thiocarbamoylpiperidine-1-carboxylate (Compound 1064, 1 g, 4.09 mmol) in acetone (5 mL) was added 2-chloroacetaldehyde (0.32 g, 4.08 mmol). The mixture was heated under reflux for 4 hours. Additional 2-chloroacetaldehyde (0.32 g, 4.08 mmol) was added and heating was continued for another 14 hrs. The solvent was removed by evaporation and the crude product was purified by silica gel chromatography to give tert-butyl 4-(thiazol-2-yl)piperidine-1-carboxylate (Compound 1065) as an oil (530 mg, 1.97 mmol); LCMS (M+H)=213.1; $^1$H NMR (300 MHz, CDCl$_3$): δ 7.74 (d, J=3.3 Hz, 1H), 7.26 (d, J=3.3 Hz, 1H), 4.23 (brd, 2H), 3.22 (m, 1H), 2.91 (t, 2H), 2.14 (m, 2H), 1.77 (m, 2H), 1.48 (s, 9H).

To a solution of Compound 1065 (530 mg, 1.97 mmol) in acetonitrile (10 mL) was added NBS (1.40 g, 7.86 mmol). The mixture was stirred at RT for 14 hours and heated at 50° C. for 4 hours. The reaction mixture with some starting material recovered was poured into a solution of Na$_2$SO$_3$ (30 mL) and 6N NaOH (2 mL). The aqueous layer was extracted with EtOAc, dried over MgSO4, and the combined organics concentrated in vacuo. The residue was purified by silica gel chromatography to provide tert-Butyl 4-(5-bromothiazol-2-yl)piperidine-1-carboxylate (Compound 1066) as a yellow oil (210 mg, 0.61 mmol); $^1$H NMR (300 MHz, CDCl$_3$): δ 7.59 (s, 1H), 4.20 (brd, J=12.9 Hz, 2H), 3.13 (tt, J=3.8, 11.5 Hz, 1H), 2.89 (t, J=11.6 Hz, 2H), 2.08 (d, J=11.7 Hz, 2H), 1.72 (dq, J=4.3, 11.9 Hz, 2H), 1.49 (s, 9H).

Example 18

4-(5-bromo-3-methylthiophen-2-yl)pyridine and 3-(5-bromo-3-methylthiophen-2-yl)pyridine A mixture of 2-bromo-3-methylthiophene (5 g, 28.24 mmol), pyridin-4-ylboronic acid (4.2 g, 33.89 mmol), and saturated sodium bicarbonate (70.60 mL of 1.2 M, 84.72 mmol) in DMF (100 mL) was degassed with nitrogen. PdCl$_2$(dppf) (1.239 g, 1.694 mmol) was added and the reaction mixture heated at 90° C. under an atmosphere of nitrogen for 14 hours. After cooling, the mixture was poured into a saturated NaHCO$_3$ solution, which was extracted with EtOAc. The organics were washed with saturated NaHCO$_3$, dried over MgSO$_4$, and the volatiles were removed by evaporation. The residue was purified by medium pressure silica gel chromatography, eluting with 1%-50% EtOAc/hexanes, to afford 4-(3-methylthiophen-2-yl)pyridine (3 g, 61% yield) as slightly yellow oil; $^1$H NMR (300 MHz, CDCl$_3$): δ 8.54 (dd, J=1.6, 4.5 Hz, 2H), 7.30 (dd, J=1.7, 4.5 Hz, 2H), 7.23 (d, J=5.1 Hz, 1H), 6.88 (d, J=5.1 Hz, 1H) and 2.32 (s, 3H). This compound (3 g, 17.12 mmol) was dissolved in acetonitrile (100 mL) and NBS (3.047 g, 17.12 mmol) was added at RT. The reaction mixture was stirred at RT for 24 hours and the reaction quenched by adding an aqueous solution of Na$_2$SO$_3$ and saturated NaHCO$_3$ solution. The resulting precipitate was collected and washed with water. After drying under high vacuum, 4-(5-bromo-3-methylthiophen-2-yl)pyridine (Compound 1067, 4 g, 92%) was obtained as yellow solid; ESMS (M+H)=254.05; $^1$H NMR (300 MHz, DMSO-d$_6$): δ 8.74 (dd, J=1.5, 5.0 Hz, 2H), 7.78 (dd, J=1.5, 5.0 Hz, 2H), 7.46 (s, 1H) and 2.46 (s, 3H).

3-(5-Bbromo-3-methylthiophen-2-yl)pyridine (Compound 1068) was prepared by procedures similar to that provided above for the preparation of Compound 1067; ESMS (M+H)=254.05; $^1$H NMR (300 MHz, DMSO-d$_6$): δ 8.69 (d,

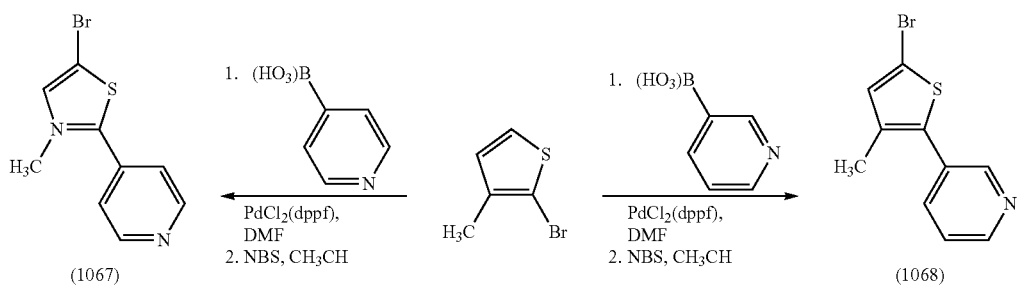

J=2.1 Hz, 1H), 8.59 (dd, J=1.5, 4.8 Hz, 1H), 7.71 (dt, J=7.9, 2.4 Hz, 1H), 7.36 (dd, J=4.8, 7.9 Hz, 1H), 6.95 (s, 1H) and 2.29 (s, 3H).

Example 19

5-Bromo-3-(1-(2,3-difluoro-4-methylphenyl)-1H-tetrazol-5-yl)pyridin-2-amine and 5-bromo-3-(1-(2,3-difluoro-4-methoxyphenyl)-1H-tetrazol-5-yl)pyridin-2-amine

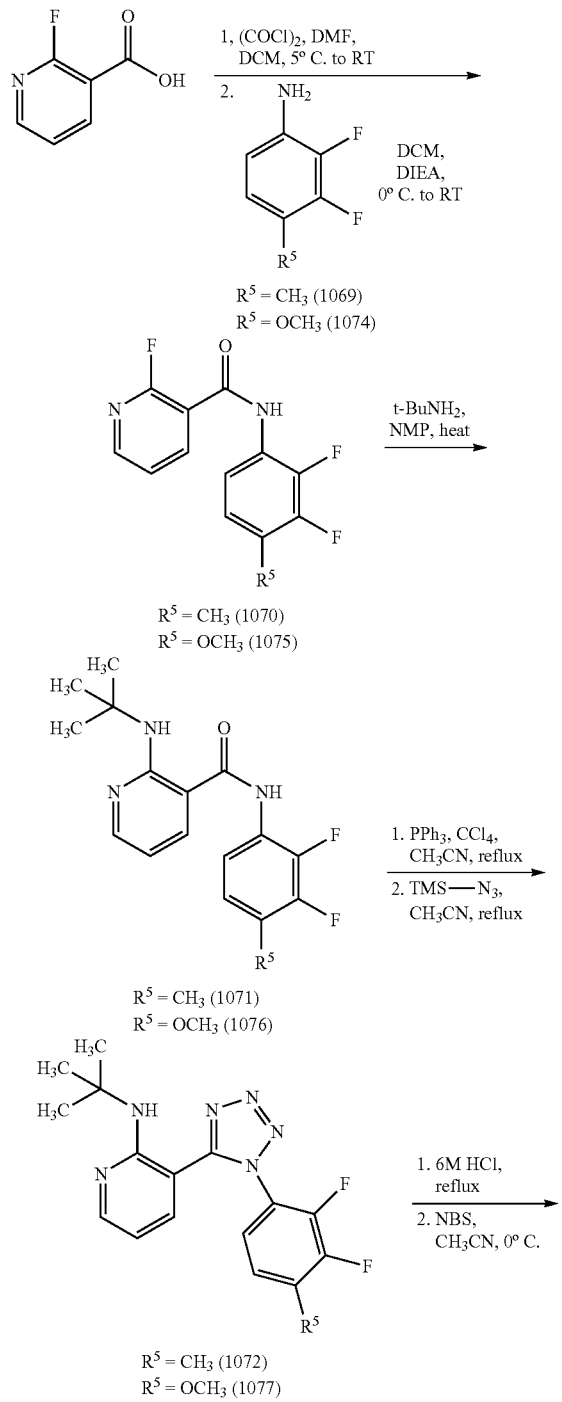

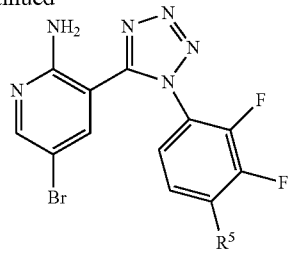

$R^5 = CH_3$ (1073)
$R^5 = OCH_3$ (1078)

2-Fluoronicotinic acid (18.8 g) was suspended in 500 ml of anhydrous dichloromethane and 1.3 mL of anhydrous N,N-dimethylformamide. The solution was cooled to 5° C. with an ice bath. Oxalyl chloride (11.3 mL) was added to the cooled mixture dropwise. After addition, the mixture was warmed to room temperature and stirred until all the solid had gone into solution. 2,3-Difluoro-4-methylaniline (Compound 1069, 20 g) was added dropwise to the clear solution at 0° C. After the addition was complete, DIEA (70 mL) was added to the cooled solution dropwise. The mixture was warmed to room temperature and stirred for 16 hours. The mixture was washed twice with 200 mL of saturated sodium bicarbonate, once with 300 mL of water, and once with 300 mL of brine. The organics were dried over anhydrous sodium sulfate, filtered, and the volatiles removed under reduced pressure to afford an orange solid. This solid was slurried in 350 mL of hexanes, stirred for 30 minutes, collected by vacuum filtration, washed well with hexanes, and dried under vacuum to afford 2-fluoro-N-(2,3-difluoro-4-methylphenyl)pyridine-3-carboxamide (Compound 1070, 30.6 g, 86% yield); ESMS (M+1)=267.1; $^1$H NMR (300 MHz, CDCl$_3$): δ 8.78-8.62 (m, 2H), 8.42-8.39 (m, 1H), 8.06-8.00 (m, 1H), 7.43 (dt, J=10.0, 3.1 Hz, 1H), 6.98 (dd, J=1.7, 16.0 Hz, 1H) and 2.31 (d, J=1.9 Hz, 3H).

Compound 1070 (30.6 g) was dissolved in 300 mL of N-methylpyrrolidinone and 100 mL of tert-butylamine and heated to 100° C. for 24 hours. The reaction was cooled to room temperature and poured into 1 L of saturated sodium bicarbonate. A precipitate formed, which was collected by vacuum filtration, washed well with water, and dried in a vacuum oven overnight to afford 2-(tert-butylamino)-N-(2,3-difluoro-4-methylphenyl)pyridine-3-carboxamide (Compound 1071, 35.16 g, 95.8% yield); $^1$H NMR (300 MHz, CDCl$_3$) 8.26 (dd, J=1.8, 4.7 Hz, 1H), 8.03 (s, 1H), 7.84-7.69 (m, 3H), 6.95 (dd, J=1.5, 16.1 Hz, 1H), 6.51 (dd, J=4.8, 7.7 Hz, 1H), 2.29 (d, J=1.9 Hz, 3H) and 1.48 (s, 9H).

Compound 1071 (88.2 g, 276.2 mmol) was taken into 1200 mL of anhydrous acetonitrile. Triphenylphosphine (94.2 g, 359 mmol) was added to the mixture and stirred at room temperature for 5 minutes followed by the addition of carbon tetrachloride (32 mL, 331.4 mmol). The mixture was refluxed for 3 hours. The reaction was cooled to room temperature and TMS-azide (55 ml, 414.3 mmol) was added to the mixture. The reaction was heated to reflux for 18 hours. The reaction was cooled to room temperature, diluted with 1200 mL of methyl tert-butyl ether, and washed with saturated sodium bicarbonate. The aqueous layer was washed with methyl tert-butyl ether. The organics were combined and washed with once with water and twice with brine. The organic layer was dried over anhydrous sodium sulfate, filtered, and the volatiles removed under reduced pressure to afford a honey colored syrup, which was dissolved in methyl tert-butyl ether and the triphenylphosphine oxide precipitate was removed by vacuum filtration. The filtrate was evaporated in vacuo, the residue redissolved in methyl tert-butyl ether, and the resulting solution poured onto 1500 g of silica gel. Elution with 1:2 methyl tert-butyl ether/hexanes gave a thick yellow precipitate after evaporation of the solvents from the fractions containing pure product. This wet solid was diluted with hexanes, collected by filtration, and washed well with hexanes to afford a light yellow solid, which was dried at 60° C. for 16 hours to yield N-tert-butyl-3-(1-(2,3-difluoro-4-methylphenyl)-1H-tetrazol-5-yl)pyridin-2-amine (Compound 1072, 79.9 g, 84% yield); $^1$H NMR (300 MHz, CDCl$_3$): δ 8.20 (dd, J=1.9, 4.7 Hz, 1H), 7.56 (s, 1H), 7.18-7.12 (m, 2H), 7.05 (dd, J=1.5, 7.8 Hz, 1H), 6.30 (dd, J=4.8, 7.8 Hz, 1H), 2.44 (s, 3H), 1.54 (s, 9H).

Compound 1072 (69 g) was taken into 210 mL of methanol and 420 mL of 6M HCl and refluxed for 18 hrs. The reaction was cooled to room temperature and the pH adjusted to 8 with 6M sodium hydroxide. The resulting white precipitate was collected by vacuum filtration, washed well with water, and dried at 55° C. under vacuum overnight to afford 3-(1-(2,3-difluoro-4-methylphenyl)-1H-tetrazol-5-yl)pyridin-2-amine (62.32 g).

3-(1-(2,3-Difluoro-4-methylphenyl)-1H-tetrazol-5-yl)pyridin-2-amine (60 g) was suspended in 1 L of anhydrous acetonitrile and cooled to 0° C. NBS (40.7 g) was added portionwise to the mixture and stirred for 1 hour. A concentrated solution of sodium sulfite was added to the mixture followed by the addition of concentrated sodium bicarbonate. After stirring at room temperature for 1 hour the reaction was filtered and washed well with water and dried overnight at 55° C. under vacuum to give 5-bromo-3-(1-(2,3-difluoro-4-methylphenyl)-1H-tetrazol-5-yl)pyridin-2-amine (Compound 1073, 64.66 g, 84.6% yield); $^1$H NMR (300 MHz, DMSO-d$_6$): δ 8.22-8.14 (m, 1H), 7.59 (d, J=2.4 Hz, 1H), 7.54-7.48 (m, 1H), 7.40 (dd, J=1.1, 15.6 Hz, 1H), 6.71 (s, 2H) and 2.38 (d, J=2.0 Hz, 3H).

The same sequence of reactions used to convert Compound 1069 to Compound 1073 were used to convert Compound 1074 to Compound 1078. Characterization data are as follows, Compound 1075: $^1$H NMR (300 MHz, CDCl$_3$): δ 8.68-8.62 (m, 2H), 8.40 (dt, J=4.7, 1.6 Hz, 1H), 8.06-7.99 (m, 1H), 7.44 (td, J=5.0, 2.5 Hz, 1H), 6.82-6.75 (m, 1H) and 3.91 (d, J=5.4 Hz, 3H); Compound 1076: $^1$H NMR (300 MHz, CDCl$_3$): δ 8.26 (dd, J=1.8, 4.7 Hz, 1H), 8.01 (s, 1H), 7.83-7.77 (m, 1H), 7.68-7.64 (m, 2H), 6.80-6.73 (m, 1H), 6.51 (dd, J=4.7, 7.7 Hz, 1H), 3.91 (s, 3H) and 1.49 (s, 9H), Compound 1077: ESMS (M+1)=361.37; and Compound 1078: $^1$H NMR (300 MHz, DMSO-d$_6$): δ 8.20 (d, J=2.5 Hz, 1H), 7.64-7.56 (m, 2H), 7.36-7.28 (m, 1H), 6.73 (s, 2H) and 3.97 (s, 3H).

The following anilines were similarly used as starting materials for the synthesis of other intermediate 5-bromo-3-(substituted-phenyl)-1H-tetrazol-5-yl)pyridin-2-amines used in the preparation of the compounds of the invention:

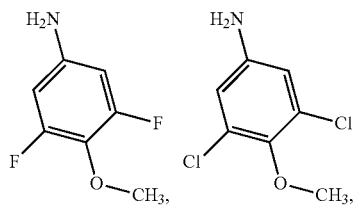

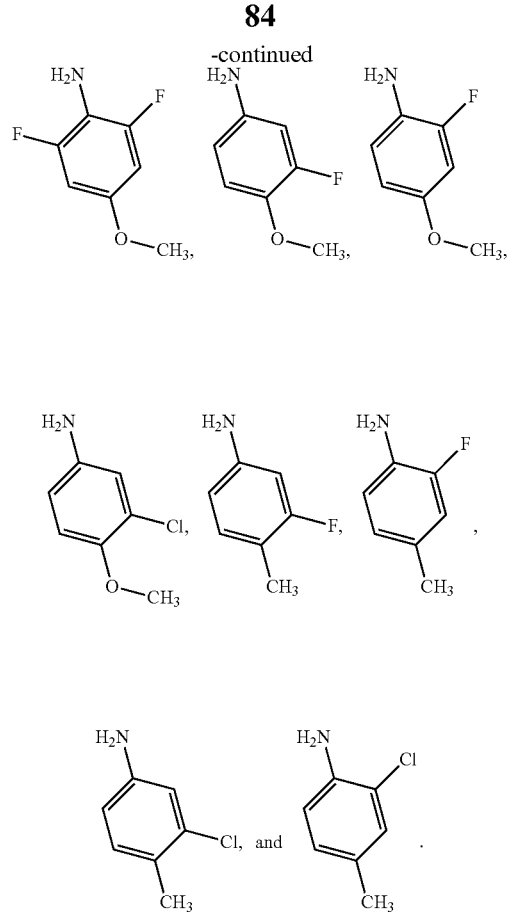

Example 20

N-tert-butyl-3-(1-(4-bromo-2,3-difluorophenyl)-1H-tetrazol-5-yl)pyridin-2-amine

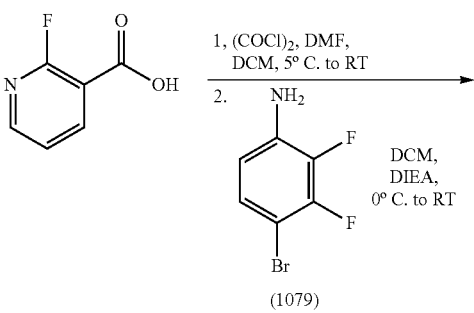

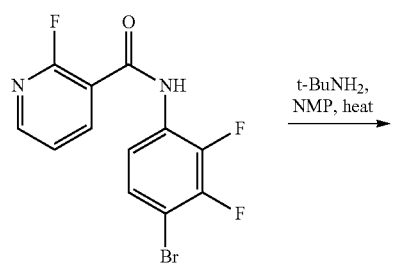

-continued

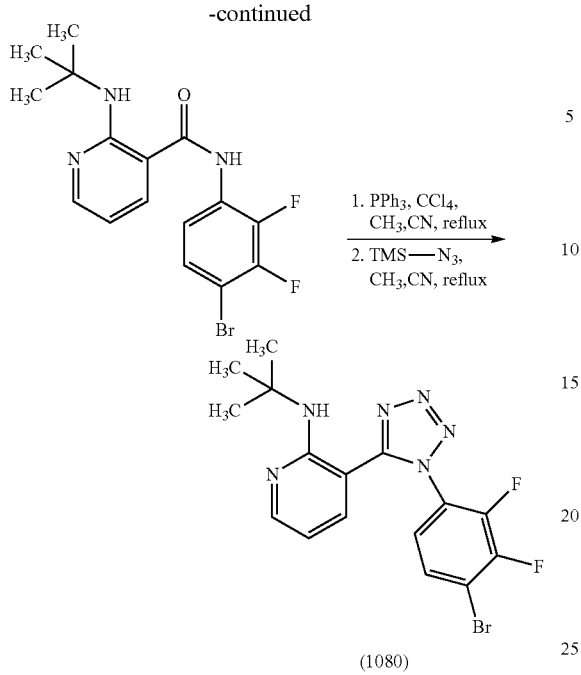

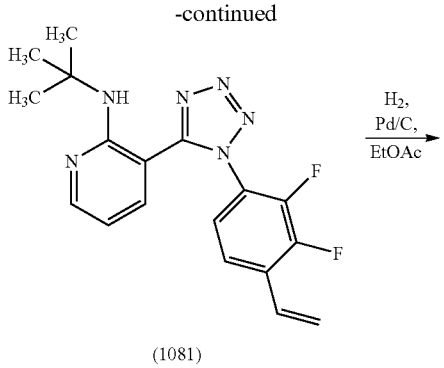

To a stirred solution of 2,3-difluoroaniline (20 g, 154.9 mmol) in HOAc (230 mL) was added over 1 hour a solution of bromine (24.75 g, 7.978 mL, 154.9 mmol) in HOAc (70 mL) at RT. The reaction mixture was stirred at RT for another 1 hour and a white precipitate appeared. The solvent was removed under reduced pressure, the residue was made basic with 6M NaOH at 0° C., and the basic solution was extracted with DCM. After drying the organics over MgSO$_4$, the volatiles were removed in vacuo to provide 4-bromo-2,3-difluoroaniline (Compound 1079); LC/MS (M+H)=207.96. This compound was reacted with the acyl chloride of 2-fluoronicotinic acid and carried through the sequence of reactions as described in Example 19 to produce N-tert-butyl-3-(1-(4-bromo-2,3-difluorophenyl)-1H-tetrazol-5-yl)pyridin-2-amine (Compound 1080); $^1$H NMR (300 MHz, DMSO-d$_6$): δ 8.21 (dd, J=1.9, 4.8 Hz, 1H), 7.90-7.84 (m, 1H), 7.54-7.48 (m, 1H), 7.44 (dd, J=1.9, 7.7 Hz, 1H), 6.71 (s, 1H), 6.58 (dd, J=4.8, 7.7 Hz, 1H) and 1.31 (s, 9H).

Example 21

N-tert-Butyl-3-(1-(4-ethyl-2,3-difluorophenyl)-1H-tetrazol-5-yl)pyridin-2-amine

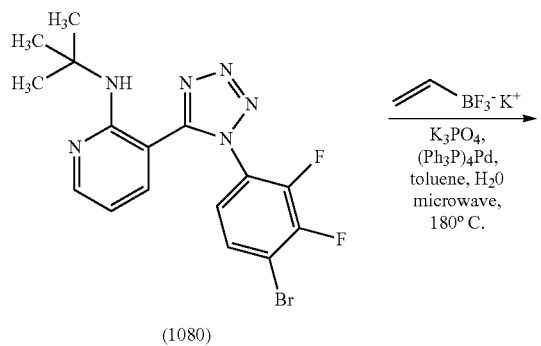

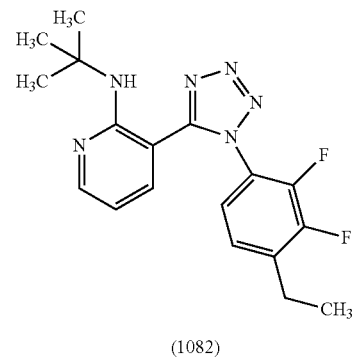

N-tert-butyl-3-(1-(4-bromo-2,3-difluorophenyl)-1H-tetrazol-5-yl)pyridin-2-amine (Compound 1080, 240 mg, 0.586 mmol), potassium vinyltrifluoroborate (94 mg, 0.704 mmol), and K$_3$PO$_4$ (410 mg, 1.935 mmol) was taken into 1.5 mL of toluene and 0.5 mL of water. The reaction was degassed by bubbling nitrogen in the mixture for 20 minutes. Tetrakis(triphenylphosphine) palladium(0) (34 mg, 0.0293 mmol) was added to the mixture and reaction heated at 180° C. for 10 minutes under microwave irradiation. The reaction was diluted with EtOAc, washed with water, dried over anhydrous sodium sulfate, filtered and the volatiles removed under reduced pressure to afford a dark brown solid that was purified by column chromatography (SiO$_2$) eluting with 0-20% EtOAc/Hexanes to afford 260 mg of Compound 1081; MS (M+1)=357.4.

N-tert-Butyl-3-(1-(2,3-difluoro-4-vinylphenyl)-1H-tetrazol-5-yl)pyridin-2-amine (Compound 1081, 260 mg) was dissolved in 30 ml of ethyl acetate. 10% Palladium on carbon was added to the mixture and the reaction flask was charged with hydrogen (1 atm). After stirring at RT for 12 hours, the reaction was filtered through diatomaceous earth, concentrated in vacuo, and the residue purified by column chromatography (SiO$_2$), eluting with 0-20% EtOAc/Hexane, to afford 130 mg of N-tert-Butyl-3-(1-(4-ethyl-2,3-difluorophenyl)-1H-tetrazol-5-yl)pyridin-2-amine (Compound 1082); MS (M+1)=359.4.

Compound 1082 can be further reacted with NBS according to procedures analogous to those provided herein to provide N-tert-butyl-5-bromo-3-(1-(4-ethyl-2,3-difluorophenyl)-1H-tetrazol-5-yl)pyridin-2-amine (Compound 1083).

Example 22

N-tert-butyl-5-bromo-3-(1-(4-cyclopropyl-2,3-difluorophenyl)-1H-tetrazol-5-yl)pyridin-2-amine

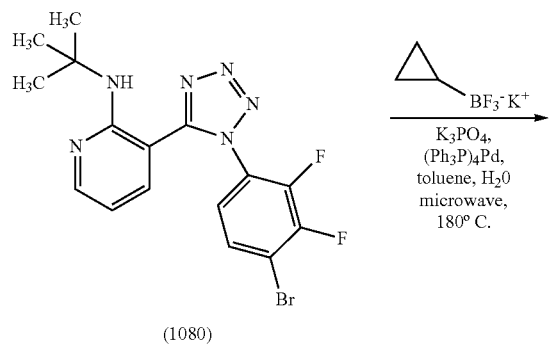

(1080)

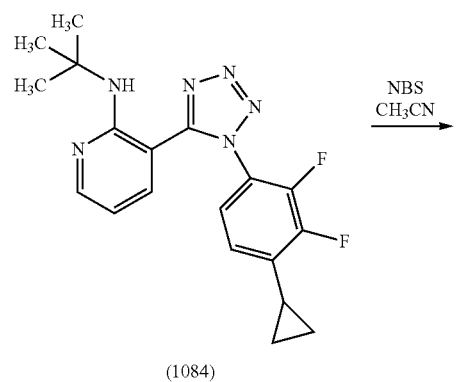

(1084)

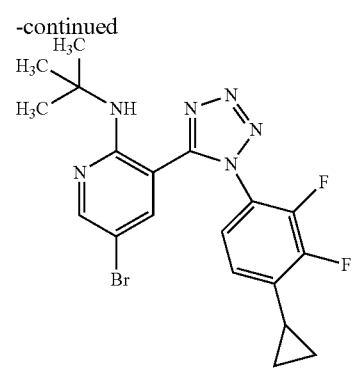

(1085)

N-tert-Butyl-3-(1-(4-bromo-2,3-difluorophenyl)-1H-tetrazol-5-yl)pyridin-2-amine (Compound 1080 150 mg, 0.366 mmol), potassium cyclopropyltrifluoroborate (70.5 mg, 0.476 mmol), tricyclohexylphosphine (10 mg, 0.0366 mmol) and K$_3$PO$_4$ (272 mg, 1.283 mmol) were taken into toluene (1.5 ml), and water (750 µL). The reaction was degassed with nitrogen for 1 hour and Pd(OAc)$_2$ (4.1 mg, 0.0183 mmol) was added. The reaction mixture was heated at 180° C. for 10 minutes under microwave irradiation. The reaction was found to be incomplete by HPLC analysis so tetrakis-(triphenylphosphine) palladium (0) (42 mg, 0.0366 mmol) was added to the mixture and microwave irradiation was continued for 10 minutes at 180° C. The reaction mixture was poured in water and extracted with ethyl acetate. The organic layer was dried over anhydrous sodium sulfate, filtered, and the volatiles removed under reduced pressure to afford a crude brown oil, which was purified by column chromatography (SiO$_2$), eluting with 0-20% EtOAc/hexanes, to afford 120 mg of N-tert-butyl-3-(1-(4-cyclopropyl-2,3-difluorophenyl)-1H-tetrazol-5-yl)pyridin-2-amine (Compound 1084) as a colorless oil; ESMS (M+1)=371.

Compound 1084 (200 mg, 0.54 mmol) was dissolved in 10 mL of acetonitrile. N-Bromosuccinimide (96 mg, 0.54 mmol) was added to the solution and the reaction mixture was stirred at room temperature for 30 minutes. The reaction was quenched with 1 M Na$_2$S$_2$O$_3$ and the mixture extracted with ethyl acetate. The organice layer was dried over anhydrous sodium sulfate, filtered, and concentrated under reduced pressure to afford a white solid that was purified by silica gel chromatography to afford 37 mg of N-tert-butyl-5-bromo-3-(1-(4-cyclopropyl-2,3-difluorophenyl)-1H-tetrazol-5-yl)pyridin-2-amine (Compound 1085); MS (M+1)=449.

Example 23

5-bromo-3-(1-(2,3-difluoro-4-alkoxyphenyl)-1H-tetrazol-5-yl)pyridin-2-amines

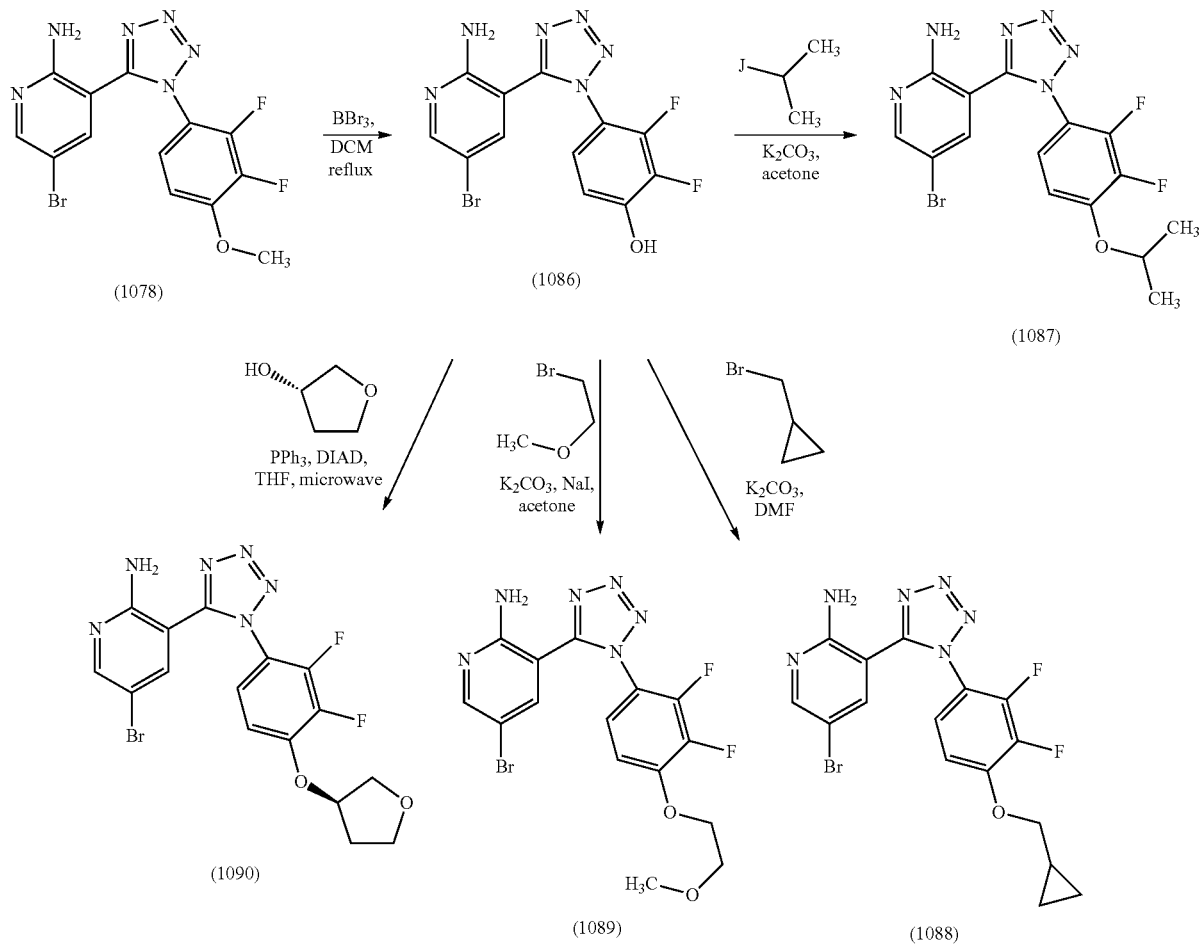

To a suspension of 5-Bromo-3-(1-(2,3-difluoro-4-methylphenyl)-1H-tetrazol-5-yl)pyridin-2-amine (Compound 1078, 5.0 g, 13.1 mmol) in DCM (100 mL) was added BBr₃ (10 mL, 130 mmol) under nitrogen. The reaction mixture was refluxed for 3 h at 45° C. After cooling to 0° C., the reaction was carefully quenched with H₂O (20 mL) and satd' NaHCO₃ solution (50 mL). The resulting precipitate was collected by vacuum filtration and dried under vacuum. The organic layer was dried over Na₂SO₄ and concentrated under vacuum to yield additional product as a solid. The combined solids were purified by silica gel chromatography (0-10% MeOH/DCM) to afford 4-(5-(2-amino-5-bromopyridin-3-yl)-1H-tetrazol-1-yl)-2,3-difluorophenol (Compound 1086, 3 g, yield 62%) as an off white solid.

To a solution of Compound 1086 (0.5 g, 1.36 mmol) in acetone (10 mL) was added 2-iodopropane (340 mg, 2 mmol) and K₂CO₃ (276 mmg, 2 mmol). The reaction mixture was stirred for 24 h at room temperature. The inorganic solids were removed by vacuum filtration and the filtrate was diluted with EtOAc, washed with brine, dried over Na₂SO₄, and concentrated under vacuum. The residue was purified by silica gel chromatography (10-50% EtOAc/hexanes) to afford 5-bromo-3-(1-(2,3-difluoro-4-isopropoxyphenyl)-1H-tetrazol-5-yl)pyridin-2-amine (Compound 1087, 335 mg, 60% yield) as a colorless solid.

Compound 1086 (100 mg, 0.271 mmol), potassium carbonate (130 mg, 0.941 mmol), and (bromomethyl)cyclopropane (43.9 mg, 0.325 mmol) were stirred in dimethylformamide (2 mL) at ambient temperature over 12 hours. The reaction was poured over brine and extracted two times with ethyl acetate. The organic layers were dried over sodium sulfate, filtered, and the solvent was removed under vacuum. The residue was purified by silica gel chromatography, eluting with 50% EtOAc//hexanes. 5-Bromo-3-(1-(4-(cyclopropylmethoxy)-2,3-difluorophenyl)-1H-tetrazol-5-yl)pyridin-2-amine (Compound 1088, 44 mg, 38% yield) was isolated as pale yellow glass; ESMS (M+H)=425.23.

To a stirred suspension of Compound 1086 (300 mg, 0.8127 mmol), potassium carbonate (224.6 mg, 1.625 mmol), and 2-bromoethyl methyl ether (169.4 mg, 114.5 µL, 1.219 mmol) was added sodium iodide (182.7 mg, 1.219 mmol). The reaction mixture was heated to 50° C. and allowed to stir overnight. After cooling, the mixture was partioned between EtOAc and water. The organics were with brine, dried over sodium sulfate, and the volatiles removed in vacuo. Purification by silica gel chromatography (0-50% gradient of EtOAc/hexanes) gave 3-(1-(4-(2-methoxyethoxy)-2,3-difluorophenyl)-1H-tetrazol-5-yl)-5-bromopyridin-2-amine (Compound 1089, 120 mg).

A solution of Compound 1086 (90 mg, 0.2438 mmol), triphenylphosphine (76.74 mg, 0.2926 mmol), diisoproplyazodicarboxylate (59.17 mg, 56.68 μL, 0.2926 mmol), and (S)-tetrahydrofuran-3-ol (25.78 mg, 0.2926 mmol) in THF (90 μL) was heated at 70° C. for 10 minutes under microwave irradiation. The reaction was quenched with ammonium chloride (satd') and extracted with EtOAc. The organics were washed with 1 M NaOH (2×), brine, dried over sodium sulfate, and concentrated under vacuum. The residue was chromatographed over silica gel (0-50% EtOAc/hexanes gradient) to give 3-(1-(4-((R)-tetrahydrofuran-3-yloxy)-2,3-difluorophenyl)-1H-tetrazol-5-yl)-5-bromopyridin-2-amine (Compound 1090, 99 mg).

This procedure was also used to produce 5-bromo-3-(1-(2,3-difluoro-4-ethoxyphenyl)-1H-tetrazol-5-yl)pyridin-2-amine (Compound 1091) and 5-bromo-3-(1-(2,3-difluoro-4-propoxyphenyl)-1H-tetrazol-5-yl)pyridin-2-amine (Compound 1092) when alkylating phenol intermediate Compound 1086 with ethyl iodide and propyl iodide, respectively.

Example 24

Bis-tert-Butyl 5-bromo-3-(1-(2,3-difluoro-4-(alkoxymethyl)phenyl)-1H-tetrazol-5-yl)pyridin-2-ylcarbamate

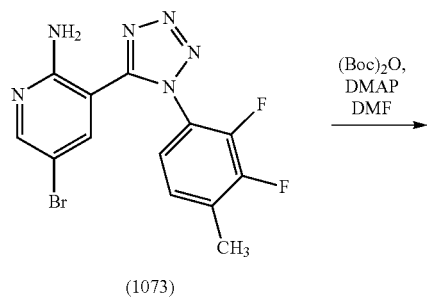

(1073)

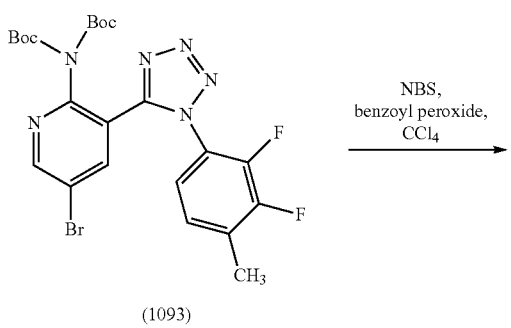

(1093)

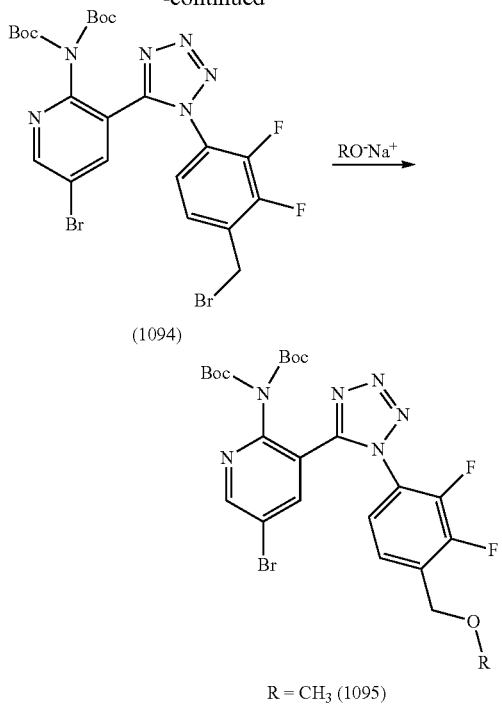

R = CH₃ (1095)
R = CH₂CH₃ (1096)
R = CH(CH₃)₂ (1097)

5-Bromo-3-(1-(2,3-difluoro-4-methylphenyl)-1H-tetrazol-5-yl)pyridin-2-amine (1.5 g, 4.086 mmol, 1 eq.) (Compound 1073) was diluted in DMF (20 mL). Di-tert-Butyl dicarbonate (3.121 g, 14.3 mmol, 3.5 eq.) and N,N-dimethylpyridin-4-amine (DMAP) (0.175 g, 1.143 mmol, 0.35 eq.) were added to the solution and the mixture stirred at room temperature overnight under an atmosphere of nitrogen. The reaction mixture was diluted with diethyl ether (50 mL), washed with saturated sodium bicarbonate (50 mL), and extracted with additional diethyl ether (2×50 mL). The combined organics were washed with water (3×50 mL), dried ($Na_2SO_4$), and concentrated under reduced pressure. The resulting oil was diluted in methylene chloride and filtered through a plug of silica to give bis-tert-Butyl 5-bromo-3-(1-(2,3-difluoro-4-methylphenyl)-1H-tetrazol-5-yl)pyridin-2-ylcarbamate (Compound 1093, 2.3 g, 4.054 mmol, 99.2% yield); $^1$H NMR (300 MHz, $CDCl_3$) δ 8.7 (d, J=2.4 Hz, 1H), 7.92 (d, J=2.4 Hz, 1H), 7.2 (m, 1H), 7.1 (m, 1H), 2.4 (d, J=2.1 Hz, 3H), 1.35 (m, 18H).

Compound 1093 (2.3 g, 4.054 mmol, 1 eq.) was diluted in $CCl_4$ (65 mL). NBS (200 mg, 1.124 mmol, 0.28 eq.) and benzoyl peroxide (196.4 mg, 0.811 mmol, 0.2 eq.) were added and the reaction was stirred at 80° C. under an atmosphere of nitrogen. NBS (594 mg, 3.34 mmol, 0.82 eq.) was added in 4 equal parts over the next 4 hours (a total of 794 mg, 4.46 mmol, 1.1 eq. was added) and the reaction was stirred at 80° C. overnight. The mixture was concentrated under reduced pressure and purified by silica gel chromatography, eluting with EtOAc/hexanes to give bis-tert-Butyl 5-bromo-3-(1-(4-(bromomethyl)-2,3-difluorophenyl)-1H-tetrazol-5-yl)pyridin-2-ylcarbamate (Compound 1094, 1.67 g, 2.58 mmol, 45% yield) with 70% purity (30% impurity of Compound 1093); $^1$H NMR (300 MHz, $CDCl_3$): δ 8.7 (d, J=2.4 Hz, 1H), 7.9 (d, J=2.4 Hz, 1H), 7.3 (m, 2H), 4.5 (d, J=1.3 Hz, 2H), 1.35 (m, 18H). This material was used without further purification.

Dry sodium methoxide (76.9 mg, 1.423 mmol, 3 eq.) was diluted in anhydrous MeOH (6 mL). The suspension was added to a solution of Compound 1094 (511 mg, 0.474 mmol, 1 eq.) in MeOH (6 mL). The suspension was stirred under $N_2$ at room temperature overnight, concentrated under reduced pressure, diluted in methylene chloride, and purified using chromatography using EtOAc/hexanes to give bis-tert-Butyl 5-bromo-3-(1-(2,3-difluoro-4-(methoxymethyl)phenyl)-1H-tetrazol-5-yl)pyridin-2-ylcarbamate (Compound 1095, 137 mg, 0.229 mmol, 48% yield). $^1$H NMR (300 MHz, CDCl$_3$) δ 8.7 (d, J=2.4 Hz, 1H), 7.9 (d, J=2.4 Hz, 1H), 7.35 (m, 2H), 4.6 (d, J=1.0 Hz, 2H), 3.45 (s, 3H), 1.35 (m, 18H).

In procedures analogous to the reaction of Compound 1094 with sodium methoxide, Compound 1094 was reaction with sodium ethoxide in ethanol to produce Compound 1096 [$^1$H NMR (300 MHz, CDCl$_3$) δ 8.7 (d, J=2.4 Hz, 1H), 7.94 (d, J=2.4 Hz, 1H), 7.4 (m, 1H), 7.33 (m, 1H), 4.62 (m, 2H), 3.6 (q, J=7.0 Hz, 2H), 1.35 (m, 18H), 1.25 (m, 3H)] and with sodium isopropoxide in isopropanol to produce Compound 1097 [$^1$H NMR (300 MHz, CDCl$_3$): δ 8.6 (m, 1H), 7.6 (m, 1H), 7.45 (m, 1H), 7.35 (m, 1H), 4.67 (m, 2H), 3.75 (m, 1H), 1.4 (m, 18H), 1.25 (m, 6H)].

Example 25 tert-Butyl 4-(4-(4,4,5,5-tetramethyl-1,3,2-dioxaborolan-2-yl)-1H-pyrazol-1-yl)piperidine-1-carboxylate

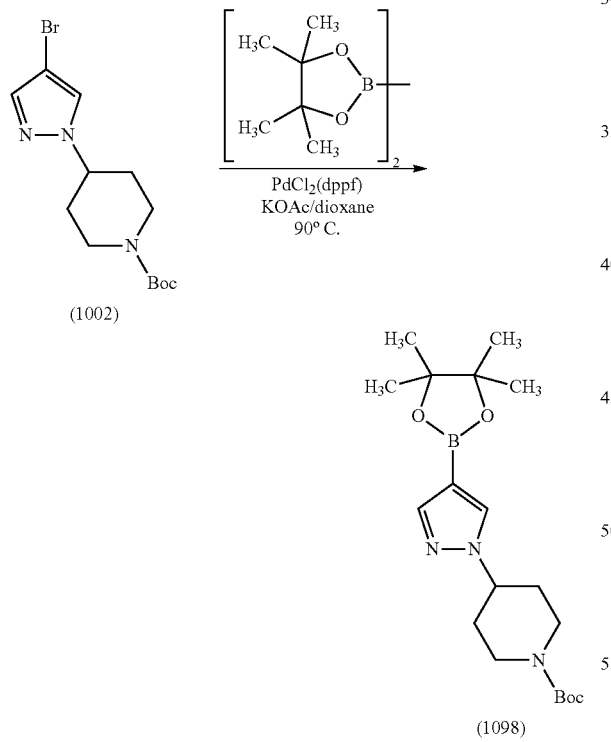

tert-Butyl 4-(4-bromo-1H-pyrazol-1-yl)piperidine-1-carboxylate (Compound 1002, 10.52 g, 31.86 mmol), 4,4,5,5-tetramethyl-2-(4,4,5,5-tetramethyl-1,3,2-dioxaborolan-2-yl)-1,3,2-dioxaborolane (9.71 g, 38.23 mmol), and potassium acetate 9.38 g, 95.58 mmol) was taken into 105 ml of 1,4-dioxane. The mixture was degassed by bubbling nitrogen for 20 minutes followed by the addition of PdCl$_2$ (dppf) CH$_2$Cl$_2$ (1.3 g, 1.59 mmol). The reaction was heated at 90° C. for 11 hours. The reaction was cooled to room temperature and filtered through a plug of Florisil, rinsing with ethyl acetate. The filtrate was concentrated in vacuo to afford a dark brown oil that was dissolved in hexanes and eluted through a 2$^{nd}$ plug of Florisil with 2:1 Hexanes/Ethyl acetate. The filtrate was concentrated in vacuo to give a tan oil that was triturated with hexanes and stirred at 0° C. until a white precipitate formed. The precipitate was collected by vacuum filtration, washed with hexanes and dried to afford 6.79 g of tert-Butyl 4-(4-(4,4,5,5-tetramethyl-1,3,2-dioxaborolan-2-yl)-1H-pyrazol-1-yl)piperidine-1-carboxylate (Compound 1098).

Example 26

3-(1-(2,3-Difluoro-4-methoxyphenyl)-1H-tetrazol-5-yl)-5-(1-((R)-piperidin-3-yl)-1H-pyrazol-4-yl)pyridin-2-amine (Compound 8)

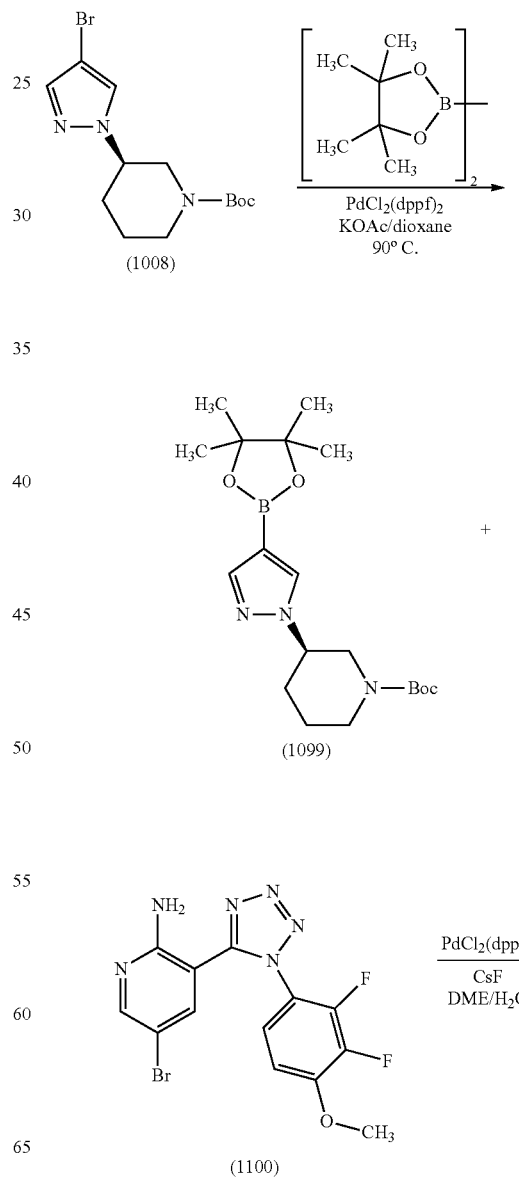

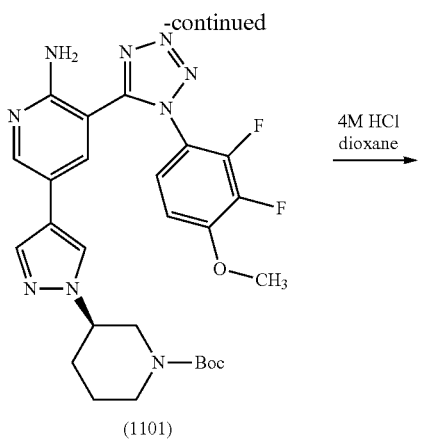

(1101)

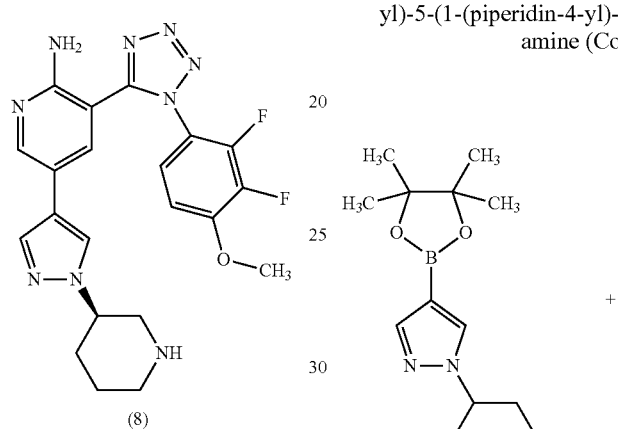

(8)

In a procedure similar to that for the preparation of Compound 1098 in Example 25, Compound 1008 was converted to (S)-tert-Butyl 3-(4-(4,4,5,5-tetramethyl-1,3,2-dioxaborolan-2-yl)-1H-pyrazol-1-yl)piperidine-1-carboxylate (Compound 1099).

A solution of (S)-tert-Butyl 3-(4-(4,4,5,5-tetramethyl-1,3,2-dioxaborolan-2-yl)-1H-pyrazol-1-yl)piperidine-1-carboxylate (Compound 1099, 642 mg, 1.70 mmol), 5-bromo-3-(1-(2,3-difluoro-4-methoxyphenyl)-1H-tetrazol-5-yl)pyridin-2-amine (Compound 1100, 543 mg, 1.418 mmol), and CsF (1.5 M, 2.84 mL, 4.26 mmol) in 7 mL DMF was degassed with nitrogen for 30 minutes, at which point 1,1'-Bis(diphenylphosphino)ferrocene]palladium dichloride (174 mg, 0.212 mmol) was added and the mixture was degassed an additional 15 minutes before heating to 120° C. under an atmosphere of nitrogen. After 1 hour, LCMS analysis indicated that the reaction was complete. Methylene chloride (10 mL) and satd' aqueous sodium bicarbonate (10 mL) were added, and the reaction mixture extracted with methylene chloride (2×10 mL), the combined organics concentrated under reduced pressure, and the residue purified via silica gel chromatography (50-100% ethyl acetate in hexanes) to give (S)-tert-Butyl 3-(4-(6-amino-5-(1-(2,3-difluoro-4-methoxyphenyl)-1H-tetrazol-5-yl)pyridin-3-yl)-1H-pyrazol-1-yl)piperidine-1-carboxylate (Compound 1101) as a yellow solid; $^1$H NMR (300 MHz, CDCl$_3$) δ 8.25 (d, J=2.0 Hz, 1H), 7.34 (d, J=8.8 Hz, 1H), 7.25-7.16 (m, 2H), 6.94-6.88 (m, 2H), 6.31 (s, 2H), 4.15-4.01 (m, 1H), 3.96 (s, 3H), 3.28 (d, J=11.5 Hz, 1H), 2.98-2.81 (m, 2H), 2.62 (dd, J=2.7, 22.8 Hz, 1H), 2.62 (s, 1H), 2.14-2.10 (m, 1H), 1.97-1.73 (m, 1H), 1.62 (s, 9H) and 1.57-1.47 (m, 1H) ppm.

Compound 1101 (61 mg, 0.110 mmol) was dissolved in methanol (1 mL) and HCl in dioxane (275 µL, 4.0 M, 1.10 mmol) was added. The reaction was stirred at room temperature for 2 hours and ethyl ether was added. The resulting precipitate was collected and converted to the free base form by treatment with ammonium hydroxide and methylene chloride. The reaction was filtered through diatomaceous earth with the aid of methylene chloride, concentrated, and 2 equiv. of 4.0 M HCl in dioxane was added to give the HCl salt of (S)-3-(1-(2,3-Difluoro-4-methoxyphenyl)-1H-tetrazol-5-yl)-5-(1-(piperidin-3-yl)-1H-pyrazol-4-yl)pyridin-2-amine as a yellow solid (Compound 8, 50.5 mg, 93% yield).

Example 27

3-(1-(2,3-Difluoro-4-methylphenyl)-1H-tetrazol-5-yl)-5-(1-(piperidin-4-yl)-1H-pyrazol-4-yl)pyridin-2-amine (Compound 11)

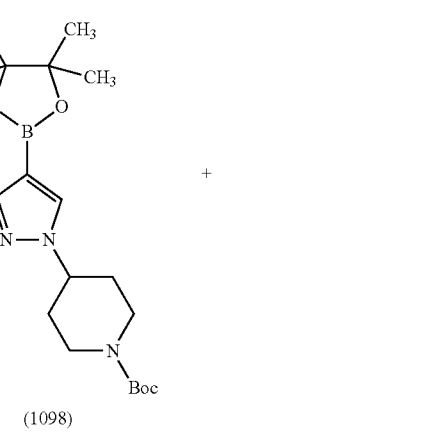

(1098)

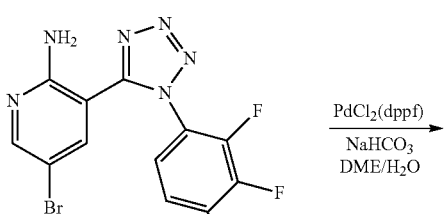

(1073)

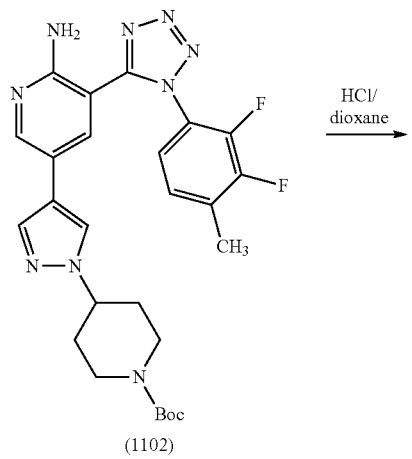

(1102)

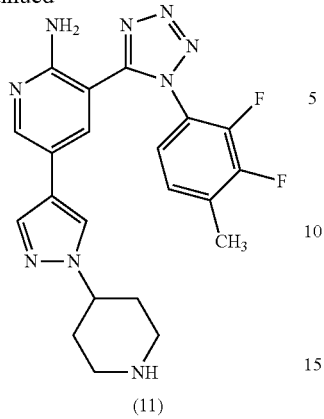

(11)

A round-bottom flask was charged with 5-bromo-3-(1-(2,3-difluoro-4-methylphenyl)-1H-tetrazol-5-yl)pyridin-2-amine (Compound 1073, 3.672 g, 10 mmol), tert-butyl 4-(4-(4,4,5,5-tetramethyl-1,3,2-dioxaborolan-2-yl)-1H-pyrazol-1-yl)piperidine-1-carboxylate (Compound 1098, 4.150 g, 11.00 mmol) and DME (100 mL) was bubbled with nitrogen gas for 20 min. A 1.2 M aqueous solution of sodium bicarbonate (25.00 mL, 30.00 mmol) was added and nitrogen flow was continued for another 40 min before addition of PdCl$_2$(dppf)$_2$ (731.7 mg, 1.000 mmol). The suspension was heated at 70° C. for 15 hours, filtered though a layer of diatomaceous earth, and the filtrate washed with brine. The volatiles were removed by vacuum evaporation to afford a residue that was purified by silica gel chromatography, eluting with 20-100% EtOAc/hexanes, to produce tert-butyl 4-(4-(6-amino-5-(1-(2,3-difluoro-4-methylphenyl)-1H-tetrazol-5-yl)pyridin-3-yl)-1H-pyrazol-1-yl)piperidine-1-carboxylate as a yellow solid (Compound 1102, 4.0 g, 74%).

tert-Butyl 4-(4-(6-amino-5-(1-(2,3-difluoro-4-methylphenyl)-1H-tetrazol-5-yl)pyridin-3-yl)-1H-pyrazol-1-yl)piperidine-1-carboxylate (Compound 1102, 3.5 g, 6.511 mmol) was treated with 4.0 M HCl/dioxane (50 mL, 200.0 mmol) for 1 h at RT. The precipitate was collected by filtration and dried under vacuum to give 3-(1-(2,3-difluoro-4-methylphenyl)-1H-tetrazol-5-yl)-5-(1-(piperidin-4-yl)-1H-pyrazol-4-yl)pyridin-2-amine dihydrochloride salt (Compound 11, 3.3 g, 99%) as a slightly yellow solid.

Example 28

3-(1-(2,3-difluoro-4-methoxyphenyl)-1H-tetrazol-5-yl)-5-(1-(piperidin-4-yl)-1H-pyrazol-4-yl)pyridin-2-amine, dihydrochloride salt (Compound 12)

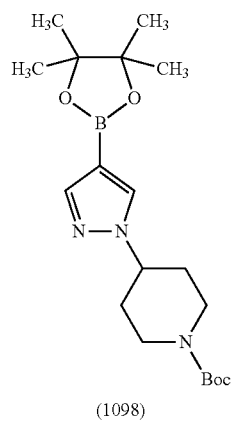

(1098)

+

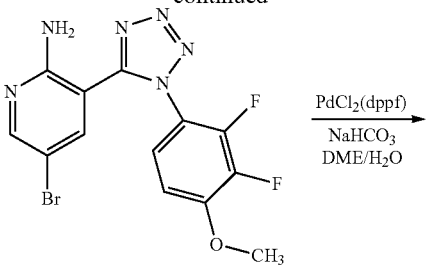

(1078)

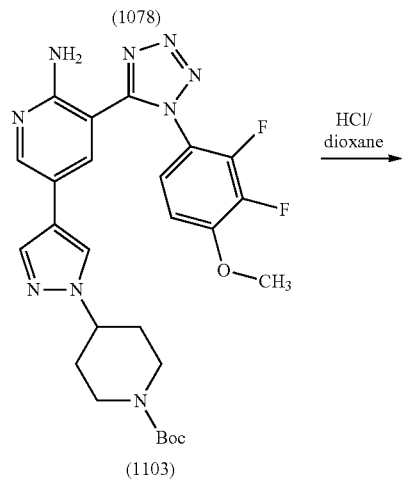

(1103)

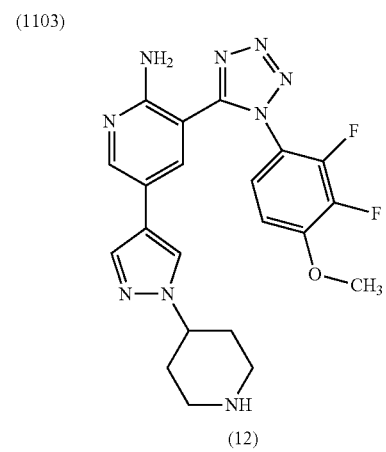

(12)

To a round-bottom flask charged with 5-bromo-3-(1-(2,3-difluoro-4-methoxyphenyl)-1H-tetrazol-5-yl)pyridin-2-amine (Compound 1078, 3.832 g, 10 mmol), tert-butyl 4-(4-(4,4,5,5-tetramethyl-1,3,2-dioxaborolan-2-yl)-1H-pyrazol-1-yl)piperidine-1-carboxylate (Compound 1098, 4.150 g, 11.00 mmol) and DME (100 mL) was flushed with N$_2$ for 20 min. An aqueous solution of sodium bicarbonate (25 mL of 1.2 M, 30.00 mmol) was added. Nitrogen flow was continued for another 40 min before the addition of PdCl$_2$ dppf (731.7 mg, 1.00 mmol). The resulting suspension was heated at 70° C. for 15 hours, filtered though a layer of diatomaceous earth, and washed with brine. The volatiles were removed in vacuo to afford a residue, which was purified by silica gel chromatography, eluting with 20-100% EtOAc/hexanes to yield tert-butyl 4-(4-(6-amino-5-(1-(2,3-difluoro-4-methoxyphenyl)-1H-tetrazol-5-yl)pyridin-3-yl)-1H-pyrazol-1-yl)piperidine-1-carboxylate (Compound 1103, 2.8 g, 50.6%) as yellow solid; ESMS (M+H)=554.

Compound 1103 (3.0 g, 5.419 mmol) was treated with 4 M HCl/dioxane (50 mL, 200.0 mmol) for 1 hour at RT. The solvents were removed by vacuum evaporation to give 3-(1-(2,3-difluoro-4-methoxyphenyl)-1H-tetrazol-5-yl)-5-(1-(piperidin-4-yl)-1H-pyrazol-4-yl)pyridin-2-amine, dihydrochloride salt (Compound 12, 2.8 g, 98%) as a slightly yellow solid.

Example 29

3-(1-(2,3-Difluoro-4-methylphenyl)-1H-tetrazol-5-yl)-5-(5,6,7,8-tetrahydro-4H-thieno[2,3-d]azepin-2-yl)pyridin-2-amine (Compound 13)

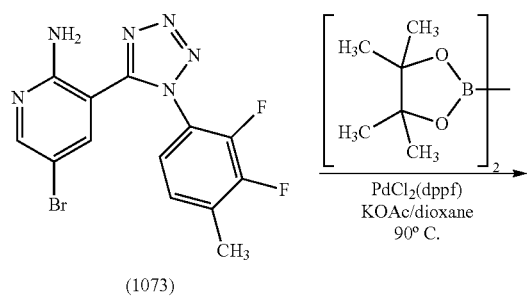

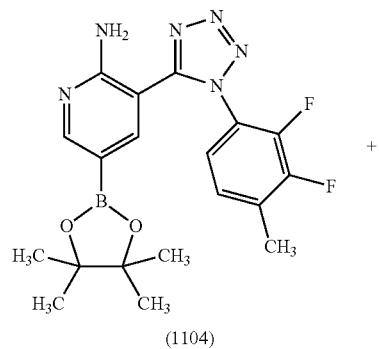

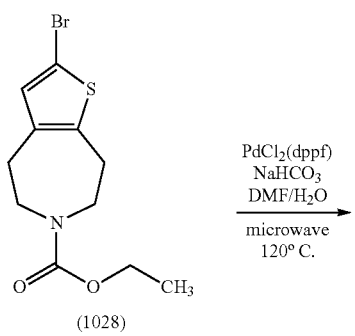

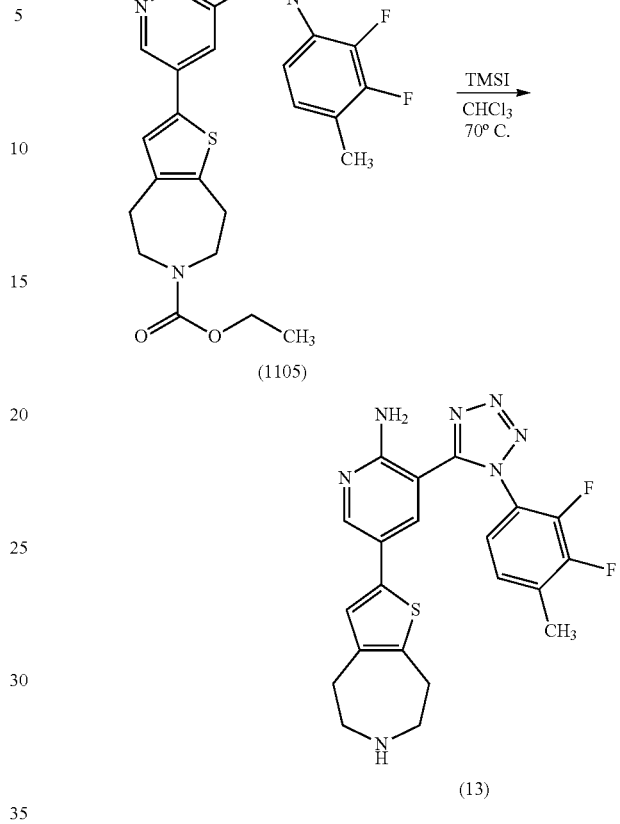

In a procedure similar to that for the preparation of Compound 1098 in Example 25, Compound 1073 was converted to 3-(1-(2,3-difluoro-4-methylphenyl)-1H-tetrazol-5-yl)-5-(4,4,5,5-tetramethyl-1,3,2-dioxaborolan-2-yl)pyridin-2-amine (Compound 1104).

To a solution of 3-(1-(2,3-difluoro-4-methylphenyl)-1H-tetrazol-5-yl)-5-(4,4,5,5-tetramethyl-1,3,2-dioxaborolan-2-yl)pyridin-2-amine (Compound 1104, 3 g, 7.243 mmol) in DMF (50 mL) was added ethyl 2-bromo-7,8-dihydro-4H-thieno[2,3-d]azepine-6 (5H)-carboxylate (Compound 1028, 2.644 g, 8.692 mmol) and saturated sodium bicarbonate (39.10 g, 18.11 mL of 1.2 M, 21.73 mmol); The mixture suspension was stirred under nitrogen atmosphere for 20 min; $PdCl_2(dppf)_2$ (530.0 mg, 0.724 mmol) was added and the suspension heated at 90° C. under an atmosphere of nitrogen for 14 hour. After cooling, the reaction mixture was poured into an aqueous $NaHCO_3$ solution, and the resulting solid collected by filtration and washed with water. The resulting crude dark solid was dissolved in EtOAc, co-evaporated with silica gel, and purified by medium pressure silica gel chromatography, eluting with 5% to 55% EtOAc/hexanes, to afford ethyl 2-(6-amino-5-(1-(2,3-difluoro-4-methylphenyl)-1H-tetrazol-5-yl)pyridin-3-yl)-7,8-dihydro-4H-thieno[2,3-c]azepine-6(5H)-carboxylate (Compound 1105, 1.9 g, 51% yield) as a yellow solid. ESMS (M+H)=512.5.

To a solution of compound 1105 (1.9 g, 3.714 mmol) in dry chloroform (30 mL) was added trimethylsilyl iodide (TMSI, 5.285 mL, 37.14 mmol). The solution was heated at 70° C. for 14 hrs, cooled to RT, and the reaction quenched by adding MeOH carefully. 2M NaOH was then added and the mixture was poured into a saturated $NaHCO_3$ solution and extracted with DCM. The combined DCM solution was extracted with 2M HCl and the acidic aqueous solution basified with 6M NaOH. The precipitate was filtered; washed with water and dissolved in small amount of MeOH. 6M HCl was added to the methanolic solution, the solvent evaporated, the residue dissolved in methanol and then poured into ether; The yellow precipitate was collected and dried as yellow solid to produce 3-(1-(2,3-difluoro-4-methylphenyl)-1H-tetrazol-5-yl)-5-(5,6,7,8-tetrahydro-4H-thieno[2,3-d]azepin-2-yl)pyridin-2-amine (Compound 13, 1.67 g, 94% yield).

Example 30

3-(1-(2,3-Difluoro-4-methoxyphenyl)-1H-tetrazol-5-yl)-5-(4-methyl-5-(piperidin-4-yl)thiophen-2-yl)pyridin-2-amine (Compound 22)

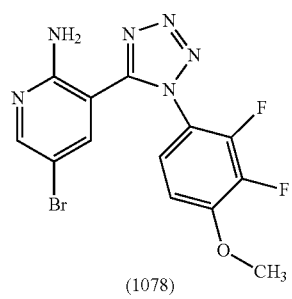
(1078)

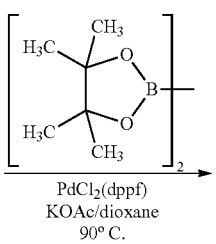

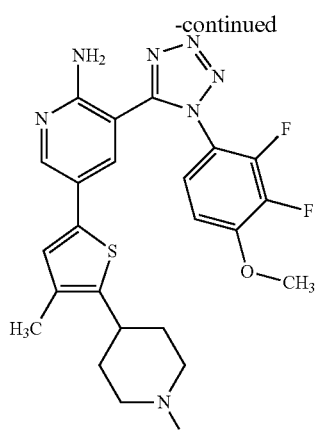
(1107)

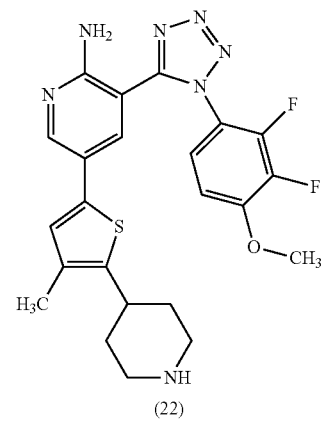
(22)

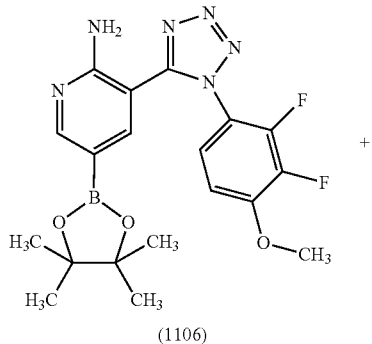
(1106)

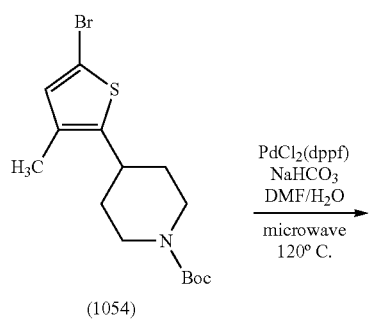
(1054)

In a procedure similar to that for the preparation of Compound 1098 in Example 25, Compound 1078 was converted to 3-(1-(2,3-difluoro-4-methoxyphenyl)-1H-tetrazol-5-yl)-5-(4,4,5,5-tetramethyl-1,3,2-dioxaborolan-2-yl)pyridin-2-amine (Compound 1106).

To a solution of 3-(1-(2,3-difluoro-4-methoxyphenyl)-1H-tetrazol-5-yl)-5-(4,4,5,5-tetramethyl-1,3,2-dioxaborolan-2-yl)pyridin-2-amine (Compound 1106, 200 mg, 0.4649 mmol) and tert-butyl 4-(5-bromo-3-methylthiophen-2-yl)piperidine-1-carboxylate (Compound 1054, 167.5 mg, 0.4650 mmol) in DMF (8 mL) was added a solution of NaHCO₃ (2.509 g, 1.162 mL of 1.2 M, 1.395 mmol). The mixture was degassed under a nitrogen stream for 20 minutes. PdCl₂(dppf) (34.02 mg, 0.04650 mmol) was added and the reaction was stirred for 10 minutes at 120° C. under microwave irradiation. The mixture was diluted with EtOAc, filtered, and the filtrate was washed with water. The organics were dried over magnesium sulfate, concentrated, and the resulting residue purified via silica gel chromatography to give tert-butyl 4-(5-(6-amino-5-(1-(2,3-difluoro-4-methoxyphenyl)-1H-tetrazol-5-yl)pyridin-3-yl)-3-methylthiophen-2-yl)piperidine-1-carboxylate (Compound 1107, 230 mg, 83%) as a yellow solid.

To Compound 1107 (100 mg, 0.17 mmol) was added 4 mL of 4.0 N HCl in dioxane. The reaction was stirred at room temperature for 2 hours and concentrated under reduced pressure. The resulting yellow residue was dissolved in a minimum of MeOH and precipitated with cold Et₂O. The yellow solids were filtered and dried to provide 3-(1-(2,3-difluoro-4-methoxyphenyl)-1H-tetrazol-5-yl)-5-(4-methyl-5-(piperidin-4-yl)thiophen-2-yl)pyridin-2-amine (Compound 22, 80 mg, 98%) as a yellow solid.

TABLE 2

Analytical Chararacterization Data for Compounds of Formula I (blank cells indicate that the test was not performed)

| Cmpnd. No. | MS (M + H) | $^1$H-NMR (400 MHz, unless indicated otherwise) NMR peaks given as δ values in ppm |
|---|---|---|
| 1 |  | (DMSO-d$_6$): 9.95 (br. s, exchanged with D$_2$O, 1H), 9.63 (br. s, exchanged with D$_2$O, 1H), 8.55 (s, 1H), 8.37 (s, 1H), 8.31 (s, 1H), 7.90 (s, 1H), 7.58 (br. t, J = 7.6 Hz, 1H), 7.42 (t, J = 7.2 Hz, 1H), 5.15-5.14 (m, 1H), 3.66-3.48 (m, 2H), 3.41-3.35 (m, 2H), 2.45-2.38 (m, 1H), 2.35 (s, 3H), 2.29-2.23 (m, 1H) |
| 2 | 438.20 | (DMSO-d$_6$): 8.45 (d, J = 2.4 Hz, 1H), 8.14 (s, 1H), 7.89 (d, J = 2.4 Hz, 1H), 7.73 (s, 1H), 7.56 (t, J = 7.2 Hz, 1H), 7.42 (t, J = 7.6 Hz, 1H), 4.60-4.50 (m, 1H), 3.52-3.50 (m, 1H), 3.25-3.23 (m, 2H), 2.93-2.90 (m, 1H), 2.35 (s, 3H), 2.16-2.13 (m, 1H), 2.01-1.83 (m, 3H) |
| 3 | 452.40 | (DMSO-d$_6$): 8.41 (s, 1H), 8.12 (s, 1H), 8.09 (s, 1H), 7.78 (s, 1H), 7.55 (t, J = 7.6 Hz, 1H), 7.40 (t, J = 8.0 Hz, 1H), 4.57-4.50 (m, 1H), 3.30-3.10 (m, 4H), 2.35 (s, 3H), 2.30-2.26 (m, 2H), 2.18-2.14 (m, 1H), 2.07-1.79 (m, 3H) |
| 4 | 440.20 | (DMSO-d$_6$): 8.47 (d, J = 2.4 Hz, 1H), 8.20 (s, 1H), 8.03 (s, 1H), 7.84 (s, 1H), 7.66 (td, J = 8.0, 2.4 Hz, 1H), 7.33 (br. t, J = 8.0 Hz, 1H), 5.18-5.10 (m, 1H), 3.98 (m, 3H), 3.65-3.61 (m, 1H), 3.50-3.49 (m, 1H), 3.39-3.36 (m, 2H), 2.45-2.35 (m, 1H), 2.29-2.21 (m, 1H) |
| 5 |  | (DMSO-d$_6$): 8.45 (s, 1H), 8.22 (s, 1H), 8.12 (s, 1H), 7.80 (s, 1H), 7.55 (t, J = 7.6 Hz, 1H), 7.41 (t, J = 7.6 Hz, 1H), 4.64-4.59 (m, 1H), 3.51-3.48 (m, 1H), 3.25-3.17 (m, 2H), 2.91-2.89 (m, 1H), 2.35 (s, 3H), 2.17-2.14 (m, 1H), 1.98-1.91 (m, 3H) |
| 6 | 440.10 | (DMSO-d$_6$): 9.63 (s, exchanged with D$_2$O, 1H), 9.40 (s, exchanged with D$_2$O, 1H), 8.48 (s, 1H), 8.28 (s, 1H), 8.01 (s, 1H), 7.82 (s, 1H), 7.65 (t, J = 8.0 Hz, 1H), 7.33 (t, J = 8.0 Hz, 1H), 5.14-5.13 (m, 1H), 3.95 (s, 3H), 3.65-3.60 (m, 1H), 3.51-3.50 (m, 1H), 3.40-3.36 (m, 2H), 2.45-2.35 (m, 1H), 2.28-2.25 (m, 1H) |
| 7 |  | (DMSO-d$_6$): 9.92 (br. s, exchanged with D$_2$O, 1H), 9.61 (br. s, exchanged with D$_2$O, 1H), 8.55 (d, J = 2.4 Hz, 1H), 8.37 (s, 1H), 8.28 (s, 1H), 7.89 (s, 1H), 7.58 (t, J = 7.2 Hz, 1H), 7.42 (t, J = 7.6 Hz, 1H), 5.16-5.14 (m, 1H), 3.66-3.62 (m, 1H), 3.50-3.45 (m, 1H), 3.40-3.35 (m, 2H) 2.45-2.38 (m, 1H), 2.35 (s, 3H), 2.29-2.21 (m, 1H) |
| 8 | 454.20 | (DMSO-d$_6$): 9.73 (s, exchanged with D$_2$O, 1H), 9.45 (s, exchanged with D$_2$O, 1H), 8.56 (s, 1H), 8.35 (s, 2H), 7.89 (s, 1H), 7.65 (t, J = 8 Hz, 1H), 7.31 (t, J = 8.4 Hz, 1H), 4.67-4.61 (m, 1H), 3.95 (s, 3H), 3.49 (br. d, J = 10.8 Hz, 1H), 3.26-3.16 (br. m, 2H), 2.89-2.80 (m, 1H), 2.16 (br. d, J = 10.8 Hz, 1H), 1.99-1.90 (m, 3H) |
| 9 | 468.20 | (DMSO-d$_6$): 9.35-9.29 (m, exchanged with D$_2$O, 2H), 8.52 (s, 1H), 8.25-8.21 (m, 2H), 7.79 (s, 1H), 7.64 (t, J = 7.6 Hz, 1H), 7.32 (t, J = 8.4 Hz, 1H), 4.54-4.50 (m, 1H), 3.95 (s, 3H), 3.27-3.06 (m, 4H), 2.29-2.26 (m, 2H), 2.18-2.14 (m, 1H), 2.08-1.94 (m, 2H), 1.88-1.83 (m, 1H) |
| 10 | 454.20 | (DMSO-d$_6$): 9.86-9.80 (m, exchanged with D$_2$O, 1H), 9.56 (d, J = 8.8 Hz, exchanged with D$_2$O, 1H), 8.59 (d, J = 2.4 Hz, 1H), 8.42 (d, J = 2 Hz, 1H), 8.38 (s, 1H), 7.91 (s, 1H), 7.67 (t, J = 7.6 Hz, 1H), 7.32 (t, J = 8.4 Hz, 1H), 4.69-4.64 (m, 1H), 3.97 (s, 3H), 3.49 (d, J = 10.8 Hz, 1H), 3.26-3.17 (m, 2H), 2.89 (br. s, 1H), 2.17-2.10 (m, 1H), 2.0-1.90 (m, 3H) |
| 11 | 438.20; | (DMSO-d$_6$): 9.4-9.08 (br. hump, exchanged with D$_2$O, 2H), 8.57-8.52 (m, 1H), 8.30-8.20 (m, 2H), 7.84-7.80 (m, 1H), 7.55 (t, J = 8.4 Hz, 1H), 7.41 (t, J = 6.8 Hz, 1H), 4.50-4.44 (m, 1H), 3.37-3.34 (m, 2H), 3.06 (br. q, J = 10.8 Hz, 2H), 2.35 (s, 3H), 2.21-2.08 (m, 4H) |
| 12 | 454.20 | (DMSO-d$_6$): 9.25-9.15 (m, D$_2$O exchangable protons, 2H), 8.54 (br.s, 1H), 8.30-8.20 (m, 2H), 7.82-7.78 (m, 1H), 7.64 (t, J = 8.4 Hz, 1H), 7.31 (t, J = 8.0 Hz, 1H), 4.50-4.45 (m, 1H), 3.95 (s, 3H), 3.37-3.34 (m, 2H), 3.07 (br. q, J = 10.4 Hz, 2H), 2.21-2.12 (m, 4H) |
| 13 | 440.20 | (DMSO-d$_6$): 9.6-9.35 (2 br. humps, exchanged with D$_2$O, 2H), 8.40 (br. s, 1H), 7.95 (s, 1H), 7.57 (t, J = 8.0 Hz, 1H), 7.43 (t, J = 7.2 Hz, 1H), 7.02 (s, 1H), 3.21-3.17 (m, 4H), 3.13 (br. s, 2H), 2.98 (br. s, 2H), 2.38 (s, 3H) |
| 14 | 470.40 | (DMSO-d$_6$ 300 MHz): 9.07 (br, 2H), 8.41 (s, 1H), 7.80-7.68 (m, 1H), 7.49 (s, 1H), 7.42-7.30 (m, 1H), 7.04-6.89 (m, 3H), 3.98 (s, 3H), 3.39-2.84 (m, covered by water peak, 7H), 1.35 (d, 3H) |
| 15 | 455.90 | (DMSO-d$_6$): 9.40 (br. s, exchanged wth D$_2$O, 2H), 8.41 (d, J = 2.4 Hz, 1H), 7.67 (t, J = 8.0 Hz, 1H), 7.58 (s, 1H), 7.35 (t, J = 7.6 Hz, 1H), 7.02 (s, 1H), 3.98 (s, 3H), 3.20-2.80 (series of m, 8H) |
| 16 | 480.20 | (methanol-d$_4$, 300 MHz): 8.40 (d, J = 1.9 Hz, 1H), 8.28 (s, 1H), 8.19 (d, J = 1.8 Hz, 1H), 7.65-7.56 (m, 2H), 7.27 (m, 1H), 4.57 (t, J = 6.4 Hz, 1H), 4.10 (s, 2H), 4.02 (s, 3H), 3.01-2.96 (m, 2H), 2.60-2.53 (m, 2H) and 1.97-1.81 (m, 4H) |

TABLE 2-continued

Analytical Chararacterization Data for Compounds of Formula I (blank cells indicate that the test was not performed)

| Cmpnd. No. | MS (M + H) | $^1$H-NMR (400 MHz, unless indicated otherwise) NMR peaks given as δ values in ppm |
|---|---|---|
| 17 | 480.10 | (methanol-d$_4$, 300 MHz): 8.39 (s, 1H), 8.19 (s, 1H), 8.13 (s, 1H), 7.64-7.59 (m, 2H), 7.31-7.26 (m, 1H), 4.22 (s, 2H), 4.03 (s, 3H), 3.32 (3H), 2.44 (t, J = 11.9 Hz, 2H) and 2.27-2.16 (m, 4H) |
| 18 | 468.30 | (methanol-d$_4$, 300 MHz): 8.39 (s, 1H), 8.19 (s, 1H), 8.13 (s, 1H), 7.64-7.59 (m, 2H), 7.31-7.26 (m, 1H), 4.22 (s, 2H), 4.03 (s, 3H), 3.32 (3H), 2.44 (t, J = 11.9 Hz, 2H) and 2.27-2.16 (m, 4H) |
| 19 | 484.20 | (DMSO-d$_6$, 300 MHz): 8.98 (s, 2H), 8.39 (d, J = 2.4 Hz, H), 7.68 (t, J = 7.4 Hz, H), 7.46 (d, J = 2.4 Hz, H), 7.39-7.33 (m, H), 7.01 (s, H), 6.93 (s, H), 3.98 (s, 3H), 3.21 (m, 2H), 2.94-3.32 (m, 5H), 1.70-1.53 (m, 2H), 0.97 (t, J = 7.4 Hz, 3H) |
| 20 | 456.45 | (methanol-d$_4$, 300 MHz): 8.39 (s, 1H), 7.49 (dd, J = 2.8, 4.7 Hz, 2H), 7.25 (dd, J = 2.1, 17.2 Hz, 1H), 6.89 (s, 1H), 4.41 (s, 2H), 4.03 (s, 3H), 3.52 (t, J = 5.5 Hz, 2H), 2.93 (t, J = 5.6 Hz, 2H) and 2.00 (t, J = 5.4 Hz, 2H) |
| 21 | 456.51 | (methanol-d$_4$, 300 MHz): 8.37 (s, 1H), 7.56-7.48 (m, 2H), 7.29-7.23 (m, 1H), 6.99 (s, 1H), 4.29 (s, 2H), 4.08 (s, 3H), 3.54 (t, J = 5.5 Hz, 2H), 3.07-3.01 (m, 2H) and 2.06 (qn, J = 5.5 Hz, 2H) |
| 22 | 484.50 | (DMSO-d$_6$, 300 MHz): 9.06-8.87 (br, 2H), 8.42 (d, J = 2.3 Hz, 1H), 7.72-7.66 (m, 1H), 7.61 (d, J = 2.1 Hz, 1H), 7.37 (t, J = 7.9 Hz, 1H), 6.96 (s, 1H), 4.00 (s, 3H), 3.35-2.95 (m, 5H), 2.13 (s, 3H), 1.97-1.68 (m, 4H) |
| 23 | 484.30 | (methanol-d$_4$, 300 MHz): 8.39 (d, J = 1.9 Hz, 1H), 8.07 (d, J = 1.7 Hz, 1H), 7.59 (m, 1H), 7.29 (m, 1H), 7.08 (s, 1H), 4.20 (t, J = 6.4 Hz, 2H), 3.45-3.30 (m, 4H), 3.25-3.21 (m, 2H), 3.12-3.09 (m, 2H), 1.91-1.86 (m, 2H) and 1.20-1.06 (m, 3H) |
| 24 |  | (DMSO-d6, 300.0 MHz): 9.12-8.85 (m, 2H), 8.42 (d, J = 2.4 Hz, H), 7.63-7.58 (m, 2H), 7.51-7.46 (m, H), 6.96 (s, H), 3.33 (d, J = 12.5 Hz, 2H), 3.25-3.17 (m, 2H), 3.01 (dd, J = 12.1, 23.1 Hz, 2H), 2.41 (d, J = 1.9 Hz, 3H), 2.12 (s, 3H), 1.94 (d, J = 12.7 Hz, 2H) and 1.82-1.69 (m, 2H) |
| 25 | 468.30 | (methanol-d$_4$, 300 MHz): 8.43 (s, 1H), 8.22-8.09 (m, 2H), 7.89-7.66 (m, 2H), 7.28 (m, 1H), 4.66 (m, 1H), 4.30 (s, 2H), 3.77-3.50 (m, 3H), 3.32-3.18 (m, 2H), 2.60 (s, H), 2.35 (m, 4H) and 1.48 (m, 3H) |
| 26 | 482.50 | (methanol-d$_4$, 300 MHz): 8.41 (s, 1H), 8.19 (m, 2H), 7.60 (m, 2H), 7.28 (m, 1H), 4.62 (m, 1H), 3.76-3.57 (m, 3H), 3.25 (m, 2H), 2.32 (s, 4H) and 1.40 (s, 6H) |
| 27 |  | (DMSO-d6, 300.0 MHz): 8.40 (d, J = 2.4 Hz, H), 7.71-7.64 (m, H), 7.56 (d, J = 2.4 Hz, H), 7.36 (dd, J = 1.9, 17.5 Hz, H), 6.98 (s, H), 3.90 (s, 3H), 3.41 (d, J = 6.8 Hz, 2H), 3.18-2.93 (m, 5H), and 1.31 (d, J = 6.6 Hz, 3H) |
| 28 |  | (DMSO-d6, 300.0 MHz): 9.80-9.50 (m, 2H), 8.43 (d, J = 2.4 Hz, H), 7.74 (d, J = 2.3 Hz, H), 7.61-7.56 (m, H), 7.47-7.41 (m, H), 7.03 (s, H), 3.41-3.35 (m, 2H), 3.28-3.17 (m, H), 3.11-2.99 (m, 4H), 2.38 (d, J = 1.9 Hz, 3H) and 1.32 (d, J = 6.6 Hz, 3H) |
| 29 |  | (DMSO-d$_6$, 300.0 MHz): 9.37 (s, 2H), 8.42 (d, J = 2.4 Hz, H), 7.72-7.65 (m, H), 7.59 (d, J = 2.4 Hz, H), 7.41-7.30 (m, H), 7.08 (s, H), 3.89 (s, 3H), 3.30-3.10 (m, 6H), 3.24 (s, H) and 1.35 (s, 6H) |
| 30 |  | (DMSO-d$_6$, 300.0 MHz): 8.45-8.44 (m, H), 7.67 (d, J = 2.2 Hz, H), 7.62-7.56 (m, H), 7.50-7.38 (m, H), 7.14 (s, H), 3.32-3.05 (m, 6H), 2.38 (d, J = 1.9 Hz, 3H) and 1.35 (s, 6H) |
| 31 |  | (DMSO-d6, 300.0 MHz): 8.98 (s, H), 8.88 (s, H), 8.22 (d, J = 2.3 Hz, H), 7.55 (dd, J = 1.6, 15.1 Hz, H), 7.51-7.41 (m, 2H), 6.72 (s, H), 3.31 (d, J = 12.3 Hz, 2H), 3.06-2.96 (m, 3H), 2.40 (d, J = 1.9 Hz, 3H), 2.04 (d, J = 12.6 Hz, 2H) and 1.92-1.72 (m, 5H) |
| 32 |  | (DMSO-d$_6$, 300.0 MHz): 9.04 (s, H), 8.92 (s, H), 8.23 (d, J = 2.3 Hz, H), 7.72-7.62 (m, H), 7.49 (d, J = 2.3 Hz, H), 7.41-7.32 (m, H), 6.73 (s, H), 3.98 (s, 3H), 3.40-3.29 (m, 2H), 3.10-2.92 (m, 3H), 2.05 (d, J = 12.5 Hz, 2H), 1.93 (s, 3H) and 1.85-1.71 (m, 2H) |
| 33 | 484.30 | (methanol-d$_4$, 300 MHz): 8.38 (d, J = 2.2 Hz, 1H), 8.00 (d, J = 2.2 Hz, 1H), 7.59-7.52 (m, 1H), 7.29 (m, 1H), 7.06 (s, 1H), 4.90-4.77 (m, 1H), 3.52-3.27 (m, 4H), 3.22-3.16 (m, 2H), 3.10-3.07 (m, 2H) and 1.43-1.32 (m, 6H) |
| 34 | 482.20 | (methanol-d$_4$, 300 MHz): 8.39 (s, 1H), 8.19 (m, 2H), 7.63 (m, 2H), 7.26 (s, 1H), 4.61 (m, 1H), 4.17 (m, 2H), 3.55 (m, 2H), 3.24 (m, 2H), 2.32 (m, 4H), 1.87 (d, J = 5.6 Hz, 2H) and 1.07 (t, J = 6.9 Hz, 3H) |
| 35 | 498.45 | (DMSO-d$_6$): d 8.92 (d, J = 8.8 Hz, 1H), 8.70 (d, J = 7.8 Hz, 1H), 8.45 (d, J = 1.8 Hz, 1H), 8.10 (s, 1H), 7.80 (s, 1H), 7.70 (s, 1H), 7.64-7.58 (m, 1H), 7.35-7.29 (m, 1H), 6.78 (s, 1H), 4.49-4.42 (m, 2H), 4.33-4.30 (m, 2H), 3.71-3.68 (m, 2H), 3.38 (d, J = 11.9 Hz, 2H), 3.30 (s, 3H), 3.17-3.06 (m, 3H) and 2.27-2.05 (m, 4H) |

TABLE 2-continued

Analytical Chararacterization Data for Compounds of Formula I (blank cells indicate that the test was not performed)

| Cmpnd. No. | MS (M + H) | $^1$H-NMR (400 MHz, unless indicated otherwise) NMR peaks given as δ values in ppm |
|---|---|---|
| 36 | 522.30 | (DMSO-d$_6$): 8.7 (m, 1H), 8.4 (m, 1H), 8.2 (m, 2H), 7.6 (m, 1H), 7.35-7.25 (m, 2H), 6.8 (br s, 1H), 4.6 (m, 1H), 3.95 (s, 3H), 3.4 (m, 2H), 3.1 (m, 2H), 2.25 (m, 2H), 2.1 (m, 2H) |
| 37 | 453.80 | (DMSO-d$_6$): 9.34-9.22 (m, exchanged with D$_2$O, 2H), 8.58 (d, J = 2.0 Hz, 1H), 8.19 (s, 1H), 8.12 (s, 1H), 7.78 (s, 1H), 7.17 (d, J = 10.8 Hz, 2H), 4.50-4.44 (m, 1H), 3.86 (s, 3H), 3.41-3.33 (m, 2H), 3.10-3.03 (m, 2H), 2.21-2.09 (m, 4H) |
| 38 | 435.80 | (DMSO-d$_6$): 9.21 (br. s, exchanged with D$_2$O, 1H), 9.08 (br. s, exchanged with D$_2$O, 1H), 8.50 (s, 1H), 8.09 (br. s, 1H), 7.90 (br. overlapped s, 1H), 7.89 (d, J = 8.0 Hz, 1H), 7.63 (d, J = 6.8 Hz, 2H), 7.52 (d, J = 7.6 Hz, 1H), 4.49-4.44 (m, 1H), 3.38-3.35 (m, 2H), 3.11-3.03 (m, 2H), 2.41 (s, 3H), 2.20-2.08 (m, 4H) |
| 39 | 437.80 | (DMSO-d$_6$): 9.70 (br. s, exchanged with D$_2$O, 2H), 8.40 (br. s, 1H), 7.89 (d, J = 8.4 Hz 1H), 7.67 (s, 1H), 7.53 (d, J = 8.4 Hz, 2H), 6.97 (br. s, 1H), 3.20-3.14 (m, 6H), 2.98-2.97 (m, 2H), 2.44 (s, 3H) |
| 40 | 435.90 | (DMSO-d$_6$): 9.32-9.30 (m, exchanged with D$_2$O, 1H), 9.20-9.18 (m, exchanged with D$_2$O, 1H), 8.52 (d, J = 2.0 Hz, 1H), 8.37 (br. s, 1H), 8.22 (br. s, 1H), 7.82 (br. s, 1H), 7.75 (d, J = 1.6 Hz, 1H), 7.55 (d, J = 8.0 Hz, 1H), 7.45 (br. d, J = 8.4 Hz, 1H), 4.50-4.45 (m, 1H), 3.35-3.32 (m, 2H), 3.07-3.04 (m, 2H), 2.36 (s, 3H), 2.20-2.09 (m, 4H) |
| 41 | 419.90 | (DMSO-d$_6$): 9.21-9.05 (m, exchanged with D$_2$O, 2H), 8.51 (br. s, 1H), 8.15-8.10 (m, 2H), 7.75-7.68 (m, 2H), 7.38 (br. d, J = 10.8 Hz, 1H), 7.32 (br. d, J = 8.4 Hz, 1H), 4.49-4.44 (m, 1H), 3.37-3.34 (m, 2H), 3.11-3.03 (m, 2H), 2.40 (s, 3H), 2.21-2.10 (m, 4H) |
| 42 | 421.80 | (DMSO-d$_6$): 9.43 (br. s, exchanged with D$_2$O, 2H), 8.39 (d, J = 2.4Hz, 1H), 7.74 (t, J = 8.0 Hz, 1H), 7.54 (d, J = 2.0 Hz, 1H), 7.41 (d, J = 10.8 Hz, 1H), 7.34 (d, J = 8.0 Hz, 1H), 6.97 (s, 1H), 3.22-3.21 (m, 4H), 3.13-3.12 (m, 2H), 2.97-2.95 (m, 2H), 2.42 (s, 3H) |
| 43 | 419.90 | (DMSO-d$_6$): 9.29 (br. s, exchanged with D$_2$O, 1H), 9.16 (br. s, exchanged with D$_2$O, 1H), 8.53 (s, 1H), 8.38 (br. s, 1H), 8.22 (s, 1H), 7.83 (s, 1H), 7.50 (dd as t, J = 8.4 Hz, 2H), 7.33 (dd, J = 8.4, 2.0 Hz, 1H), 4.51-4.44 (m, 1H), 3.35-3.32 (m, 2H), 3.1-3.02 (m, 2H), 2.27 (s, 3H), 2.20-2.09 (m, 4H) |
| 44 | 482.40 | (DMSO-d$_6$): 8.3 (s, 1H), 8.25 (m, 1H), 7.78 (s, 1H), 7.68 (m, 1H), 7.37 (m, 1H), 7.32 (m, 1H), 6.65 (br s, 2H), 4.35 (m, 1H), 3.97 (s, 3H), 3.15-2.87 (m, 4H), 2.2-1.95 (m, 4H), 1.9 (m, 3H), 1.85-1.6 (m, 2H) |
| 45 | 452.40 | (DMSO-d$_6$): 8.25 (m, 2H), 7.7 (s, 1H), 7.6 (m, 1H), 7.43 (m, 1H), 7.39 (m, 1H), 6.65 (br s, 2H), 4.15 (m, 1H), 3.15 (m, 2H), 2.7 (m, 2H), 2.37 (s, 3H), 2.0 (m, 2H), 1.9 (m, 3H), 1.85 (m, 2H) |
| 46 | 466.40 | |
| 47 | 506.30 | (DMSO-d$_6$): 8.22 (s, 1H), 8.16 (m, 1H), 8.1 (s, 1H), 7.52 (m, 1H), 7.49 (m, 1H), 7.32 (m, 1H), 6.8 (br s, 2H), 4.35 (m, 1H), 3.12 (m, 2H), 2.7 (m, 2H), 2.37 (m, 3H), 2.05 (m, 2H), 1.85 (m, 2H) |
| 48 | 464.30 | (DMSO-d$_6$): d6: 8.4 (m, 1H), 8.3 (s, 1H), 8.0 (s, 1H), 7.6-7.5 (m, 3H), 7.4 (m, 1H), 6.45 (m, 2H), 4.77 (m, 1H), 3.1 (m, 2H), 2.75 (m, 4H), 2.39 (m, 3H), 2.2 (m, 2H), 1.9 (m, 2H) |
| 49 | 290.30 | |
| 50 | 435.90 | (DMSO-d$_6$): 9.36-9.24 (br. hump, exchanged with D$_2$O, 2H), 8.56 (br. s, 1H), 8.29-8.23 (m, 2H), 7.81-7.75 (m, 2H), 7.16 (dd, J = 12.4, 2.8 Hz, 1H), 7.06 (dd, J = 8.8, 2.0 Hz, 1H), 4.50-4.45 (m, 1H), 3.83 (s, 3H), 3.36-3.33 (m, 2H), 3.10-3.03 (m, 2H), 2.21-2.12 (m, 4H) |
| 51 | 437.90 | (DMSO-d$_6$): 9.61 (br. s, exchanged with D$_2$O, 2H), 8.41 (d, J = 2.4 Hz, 1H), 7.79 (t, J = 8.8 Hz, 1H), 7.63 (s, 1H), 7.20 (dd, J = 12.4, 2.8 Hz, 1H), 7.08 (dd, J = 9.2, 2.0 Hz, 1H), 7.00 (s, 1H), 3.86 (s, 3H), 3.20-3.14 (m, 6H), 3.00-2.97 (m, 2H) |
| 52 | 435.90 | (DMSO-d$_6$): 9.44-9.34 (br. hump, exchanged with D$_2$O, 2H), 8.56-8.56 (m, 1H), 8.49-8.47 (m, 1H), 8.27 (s, 1H), 7.86 (s, 1H), 7.61 (dd, J = 11.2, 2.4 Hz, 1H), 7.43 (br. d, J = 12.4 Hz, 1H), 7.36 (t, J = 8.4, 1H), 4.51-4.46 (m, 1H), 3.87 (s, 3H), 3.34-3.31 (m, 2H), 3.10-3.00 (m, 2H), 2.18-2.13 (m, 4H) |
| 53 | 437.90 | (DMSO-d$_6$):: 9.58 (br. s, exchanged with D$_2$O, 2H), 8.41 (s, 1H), 7.88 (s, 1H), 7.62 (dd, J = 11.2, 2.0 Hz, 1H), 7.45 (dd, J = 12.4, 2.0 Hz, 1H), 7.36 (t, J = 8.8 Hz, 1H), 7.08 (s, 1H), 3.91 (s, 3H), 3.21-3.16 (m, 6H), 3.01-3.00 (m, 2H) |
| 54 | 455.90 | (DMSO-d$_6$): 9.64 (br. s, exchanged with D$_2$O, 2H), 8.46-8.45 (d, J = 2.0 Hz, 1H), 7.52 (br. s, 1H), 7.22 (d, J = 10.4 Hz, 2H), 7.01 (s, 1H), 3.90 (s, 3H), 3.20-3.14 (m, 6H), 3.01-3.00 (m, 2H) |
| 55 | 453.90 | (DMSO-d$_6$): 9.37-9.22 (br. hump, exchanged with D$_2$O, 2H), 8.57 (s, 1H), 8.42 (br. s, 1H), 8.29 (s, 1H), 7.87 (s, 1H), 7.60-7.52 (m, 2H), 4.53-4.48 (m, 1H), 4.01 (s, 3H), 3.37-3.34 (m, 2H), 3.08-3.06 (m, 2H), 2.20-2.12 (m, 4H) |

TABLE 2-continued

Analytical Chararacterization Data for Compounds of Formula I (blank cells indicate that the test was not performed)

| Cmpnd. No. | MS (M + H) | $^1$H-NMR (400 MHz, unless indicated otherwise) NMR peaks given as δ values in ppm |
|---|---|---|
| 56 | 452.00 | (DMSO-d$_6$): 9.38-9.28 (br. hump, exchanged with D$_2$O, 2H), 8.56 (br. s, 1H), 8.47-8.44 (m, 1H), 8.26 (br. s, 1H), 7.85 (br. s, 1H), 7.81 (br. s, 1H), 7.57 (br. d, J = 8.4 Hz, 1H), 7.34 (d, J = 8.4 Hz, 1H), 4.50-4.48 (m, 1H), 3.91 (s, 3H), 3.36-3.33 (m, 2H), 3.08-3.05 (m, 2H), 2.19-2.14 (m, 4H) |
| 57 | 485.90 | (DMSO-d$_6$): 9.20-9.05 (br. hump, exchanged with D$_2$O, 2H), 8.51 (br. s, 1H), 8.21 (br. s, 2H), 7.86-7.85 (m, 2H), 7.82-7.79 (m, 1H), 4.50-4.45 (m, 1H), 3.88 (s, 3H), 3.36-3.33 (m, 2H), 3.10-3.02 (m, 2H), 2.21-2.11 (m, 4H) |
| 58 | 487.90 | (DMSO-d$_6$): 9.54 (br. s, exchanged with D$_2$O, 2H), 8.43 (s, 1H), 7.89-7.76 (m, 3H), 7.09 (s, 1H), 3.91 (s, 3H), 3.21-3.00 (m, 8H) |
| 59 | 437.90 | (DMSO-d$_6$): 9.72 (br. s, exchanged with D$_2$O, 2H), 8.43 (d, J = 2.0 Hz, 1H), 7.99 (br. s, 1H), 7.79 (d, J = 2.0 Hz, 1H), 7.59 (d, J = 8.0 Hz, 1H), 7.49 (dd, J = 8.4, 2.0 Hz, 1H), 7.10 (s, 1H), 3.20-3.17 (m, 6H), 3.03-3.01 (m, 2H), 2.40 (s, 3H) |
| 60 | 469.90 | (DMSO-d$_6$): 9.44-9.32 (br. hump, exchanged with D$_2$O, 2H), 8.58-8.51 (m, 2H), 8.30 (s, 1H), 7.88 (br. s, 1H), 7.83 (br. s, 2H), 4.53-4.48 (m, 1H), 3.36-3.33 (m, 2H), 3.08-3.05 (m, 2H), 2.45 (s, 3H), 2.22-2.14 (m, 4H) |
| 61 | 471.90 | (DMSO-d$_6$): 9.60 (br. s, exchanged with D$_2$O, 2H), 8.39 (br. s, 1H), 7.80-7.70 (m, 3H), 7.06 (br. s, 1H), 3.30-2.80 (series of m, 8H), 2.49 (s, 3H) |
| 62 | 455.90 | (DMSO-d$_6$): 9.60 (br. s, exchanged with D$_2$O, 2H), 8.44 (br. s, 1H), 7.84 (br. s, 1H), 7.59-7.55 (m, 2H), 7.12 (s, 1H), 4.02 (s, 3H), 3.20-3.16 (m, 6H), 3.02-3.01 (m, 2H) |
| 63 | 453.90 | (DMSO-d$_6$): 9.47 (br. s, exchanged with D$_2$O, 2H), 8.38 (d, J = 2.4 Hz, 1H), 7.80 (d, J = 2.4 Hz, 2H), 7.56 (dd, J = 2.4, 8.8 Hz, 1H), 7.35 (d, J = 9.2 Hz, 1H), 7.05 (s, 1H), 3.92 (s, 3H), 3.21-3.14 (m, 6H), 3.00-2.99 (m, 2H) |
| 64 | 421.90 | (DMSO-d$_6$): 9.51 (br. s, exchanged with D$_2$O, 2H), 8.39 (d, J = 2.4 Hz, 1H), 7.80 (d, J = 2.0 Hz, 1H), 7.54-7.49 (m, 2H), 7.35 (dd, J = 7.6, 2.0 Hz, 1H), 7.05 (s, 1H), 3.21-3.13 (m, 6H), 3.00-2.98 (m, 2H), 2.30 (d, J = 1.2 Hz, 3H) |
| 65 | 468.50 | (DMSO-d$_6$): 8.7 (m, 1H), 8.4 (m, 2H), 8.1 (s, 1H), 7.7-7.6 (m, 3H), 7.5 (m, 1H), 6.55 (m, 1H), 4.6 (s, 2H), 4.45 (m, 1H), 3.45-3.35 (m, 2H), 3.3 (s, 3H), 3.1 (m, 2H), 2.2-2.0 (m, 4H) |
| 66 | 484.40 | (DMSO-d$_6$ 300 MHz): 9.28 (s, 2H), 8.43 (d, J = 2.4 Hz, 1H), 7.73-7.67 (m, 1H), 7.60 (d, J = 2.3 Hz, 1H), 7.41-7.38 (m, 1H), 7.01 (s, 1H), 4.01 (s, 3H), 3.45-3.41 (m, 1H), 3.32-3.25 (m, 2H), 2.89-2.68 (m, 2H), 2.14 (s, 3H), 2.00-1.83 (m, 3H), 1.88 (s, H) and 1.60-1.54 (m, 1H) |
| 67 | 468.40 | (DMSO-d$_6$ 300 MHz): 9.09 (brs, 2H), 8.42 (d, J = 2.4 Hz, 1H), 7.65-7.57 (m, 2H), 7.48-7.43 (m, 1H), 6.99 (s, 1H), 3.41-3.29 (m, 3H), 2.93-2.72 (m, 2H), 2.40 (d, J = 1.7 Hz, 3H), 2.14 (s, 3H), 2.00-1.81 (m, 3H) and 1.65-1.55 (m, 1H) |
| 68 | 452.20 | (methanol-d$_4$, 300 MHz): 8.40 (d, J = 2.0 Hz, 1H), 8.16-8.12 (m, 2H), 7.60-7.55 (m, 2H), 7.47-7.42 (m, 1H), 4.58 (m, 1H), 3.60-3.55 (m, 2H), 3.33-3.19 (m, 2H), 2.84 (q, J = 7.6 Hz, 2H), 2.34-2.28 (m, 4H) and 1.29 (t, J = 7.6 Hz, 3H) |
| 69 | 464.20 | (methanol-d$_4$, 300 MHz): 8.35 (d, J = 2.1 Hz, 1H), 7.99 (s, 1H), 7.84 (d, J = 2.0 Hz, 1H), 7.50-7.44 (m, 2H), 7.09-7.04 (m, 1H), 4.55 (t, J = 5.0 Hz, 1H), 3.59-3.50 (m, 2H), 3.31-3.17 (m, 2H), 2.34-2.19 (m, 5H), 1.20-1.13 (m, 2H) and 0.92-0.88 (m, 2H) |
| 70 | 494.34 | |
| 71 | 482.40 | (DMSO-d$_6$): 8.65 (br s, 1H), 8.4 (m, 2H), 8.07 (s, 1H), 7.7-7.6 (m, 3H), 7.5 (m, 1H), 6.5 (br s, 1H), 4.6 (s, 2H), 4.45 (m, 1H), 3.52 (m, 2H), 3.4 (under H2O) (m, 2H), 3.1 (m, 2H), 2.3-2.0 (m, 4H), 1.12 (t, 3H) |
| 72 | 468.40 | (DMSO-d$_6$): 8.9 (m, 2H), 8.4 (d, 1H), 7.6 (m, 2H), 7.5 (m, 1H), 6.9 (s, 1H), 3.4 (m, 2H), 2.9 (m, 3H), 2.4 (s, 3H), 2.3 (s, 3H), 1.85 (m, 4H) |
| 73 | 484.40 | (DMSO-d$_6$): 9.0 (m, 2H), 8.4 (d, 1H), 7.7 (m, 2H), 7.4 (m, 1H), 7.0 (s, 1H), 3.9 (s, 3H), 3.4 (m, 2H), 3.0 (m, 3H), 2.3 (s, 3H), 1.70 (m, 4H) |
| 74 | 510.30 | (DMSO-d$_6$, 300 MHz): 8.99 (s, 1H), 8.80 (s, 1H), 8.46 (s, 1H), 8.12 (s, 1H), 7.84 (m, 1H), 7.69-7.60 (m, 2H), 7.32 (dd, J = 1.9, 17.3 Hz, 1H), 6.90 (br s, 1H), 5.24 (d, J = 5.7 Hz, 1H), 4.46 (m, 2H), 3.96-3.36 (m, 5H), 3.12-3.02 (m, 2H), 2.37-1.93 (m, 6H) |
| 75 | 510.30 | (DMSO-d$_6$, 300 MHz): 8.99 (s, 1H), 8.80 (s, 1H 8.46 (s, 1H), 8.12 (s, 1H), 7.84 (m, 1H), 7.69-7.60 (m, 2H), 7.32 (dd, J = 1.9, 17.3 Hz, 1H), 6.90 (br s, 1H), 5.24 (d, J = 5.7 Hz, 1H), 4.46 (m, 2H), 3.96-3.36 (m, 5H), 3.12-3.02 (m, 2H), 2.37-1.93 (m, 6H) |

TABLE 2-continued

Analytical Chararacterization Data for Compounds of Formula I (blank cells indicate that the test was not performed)

| Cmpnd. No. | MS (M + H) | $^1$H-NMR (400 MHz, unless indicated otherwise) NMR peaks given as δ values in ppm |
|---|---|---|
| 76 | 496.50 | |
| 77 | 478.30 | (DMSO-$d_6$, 300 MHz): 8.92 (s, 1H), 8.79 (d, J = 4.9 Hz, 1H), 8.55 (d, J = 2.4 Hz, 1H), 8.40 (d, J = 8.3 Hz, 1H), 7.97 (dd, J = 5.5, 8.1 Hz, 1H), 7.77-7.67 (m, 2H), 7.38 (t, J = 7.8 Hz, 1H), 7.29 (s, 1H), 3.97 (s, 3H) and 2.33 (s, 3H) |
| 78 | 471.40 | (DMSO-$d_6$, 300 MHz): 9.28 (brs, 1H), 9.15 (brs, 1H), 8.48 (d, J = 2.4 Hz, 1H), 7.87 (s, 1H), 7.70-7.63 (m, 2H), 7.35-7.31 (m, 1H), 3.99 (s, 3H), 3.33-3.30 (m, 3H), 3.02 (dd, J = 11.9, 22.8 Hz, 2H) and 2.18-1.87 (m, 4H) |
| 79 | 478.30 | (DMSO-$d_6$, 300 MHz): 8.85 (d, J = 6.8 Hz, 2H), 8.59 (d, J = 2.4 Hz, 1H), 8.00 (d, J = 6.8 Hz, 2H), 7.71-7.68 (m, 2H), 7.41-7.36 (m, 2H), 3.98 (s, 3H) and 2.51 (s, 3H covered by DMSO) |
| 80 | 462.40 | (DMSO-$d_6$, 300 MHz): 8.82 (d, J = 6.9 Hz, 2H), 8.57 (d, J = 2.5 Hz, 1H), 7.97 (d, J = 6.9 Hz, 2H), 7.73 (d, J = 2.5 Hz, 1H), 7.65-7.57 (m, 1H), 7.52-7.42 (m, 1H), 7.37 (s, 1H) and 2.38 (d, J = 1.9 Hz, 3H) |
| 81 | 455.40 | (DMSO-$d_6$, 300 MHz): 8.43 (d, J = 2.4 Hz, 1H), 7.74 (s, 1H), 7.60-7.55 (m, 1H), 7.52 (d, J = 2.4 Hz, 1H), 7.43 (t, J = 7.3 Hz, 1H), 6.92 (s, 1H), 3.08-3.00 (m, 3H), 2.73-2.62 (m, 2H), 2.40 (d, J = 1.9 Hz, 3H), 1.97 (d, J = 12.6 Hz, 2H) and 1.65-1.52 (m, 2H) |

Biological Assay of Compounds of the Invention

Example 31 c-MET Kinase Inhibition Assay

Compounds of the invention were screened for their ability to inhibit c-MET kinase using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 µL per well containing 1.0 nM c-Met, 100 mM HEPES (pH 7.5), 10 mM $MgCl_2$, 25 mM NaCl, 0.01% BSA, 1 mM DTT, 0.5 mg/mL polyE4Y, and 35 µM ATP. Accordingly, compounds of the invention were dissolved in DMSO to make 10 mM initial stock solutions. Serial dilutions in DMSO were then made to obtain the final solutions for the assay. A 1.5 µL aliquot of DMSO or inhibitor in DMSO was added to each well. The reaction was initiated by the addition of $^{33}$P-ATP and polyE4Y (obtained from Sigma). After 20 min, the reaction was quenched with 50 µL of 30% trichloroacetic acid (TCA) containing 4 mM ATP. The reaction mixture was transferred to the 0.66 mm GF filter plates (Corning) and washed three times with 5% TCA. Following the addition of 50 µL of Ultimate Gold™ high efficiency scintillant (Packard Bioscience), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. Each of Compounds 1 to 81 had a $K_i$ of 260 nM or less as measured by this assay.

Example 32

Inhibition c-Met Activity in Snu5 Gastric Carcinoma Cells

Compounds of the invention were also screened for their ability to inhibit the Luciferase-induced signal in an engineered Snu5 cell line. Snu5 [obtained from American Type Culture Collection (Catalog number CRL-5973)] is a human gastric carcinoma known to overexpress c-Met, which is constitutively active. The cell line was transduced with the retrovirus, pCLPCX, which contains a genetic construct consisting of 6×AP1 promoter response elements and a luciferase gene having a C-terminal PEST sequence (proteolytic signal from mouse ornithine decarboxylase, which reduces the half-life of the luciferase). The constitutively active cMet activates cellular pathways (principally MAP kinase), resulting in AP-1-induced transcription of luciferase-PEST and translation into the final product, the activity of which is quantifiable as a chemiluminescent readout upon the addition of luciferin (Steady-Glo from Promega.). Residual luminescence is strongly correlated to the inhibition of c-Met. A stable cell line was obtained by selecting the new cell line (Snu5-AP1-Luc-Pest) with puromycin. The cells were grown in complete media [Iscove's media (Invitrogen) containing 10% fetal bovine serum (FBS, Hyclone) and penicillin/gentamycin (Invitrogen)]. Compounds of the invention were dissolved in DMSO to make 10 mM initial stock solutions. Serial dilutions in DMSO were then made and transferred to complete medium to make a 10× solution. The Snu5-AP1-Luc-Pest cells were counted and diluted to 200,000-cells/mL solution. The cells (90 µL) were added to each well in a 96-well black with clear bottom plate (Costar). Then 10 µL of the 10× compound solution was added to the cells in triplicate. The plates were incubated in a 37° C./5% $CO_2$ incubator. After 6 hours, 50 µL of the Steady Glo reagent (Promega) was added to each well and placed on a plate shaker for 5 minutes to ensure that the cells were completely lysed. The plate was read on a 1450 Microbeta Liquid Scintillation and Luminescence Counter (Perkin-Elmer). The $IC_{50}$s were calculated using a 4-parameter fit using the graphing software Prism (GraphPad). Compounds 2-6, 8, 10, 13-19, 22-30, 32-34, 36, 37, 44-46, 66, and 67 had $IC_{50}$'s of 100 nM or less. Compounds 1, 7, 9, 11, 12, 20, 21, 31, 35, 38, 39, 41-43, 47, 48, 50, 51, 54, and 65 had $IC_{50}$'s of greater than 100 nM and less than or equal to 1000 nM. Compound 40 had an $IC_{50}$ greater than 1000 nM.

Representative compounds in which the tetrazolyl phenyl is substituted at the 4-position ($R^5$ of Formula I) have a lower $IC_{50}$ value (i.e., are more active) for c-Met inhibition than analogs having a hydrogen at this position ias measured by the Snu5 gastric carcinoma cell assay. In representative examples, compounds 4, 6, 8, 9, 10, 12, 14, 15, 16, 17, 18, 19, 21, 22, 27, 29, 32, 36, and 49 of formula I, wherein $R^5$ is —$OCH_3$ are more active than corresponding analogs wherein $R^5$ is hydrogen, The range of $IC_{50}$ values for the methoxy substituted compounds is from 18 nm to 290 nM, whereas the range of $IC_{50}$ values for the corresponding unsubstituted compounds is from 59 nm to 530 nM. Thus, seventeen of the eighteen methoxy substituted compounds have a lower $IC_{50}$ value than that of the respective hydrogen comparator, with a median $IC_{50}$ difference of 141 nM (Wilcoxon p value of <0.0001). The one exception is compound 9, wherein the unsubstituted compound has a lower $IC_{50}$ value than the corresponding methoxy substituted compound.

In other representative examples, compounds 1, 2, 3, 5, 7, 11, 13, 24, 28, 30, and 31 of formula I, wherein $R^5$ is —$CH_3$ are more active than corresponding analogs wherein $R^5$ is hydrogen. The range of $IC_{50}$ values for the methyl substituted compounds is from 33 nm to 190 nM, whereas the range of $IC_{50}$ values for the corresponding unsubstituted compounds is from 90 nm to 450 nM. Thus, ten of the eleven methyl substituted compounds have a lower $IC_{50}$ value than that of the respective hydrogen comparator, with a median $IC_{50}$ difference of 101 nM (Wilcoxon p value of 0.002). The one exception is compound 31, wherein the unsubstituted compound has a lower $IC_{50}$ value than the corresponding methyl substituted compound.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

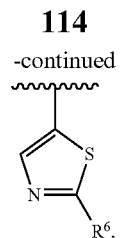
(I)

or a pharmaceutically acceptable salt thereof, wherein $R^A$ is

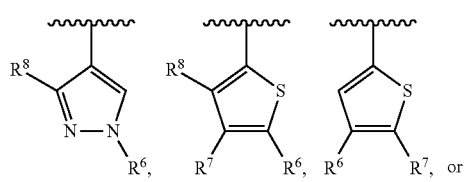

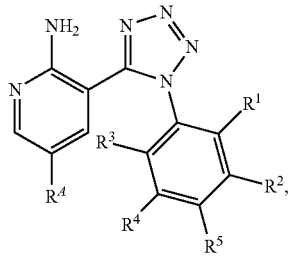

wherein each of $R^1$, $R^2$, $R^3$, and $R^4$ is, individually, hydrogen, Cl, or F, wherein at least one of $R^1$, $R^2$, $R^3$, and $R^4$ is Cl or F;

$R^5$ is $C_{1-4}$ aliphatic, $CH(R^{5a})_2$, O—$C_{1-4}$ aliphatic, $CH_2$—O—$C_{1-3}$ aliphatic, O—$(CH_2)_2$—O—$C_{1-3}$ aliphatic, or O—$CH_2C(R^{5a})_3$, wherein each $R^{5a}$ is, independently, hydrogen, or $C_{1-3}$ aliphatic, or two $R^{5a}$ together with the intervening carbon atom forms a 3-6 membered carbocyclic ring or a 5-6 membered heterocyclic ring having 1-2 oxygen atoms;

$R^6$ is

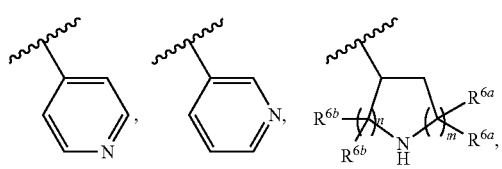

wherein each of m and n is, individually, 1 or 2, and each of $R^{6a}$ and $R^{6b}$ is, individually, hydrogen or a $C_{1-4}$ aliphatic, or two $R^{6a}$ or two $R^{6b}$ groups together with the carbon to which they are bonded form a cyclopropyl ring, and wherein one $R^{6a}$ together with one $R^{6b}$ optionally form a 5 or 6-membered ring via a bond or an $C_{1-2}$ alkylidene linkage;

$R^7$ is a $C_{1-4}$ aliphatic, O—$C_{1-4}$ aliphatic, $C_{1-4}$ aliphatic-O—$C_{1-4}$ aliphatic, or $R^6$ and $R^7$ together with the thiophene ring to which they are bonded form the following structure:

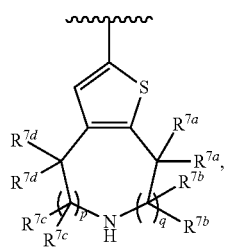

wherein each of $R^{7a}$, $R^{7b}$, $R^{7c}$, and $R^{7d}$ is, individually, hydrogen or a $C_{1-4}$ aliphatic, or two $R^{7a}$, $R^{7b}$, $R^{7c}$, or $R^{7d}$ groups together with the intervening atom form a cyclopropyl ring;

each of p and q is, individually, 0, 1, or 2; and $R^8$ is hydrogen, $CH_3$ or $CF_3$.

2. The compound of claim 1, or a pharmaceutically acceptable salt thereof, wherein $R^4$ is

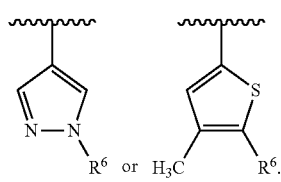

3. The compound of claim 1, or a pharmaceutically acceptable salt thereof, wherein $R^6$ is

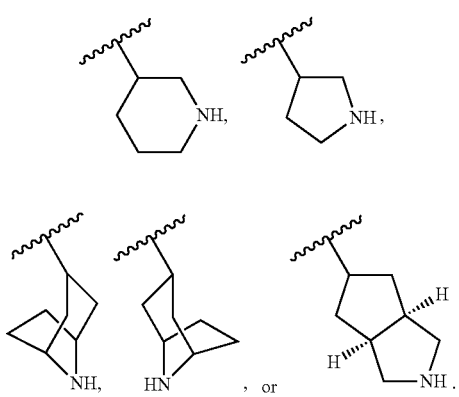

4. The compound of claim 1, or a pharmaceutically acceptable salt thereof, wherein $R^6$ is

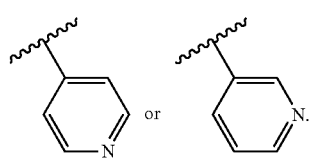

5. The compound of claim 1, or a pharmaceutically acceptable salt thereof, wherein wherein $R^A$ is

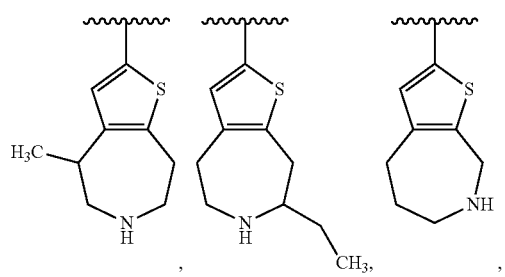

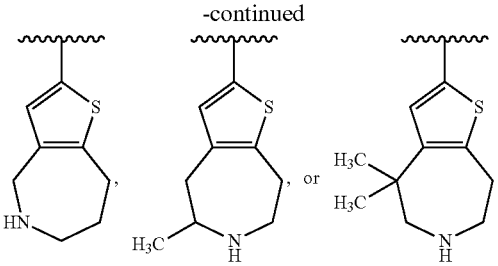

6. The compound of claim 1, or a pharmaceutically acceptable salt thereof, wherein one or two of $R^1$, $R^2$, $R^3$, and $R^4$ is fluorine and the remainder of $R^1$, $R^2$, $R^3$, and $R^4$ are hydrogen.

7. The compound of claim 6, or a pharmaceutically acceptable salt thereof, wherein each of $R^1$ and $R^2$ is fluorine and each of $R^3$ and $R^4$ is hydrogen.

8. The compound of claim 1, or a pharmaceutically acceptable salt thereof, wherein $R^5$ is $C_{1-4}$ aliphatic, cyclopropyl, O—$C_{1-4}$ aliphatic, or —$OCH_2$-cyclopropyl.

9. The compound of claim 1, or a pharmaceutically acceptable salt thereof, wherein $R^5$ is

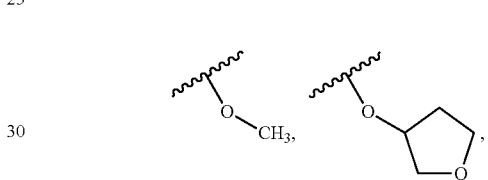

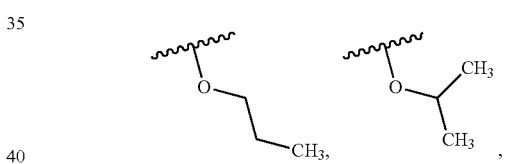

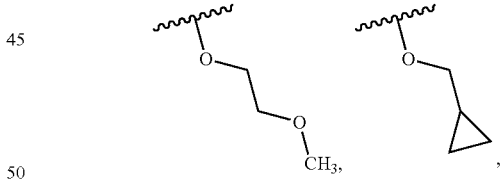

10. The compound of claim 9, or a pharmaceutically acceptable salt thereof, wherein $R^5$ is $OCH_3$ or $CH_3$.

11. The compound of claim 1, or a pharmaceutically acceptable salt thereof, wherein said compound is selected from
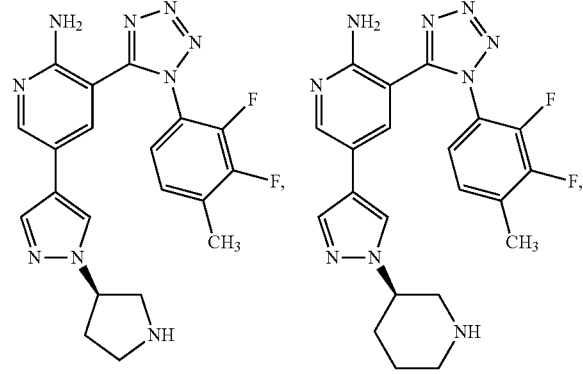
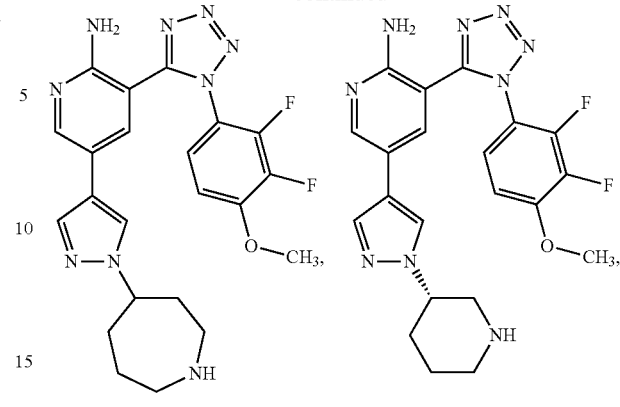
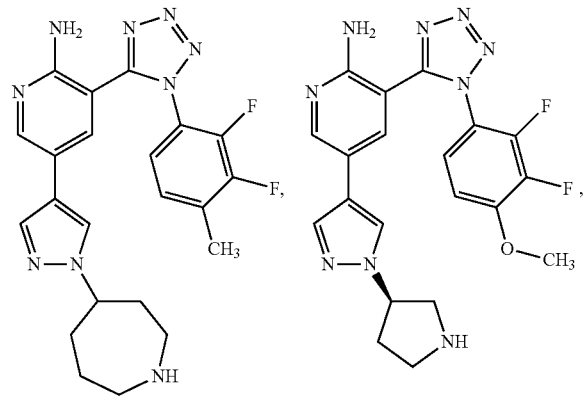
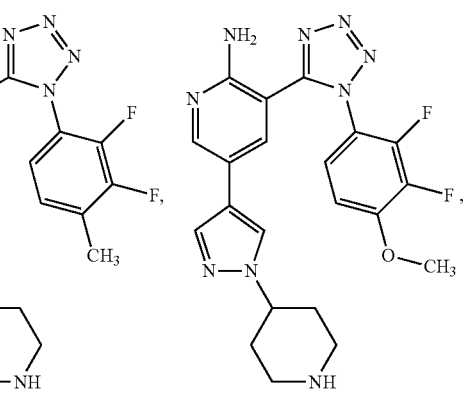
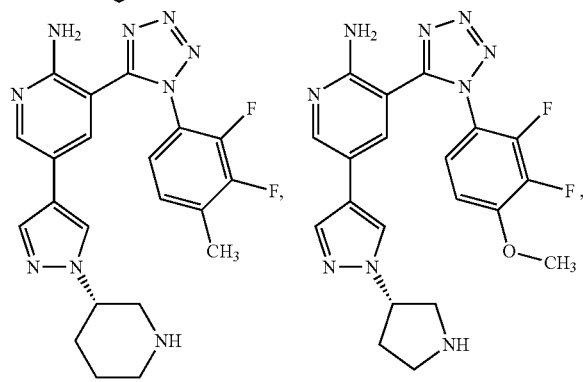
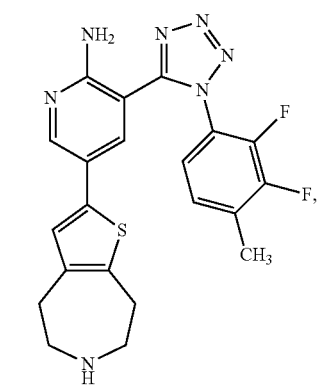
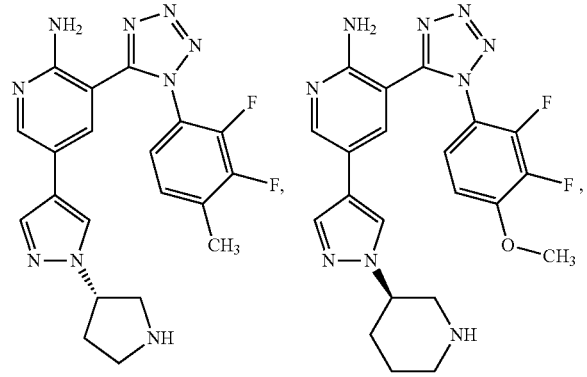
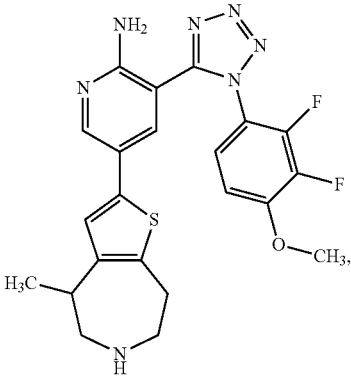

-continued
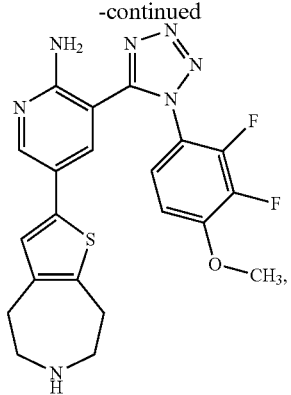
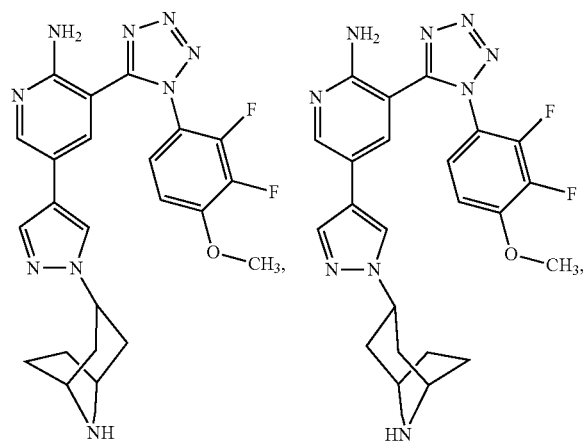
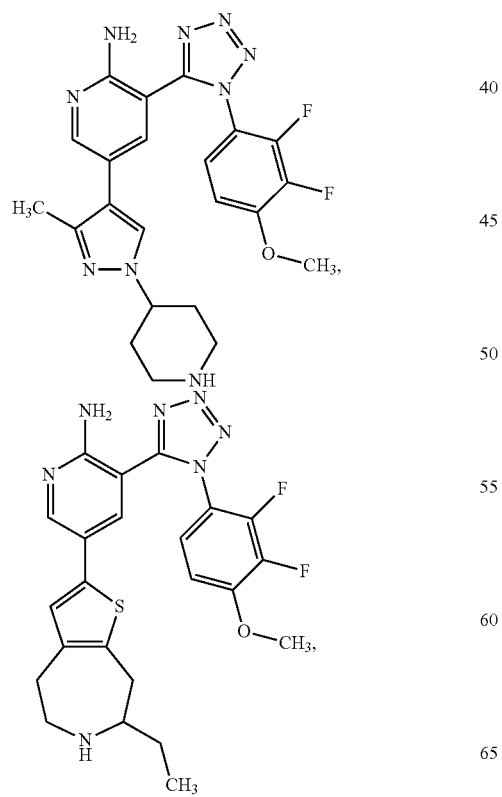
-continued
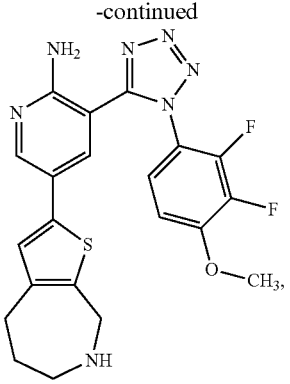
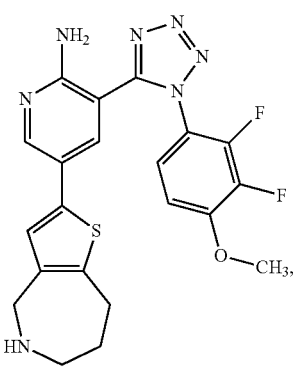
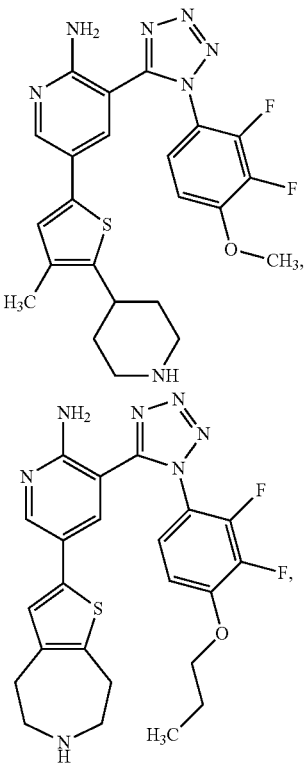

121
-continued
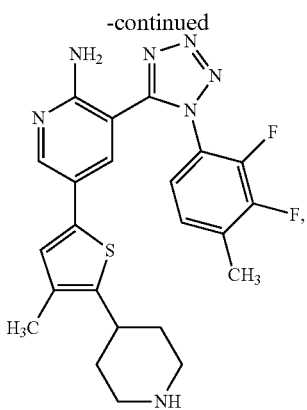
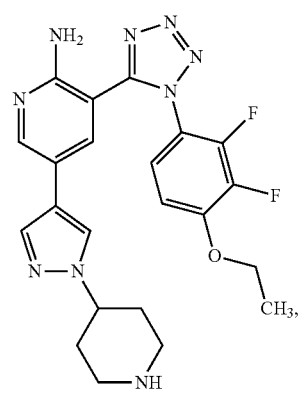
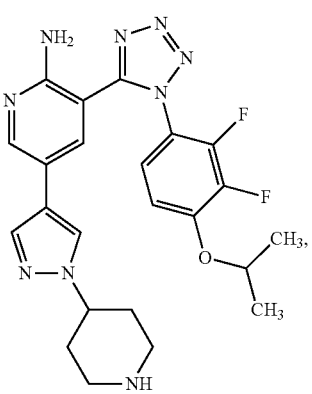
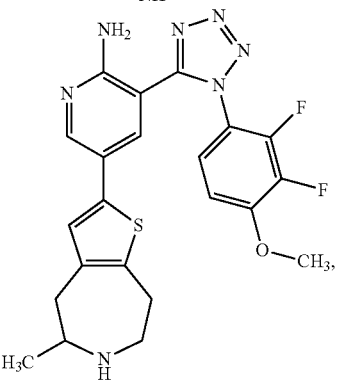
122
-continued
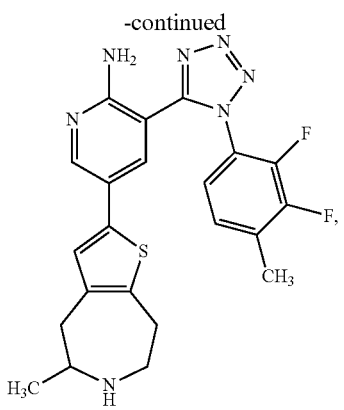
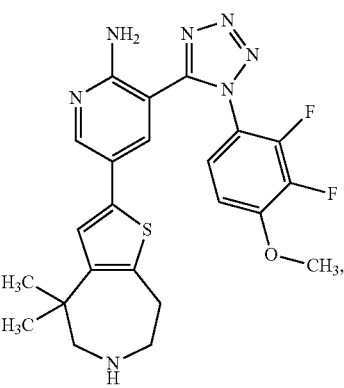
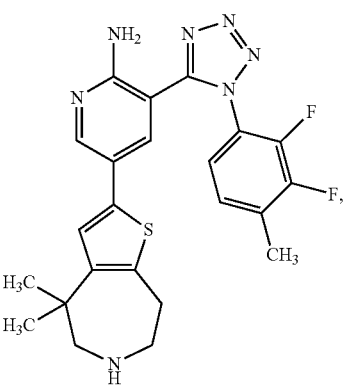
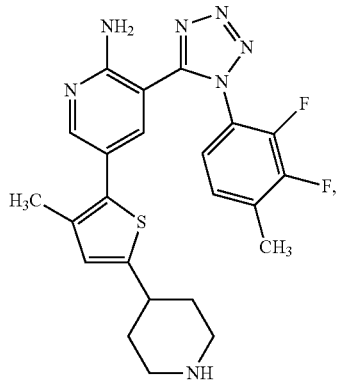

123
-continued
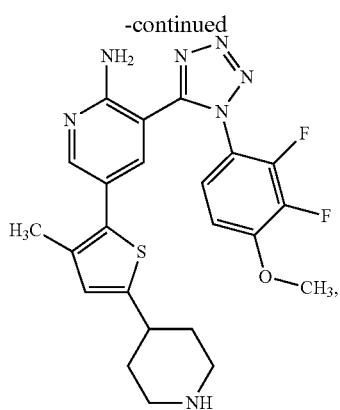
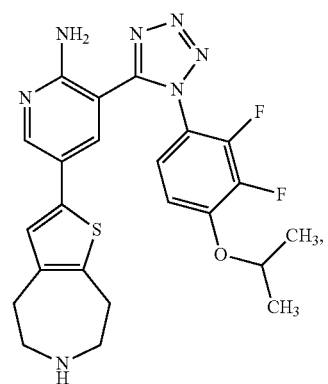
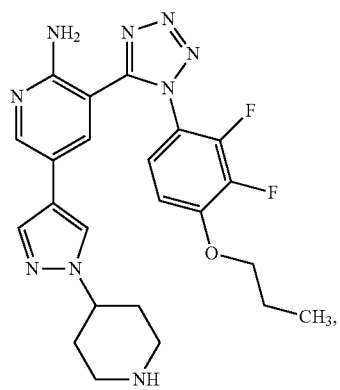
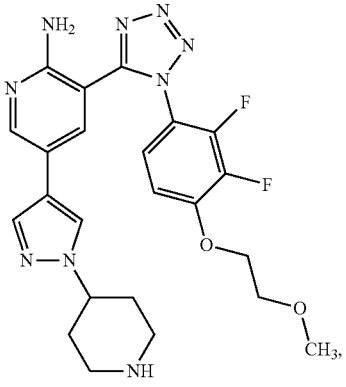
124
-continued
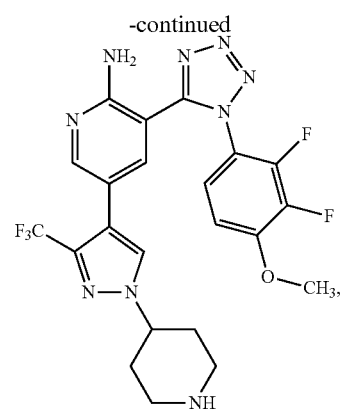
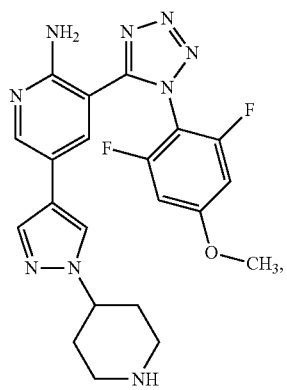 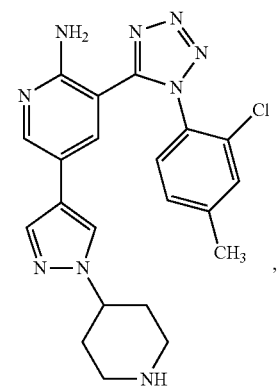
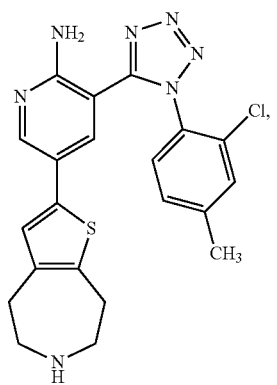 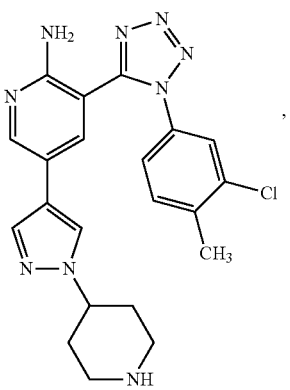
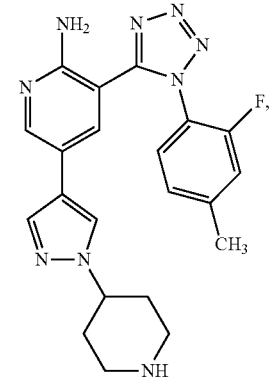 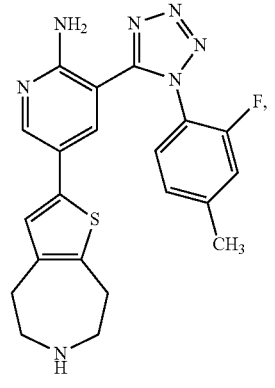

-continued
125
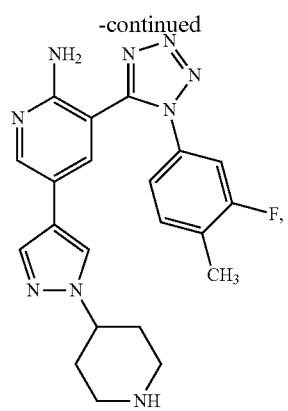
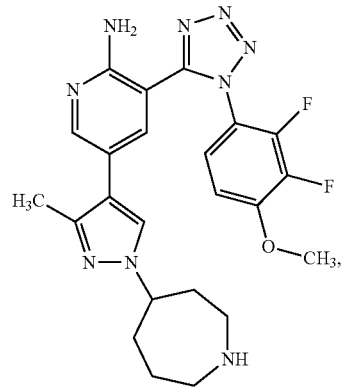
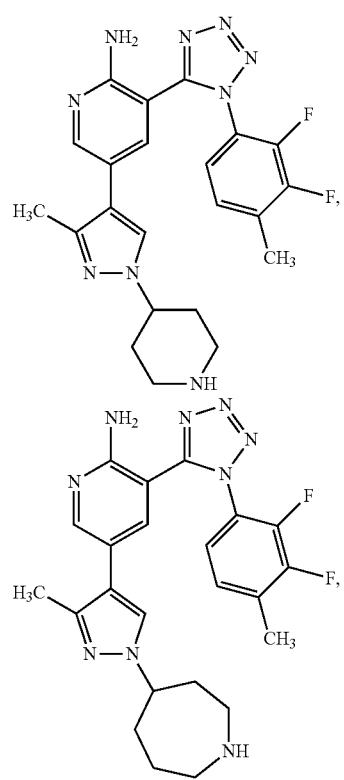
-continued
126
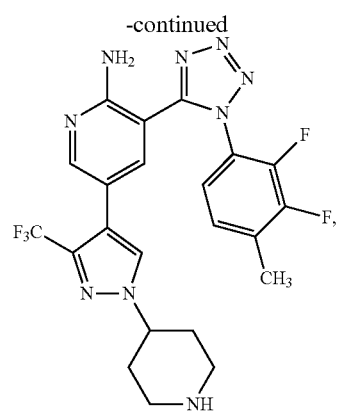
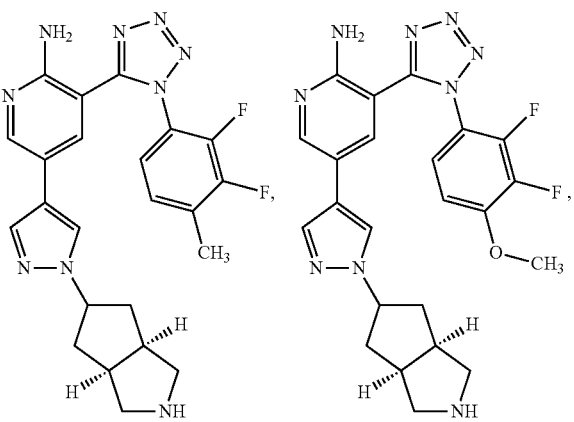
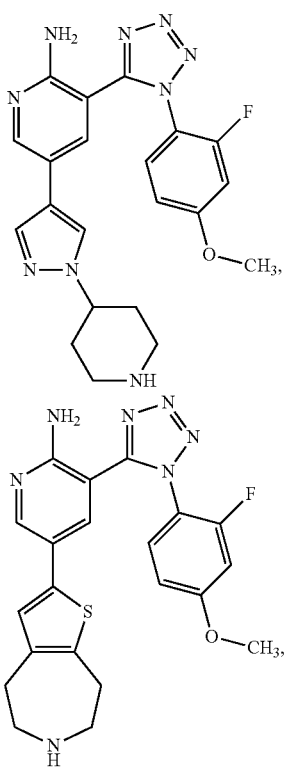

127 -continued
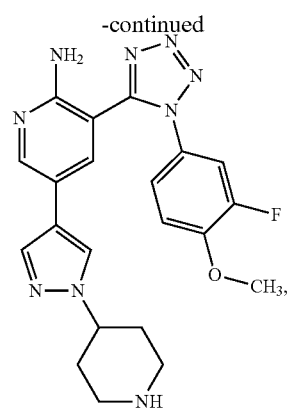
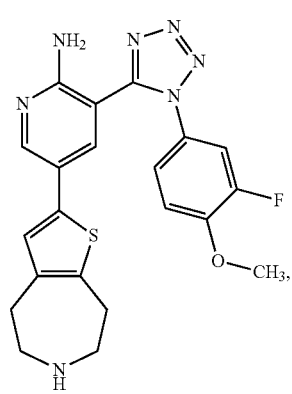
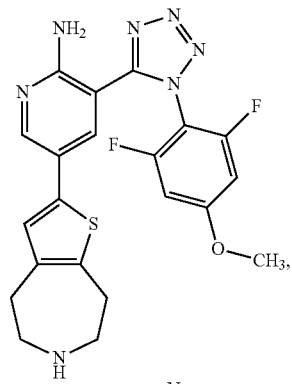
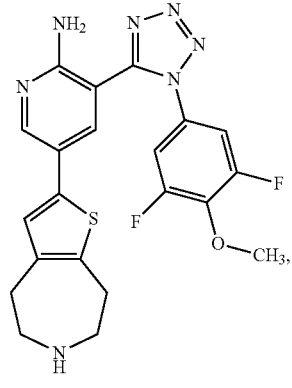
128 -continued
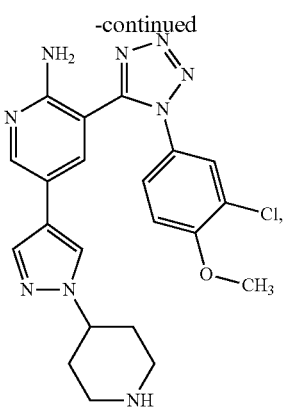
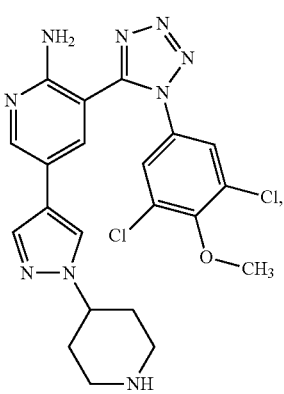
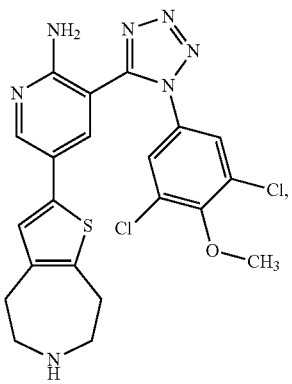
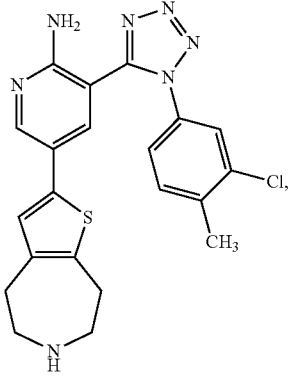

129
-continued
130
-continued
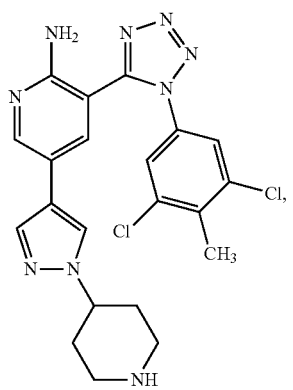
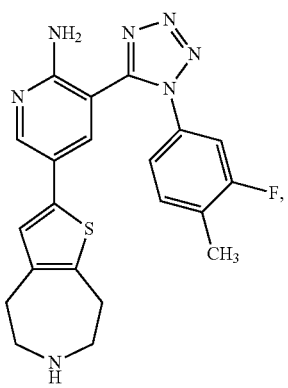

131
-continued
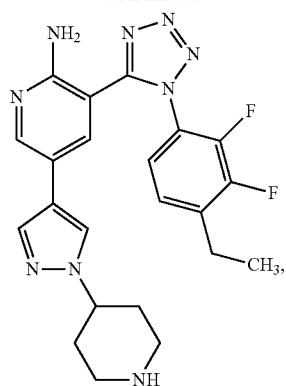
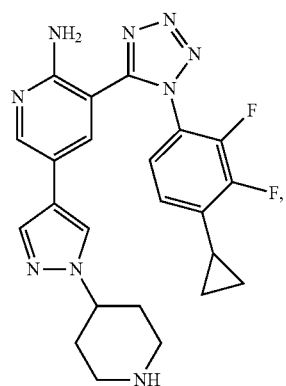
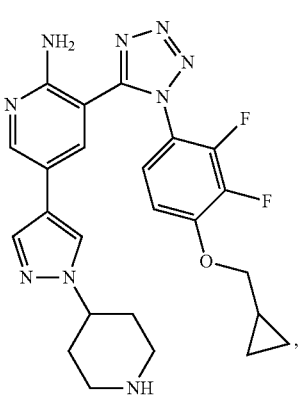
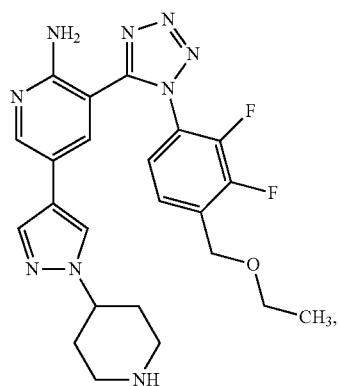
132
-continued
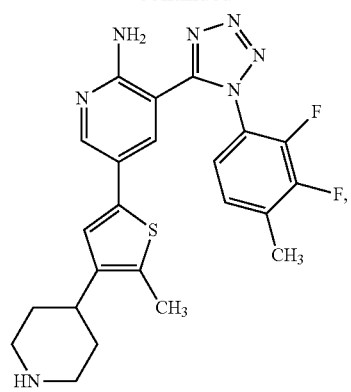
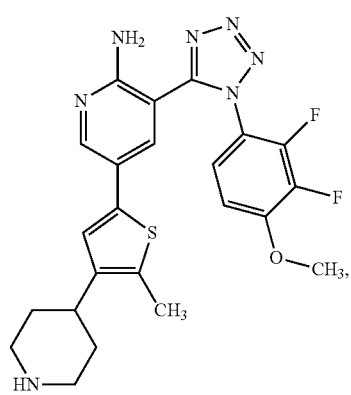
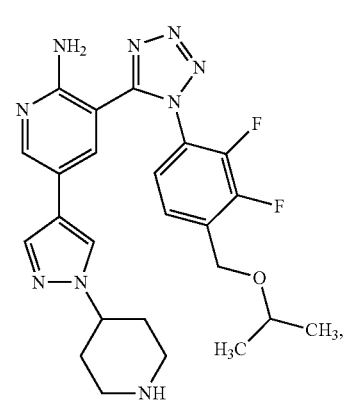
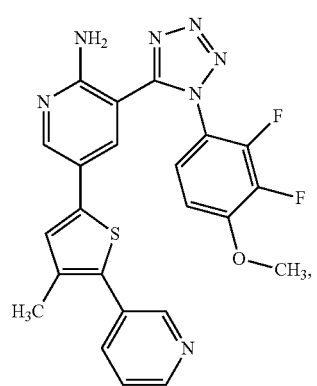

-continued

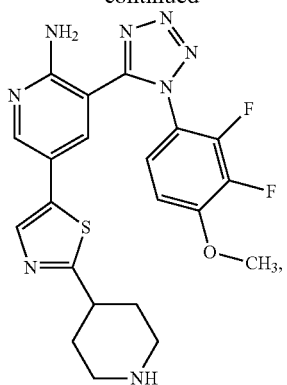

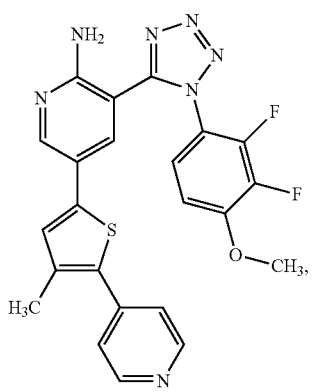

-continued

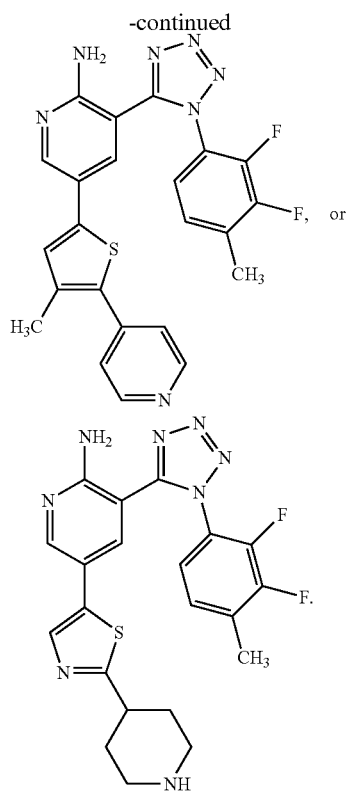

12. A pharmaceutical composition comprising a compound according to claim 1, or a pharmaceutically acceptable salt thereof, and a pharmaceutically acceptable carrier, adjuvant or vehicle.

13. A method of treating or lessening the severity of a proliferative disorder selected from a glioblastoma; a gastric carcinoma; or a cancer selected from colon, breast, prostate, brain, liver, pancreatic or lung cancer in a patient comprising administering a compound according to claim 1, or a pharmaceutical composition comprising said compound, in an amount sufficient to treat or lessen the severity of said proliferative disorder in said patient.

* * * * *